US008829431B2

(12) United States Patent
Verbeck, IV

(10) Patent No.: US 8,829,431 B2
(45) Date of Patent: Sep. 9, 2014

(54) NANOMANIPULATION COUPLED NANOSPRAY MASS SPECTROMETRY (NMS)

(71) Applicant: University of North Texas, Denton, TX (US)

(72) Inventor: Guido Fridolin Verbeck, IV, Plano, TX (US)

(73) Assignee: University of North Texas, Denton, TX (US)

( * ) Notice: Subject to any disclaimer, the term of this patent is extended or adjusted under 35 U.S.C. 154(b) by 0 days.

(21) Appl. No.: 13/795,994

(22) Filed: Mar. 12, 2013

(65) Prior Publication Data
US 2013/0206976 A1 Aug. 15, 2013

Related U.S. Application Data

(62) Division of application No. 13/270,962, filed on Oct. 11, 2011.

(60) Provisional application No. 61/391,842, filed on Oct. 11, 2010.

(51) Int. Cl.
G01N 1/04 (2006.01)
H01J 49/04 (2006.01)
G01N 21/65 (2006.01)
H01J 49/00 (2006.01)

(52) U.S. Cl.
CPC ......... H01J 49/0027 (2013.01); H01J 49/0459 (2013.01); G01N 21/65 (2013.01)
USPC ........................... 250/288; 73/864.71; 73/864

(58) Field of Classification Search
USPC ............... 250/281, 282, 288; 73/864, 864.71; 361/234
See application file for complete search history.

(56) References Cited

U.S. PATENT DOCUMENTS

| 4,607,011 | A |   | 8/1986  | Kaplan et al. |           |
|-----------|---|---|---------|---------------|-----------|
| 5,349,186 | A |   | 9/1994  | Ikonomou et al. |         |
| 5,571,976 | A | * | 11/1996 | Drolet         | 73/864.71 |
| 5,859,375 | A | * | 1/1999  | Danylewych-May et al. | 73/864.71 |
| 6,812,460 | B1 |  | 11/2004 | Stallcup, II et al. |      |
| 7,385,189 | B2 |  | 6/2008  | Goodley et al. |          |

(Continued)

OTHER PUBLICATIONS

Ricci et al, "Combining the Tape-Lift Method and Fourier Transform Spectroscopic Imaging for Forensic Applications", Applied Spectroscopy vol. 60 No. 9 2006 1013-1021.*

(Continued)

Primary Examiner — Michael Logie
Assistant Examiner — David E Smith
(74) Attorney, Agent, or Firm — Edwin S. Flores; Chainey P. Singleton; Chalker Flores, LLP

(57) ABSTRACT

A coupled nanomanipulation and nanospray mass spectrometry (NMS) system for single cell, single organelle, and ultra-trace molecular analysis is disclosed herein. The system primarily comprises a bio-workstation coupled to a NMS. The bio-workstation primarily comprises of a nanomanipulator stage with a plurality of nano-positioners attached to a cabinet with a piezo voltage source and a pressure injector. The present invention further describes a fingerprint lift method that when coupled with the system disclosed herein can be used for retrieval and analysis of trace amounts of drug and explosive residues. The system described herein has been used in the areas of trace and document analysis within the forensic field, trace fiber analysis, and electrostatic lifts for illicit drugs, as well as document and painting analysis.

25 Claims, 36 Drawing Sheets

(56) References Cited

U.S. PATENT DOCUMENTS

| | | | |
|---|---|---|---|
| 2003/0068653 A1 | 4/2003 | Parrott | |
| 2004/0238736 A1 | 12/2004 | Nilsson et al. | |
| 2006/0128950 A1 | 6/2006 | Jordan et al. | |
| 2006/0234298 A1* | 10/2006 | Chiu et al. | 435/7.1 |
| 2007/0207504 A1 | 9/2007 | Gimble et al. | |
| 2008/0067079 A1* | 3/2008 | Takahashi et al. | 205/775 |
| 2008/0067352 A1 | 3/2008 | Wang | |
| 2008/0149822 A1 | 6/2008 | Vertes et al. | |
| 2009/0078063 A1* | 3/2009 | Zhang et al. | 73/864 |
| 2009/0134323 A1 | 5/2009 | Gross et al. | |
| 2009/0200678 A1* | 8/2009 | Kim et al. | 257/761 |
| 2009/0238726 A1 | 9/2009 | Gentle et al. | |
| 2009/0261244 A1 | 10/2009 | Syms | |
| 2009/0272893 A1* | 11/2009 | Hieftje et al. | 250/282 |
| 2010/0000338 A1 | 1/2010 | Van Berkel | |
| 2010/0048492 A1 | 2/2010 | Quesniaux Ryffel et al. | |
| 2010/0258717 A1 | 10/2010 | Chen et al. | |
| 2010/0328657 A1* | 12/2010 | Dholakia et al. | 356/301 |
| 2011/0003066 A1 | 1/2011 | Knowlton et al. | |
| 2011/0132108 A1* | 6/2011 | Novosselov et al. | 73/863.22 |
| 2011/0133077 A1 | 6/2011 | Henion et al. | |
| 2011/0198495 A1 | 8/2011 | Hiraoka | |
| 2011/0207227 A1 | 8/2011 | Menzel et al. | |
| 2011/0220784 A1* | 9/2011 | Roach et al. | 250/282 |
| 2011/0266429 A1 | 11/2011 | Vestel et al. | |

OTHER PUBLICATIONS

Craig et al, "Evaluation and Comparison of the Electrostatic Dust Print Lifter and the Electrostatic Detection Apparatus on the Development of Footwear Impressions on Paper", J Forensic Sci, Jul. 2006, vol. 51, No. 4 p. 819-826.*

Craig (Craig et al, "Evaluation and Comparison of the Electrostatic Dust Print Lifter and the Electrostatic Detection Apparatus on the Development of Footwear Impressions on Paper", J Forensic Sci, Jul. 2006, vol. 51, No. 4 p. 819-826).*

Yumusova, S.G. et al. "A Mass-Spectrometric Study of the Hydroxy Acids of Cottonseed Oil" Chemistry of Natural Compounds, Jul.-Aug. 1981, vol. 17, Issue 4, pp. 320-325.

Asano, Keiji G., et al., "Self-Aspirating Atmospheric Pressure Chemical Ionization Source for Direct Sampling of Analytes on Surfaces and in Liquid Solutions," Rapid Commun. Mass Spectrom, (2005), 19:2305-2312.

Bligh, E.G., et al., "A Rapid Method of Total Lipid Extraction and Purification," Can. J. Biochem. Physiol., (1959) 37:911-917.

Cech, Nadja B., et al., "Practical Implications of Some Recent Studies in Electrospray Ionization Fundamentals," Mass Spectrometry Reviews, (2001), pp. 362-387.

Cooks, et al., "Ambient Mass Spectrometry," Science, (2006), 311(5767):1566-1570.

Croxton, et al., "Development of a GC-MS Method for the Simultaneous Analysis of Latent Fingerprint Components," Journal of Forensic Sciences, vol. 51, Issue 6, Nov. 2006, pp. 1329-1333.

Grant, Ashleigh, et al., "Identification of Recently Handled Materials by Analysis of Latent Human Fingerprints Using Infared Spectromicroscopy," Applies Spectromicroscopy, vol. 59, No. 9, (2005), pp. 1182-1187.

Rice, N. M., et al., "Nomenclature for Liquid-Liquid Distribution (Solvent Extraction)," Pure and Appl. Chem., (1993), vol. 65, No. 11, pp. 2373-2396.

Justes, Dina R., et al., "Detection of Explosives on Skin Using Ambient Ionization Mass Spectrometry," Chem. Commun., (2007), pp. 2142-2144.

Kajiyama, Shin'ichiro, et al., "Single Cell-Based Analysis of Torenia Petal Pigments by a Combination of ArF Excimer Laser Micro Sampling and Nano-High Performance Liquid Chromatography (HPLC)—Mass Spectrometry," Journal of Bioscience and Bioengineering, (2006), vol. 102, No. 6, pp. 575-578.

Li, et al., "Nanoliter Solvent Extraction Combines with Microspot MALDI TOF Mass Spectrometry for the Analysis of Hydrophobic Biomolecules," Anal. Chem., (2001) pp. 2929-2936.

Lisa, Miroslav, et al., "Triacylglycerols Profiling in Plant Oils Important in Food Industry, Dietetics and Cosmetics Using High-Performance Liquid Chromatography-Atmospheric Pressure Chemical Ionization Mass Spectrometry," Journal of Chromatography A, (2008), pp. 115-130.

Liu, Hanghui, et al., "Analytical Chemistry in a Drop, Solvent Extraction in a Microdrop," Anal. Chem., (1996), 68, 1817.

Lloyd, et al., "One-Pot Processing of Swabs for Organic Explosives and Firearms Residue Traces," Journal of Forensic Sciences, vol. 35, Issue 4, Jul. 1990, pp. 956-959.

Marshall, et al., "Aspects of Explosives Detection," 1st Edition, Elsevier, (2009), 303 pages.

Na, Na. et al., "Development of a Dielectric Barrier Discharge Ion Source for Ambient Mass Spectrometry," American Society for Mass Spectrometry, (2007), pp. 1859-1862.

Schumaker, Verne, "Cholesterolemic Rabbit Lipoproteins: Serum Lipoproteins of the Cholesterolemic Rabbit," Am. J. Physiol., (1955) pp. 35-42.

Sitti, Metin, et al., "Survey of Nanomanipulation Systems," Nanotechnology, (2001), IEEE-NANO 2001, pp.

Takats, Zoltan, et al., "Direct, Trace Level Detection of Explosives on Ambient Surfaces by Desorption Electospray Ionization Mass Spectrometry," Chem. Commun., (2005), pp. 1950-1952.

Van Berkel, Gary, J., et al., "Liquid Microjunction Surface Sampling Probe Electrospray Mass Spectrometry for Detection of Drugs and Metabolites in Thin Tissue Sections," Journal of Mass Spectrometry, (2008), vol. 43, pp. 500-508.

\* cited by examiner

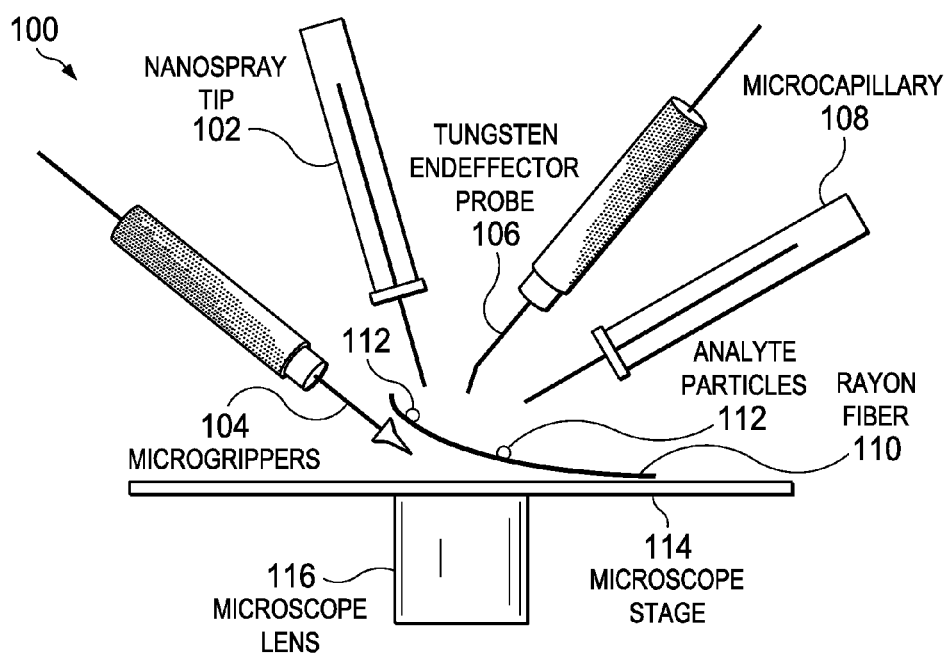
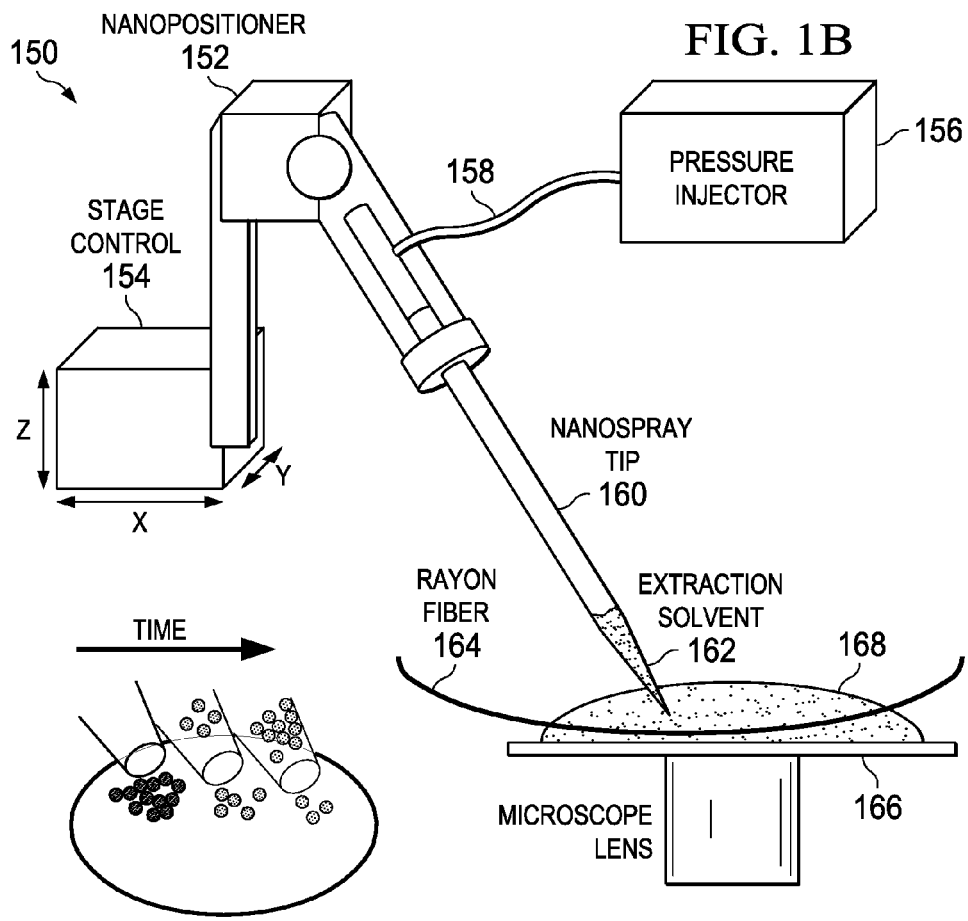

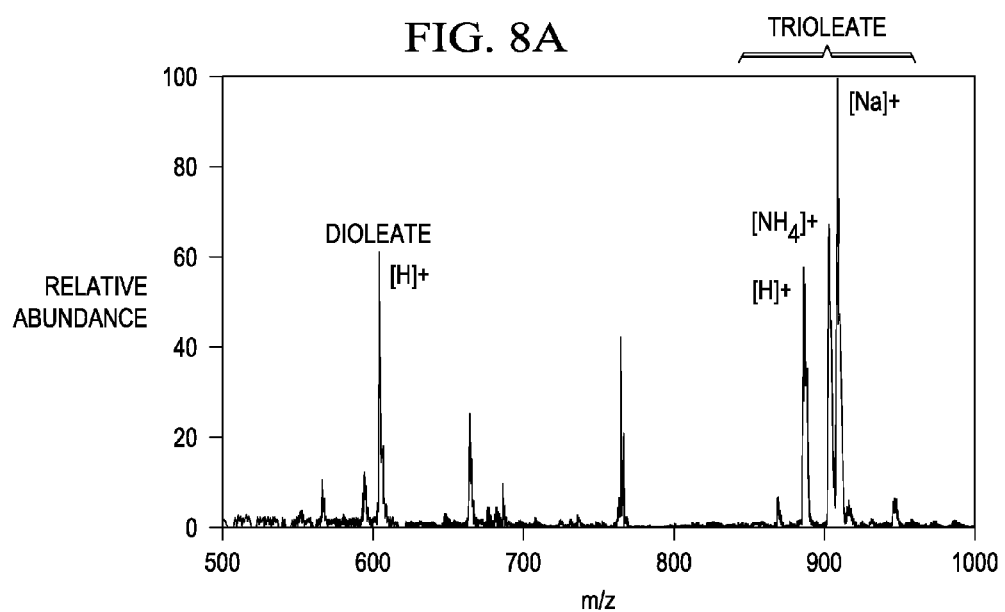
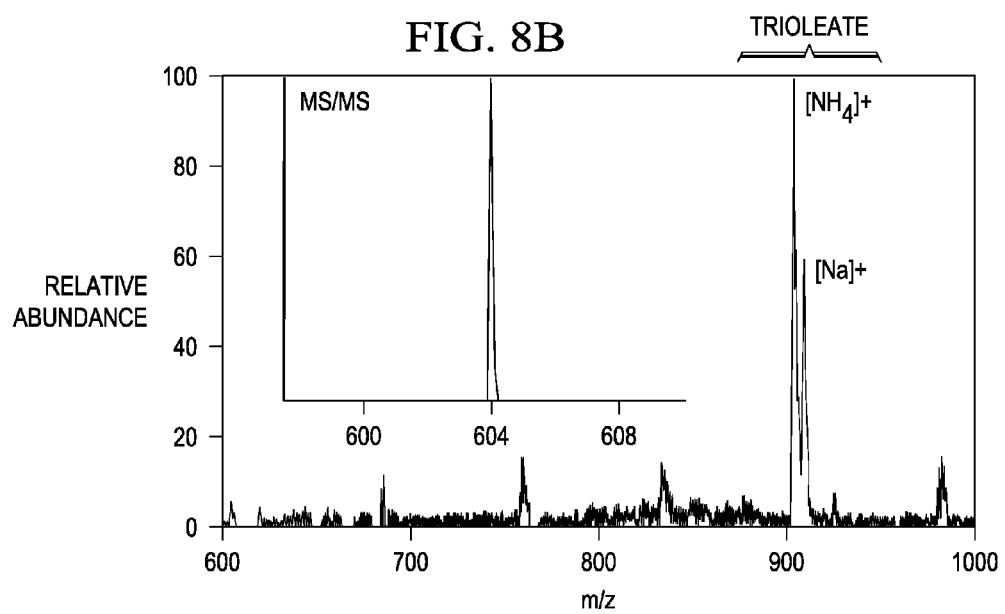

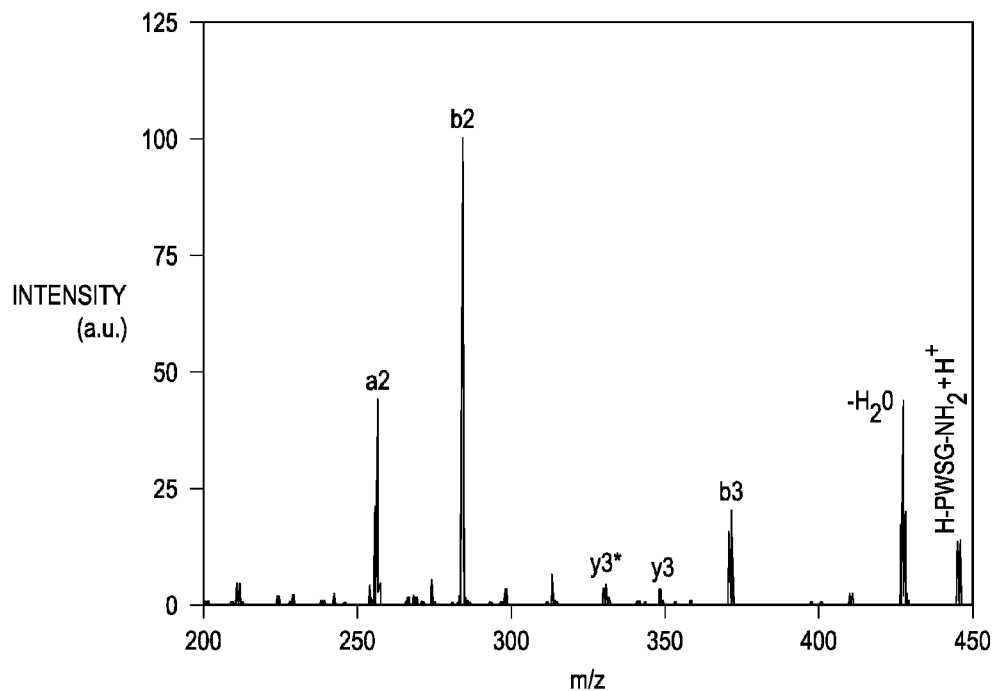
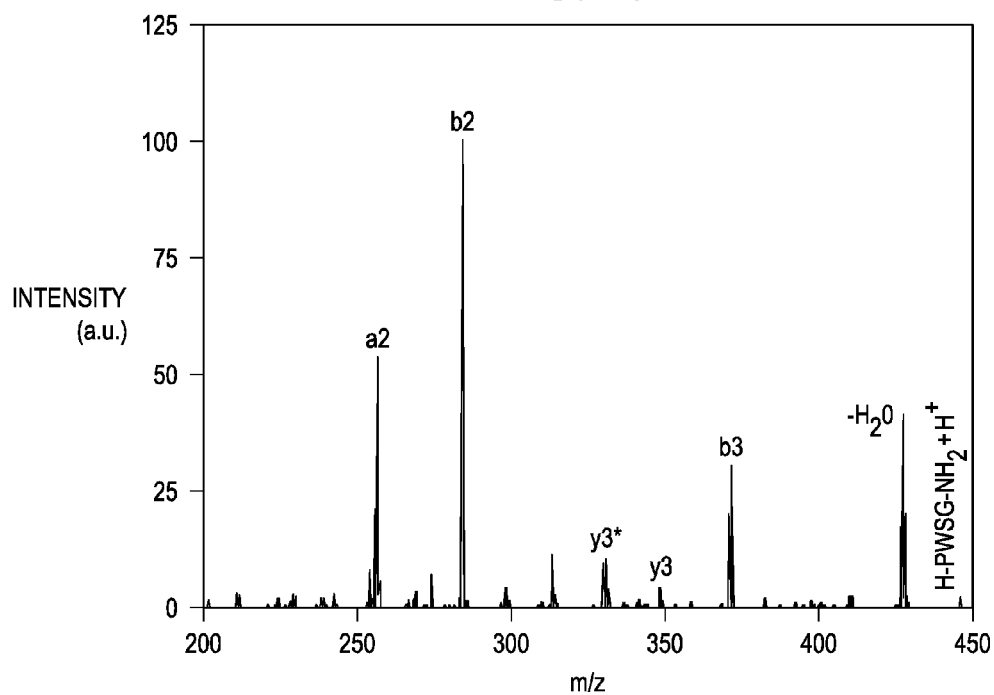

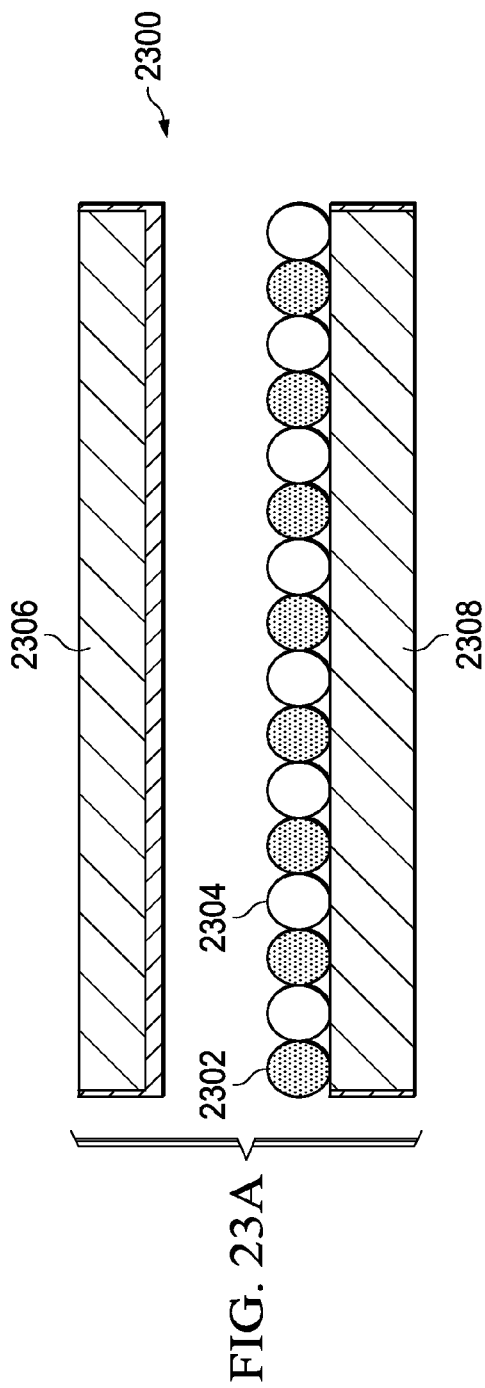
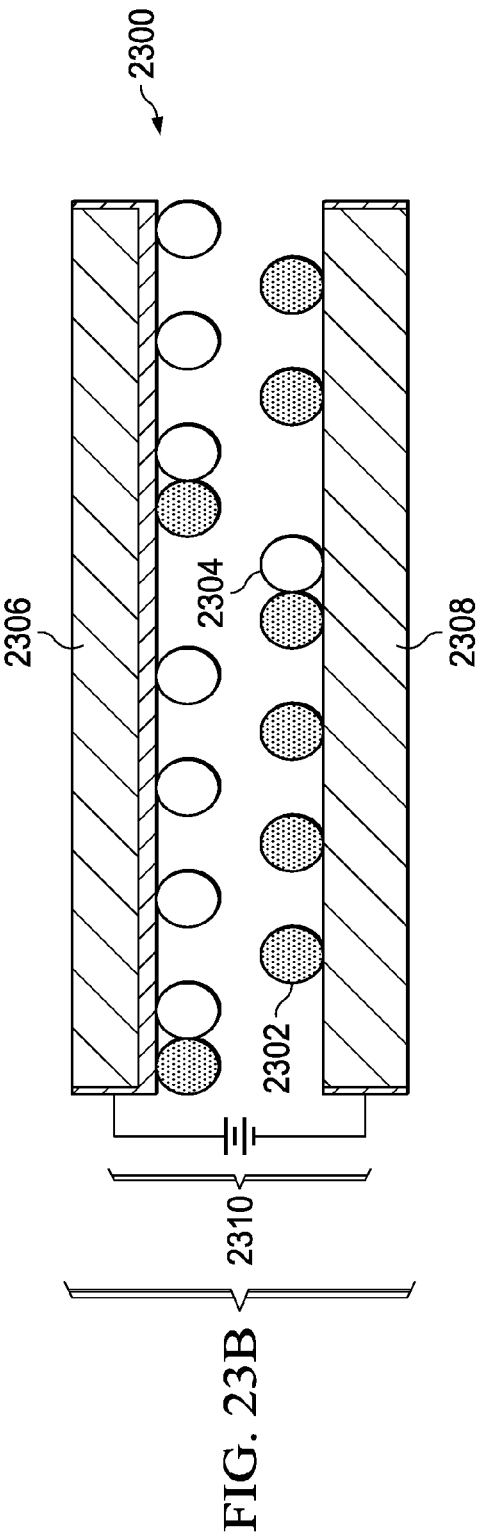

3002

3002

3002

3006

NANOMANIPULATION COUPLED NANOSPRAY MASS SPECTROMETRY (NMS)

CROSS-REFERENCE TO RELATED APPLICATIONS

This application is a non-provisional application of U.S. Provisional Patent Application No. 61/391,842 filed on Oct. 11, 2010, and entitled "Nanomanipulation Coupled Nanospray Mass Spectrometry (NMS)" and is a Divisional Application of co-pending U.S. patent application Ser. No. 13/270,962 filed on Oct. 11, 2011 which are hereby incorporated by reference in their entirety.

TECHNICAL FIELD OF THE INVENTION

The present invention relates in general to the field of mass spectrometry (MS), and more particularly to a technique for single cell, single organelle, and ultra-trace molecular analysis using nanomanipulation coupled with nanospray mass spectrometry (NMS).

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in connection with mass spectrometry techniques and methods.

U.S. Patent Application Publication No. 2009/0261244 (Syms, 2009) provides a method of aligning a nanospray capillary needle, a set of electrodes, and a capillary input to a mass spectrometer. The electrode system is formed using microengineering technologies, as an assembly of two separate chips. Each chip is formed on an insulating plastic substrate. The first chip carries mechanical alignment features for the capillary electrospray needle and the API mass spectrometer input, together with a set of partial electrodes. The second chip carries a set of partial electrodes. The complete electrode system is formed when the chips are assembled in a stacked configuration, and consists of an einzel lens capable of initiating a Taylor cone and separating ions from neutrals by focusing.

U.S. Pat. No. 7,385,189 (Goodley et al. 2008) provides an apparatus and method for use with a mass spectrometry system. The invention provides an ion source for providing radiative heating to an ionization region. The ion source includes a nanospray ionization device for producing ions and a conduit adjacent to the ionization device for receiving ions from the ionization device. The conduit includes a conductive material for providing indirect radiative heating to the ionization region. Direct radiative heating may also be provided using a heater in the conduit. The ion source may be used separately or in conjunction with the mass spectrometry system. When used in conjunction with a mass spectrometry system a detector may also be employed down stream from the device. A method for desolvating an analyte using the device is also disclosed.

U.S. Pat. No. 6,812,460 (Stallcup and Baur, 2004) discloses a method of nanomanipulation, including providing a nano-scale object movably positioned over a substrate and positioning a probe of a scanning probe microscope proximate the nano-scale object. The probe is then moved across the substrate along a gyrating path proximate the nano-scale object to reposition the nano-scale object.

SUMMARY OF THE INVENTION

The present invention describes a technique that combines nanomanipulation and nanospray mass spectrometry (NMS) for the analysis of a single cell, a single organelle, and ultra-trace amounts of one or more molecules.

The present invention in one embodiment provides a method for identifying, detecting, analyzing or combinations thereof of one or more analytes from a substrate comprising the steps of: (i) providing the substrate comprising the one or more analytes to be detected, wherein the substrate is mounted directly or indirectly on an inverted microscopic stage, (ii) providing an extraction system for an extraction of the one or more analytes from the substrate followed by a transfer to a detection system, wherein the detection system is coupled to the extraction system, wherein the extraction system comprises: a) a workstation comprising a plurality of moveable nanopositioners, wherein the nanopositioners are capable of movement in a X-Y-Z plane, wherein the nanopositioners hold one or more probes, grippers, capillary tips or any suitable accessory for an extraction and transfer of a liquid phase, b) a pressure injector for delivery of a pressurized extraction solvent through the capillary tip, wherein the capillary tip is placed in close proximity to the substrate, c) a voltage source, d) a joystick or a digital controller for controlling the movement of the nanopositioners, and e) a mass spectrometer that is offline or is connected to the extraction system for receiving the one or more dissolved analytes transferred by the extraction system, (iii) dissolving the one or more analytes by an injection of the extraction solvent onto the substrate, (iv) aspirating the dissolved analytes by the one or more capillary tips, (v) injecting the aspirated analytes into the mass spectrometer to obtain a mass spectrum, and (vi) identifying the one or more analytes by a m/z ratio in the mass spectrum. Additionally, the method further comprises the step of determining a concentration of the one or more analytes in the substrate.

In one aspect of the method disclosed hereinabove the one or more analytes are selected from the group consisting of industrial, chemical, and biological materials, biological cells, paints, inks, pigments, dyes, illicit drugs, pharmaceuticals, proteins, and combinations and modifications thereof. In another aspect the substrate is selected from the group consisting of fibers, clothing, hair, paper, money, computer chips, treated wood, laminate, metal, manipulated surfaces including mylar electrostatic lift films, plastic, and combinations and modifications thereof. In a specific aspect of the method the mass spectrometer is equipped with a nanospray source. In another aspect the substrate is mounted on a non-inverted microscopic stage.

In another aspect the method is used for analysis of documents, analysis of artworks, illicit drug detection, forensic and toxicology studies, and combinations and modifications thereof. In yet another aspect the extraction solvent comprises water, polar organic and inorganic solvents, mixtures of polar and non-polar solvents, and combinations and modifications thereof.

In another embodiment the instant invention discloses a system for identifying, detecting, analyzing or combinations thereof of one or more analytes from a substrate comprising: an inverted or non-inverted microscopic stage capable of holding the substrate comprising the one or more analytes, a workstation comprising a plurality of moveable nanopositioners, wherein the nanopositioners are capable of movement in a X-Y-Z plane, wherein the nanopositioners hold one or more probes, grippers, capillary tips or any suitable accessory for an extraction and transfer of a liquid phase, a pressure injector for delivery of a pressurized extraction solvent through the capillary tip, wherein the capillary tip is placed in close proximity to the substrate, a voltage source, a joystick or a digital controller for controlling the movement of the nanopositioners, and a mass spectrometer that is offline or is connected to the extraction system for receiving the one or more dissolved analytes transferred by the extraction system and for identifying the one or more analytes by a m/z ratio from a generated mass spectrum. The system disclosed above further comprises the step of determining a concentration of the one or more analytes in the substrate. In one aspect the one or more analytes are selected from the group consisting of industrial, chemical, and biological materials, cells, organelles, paints, inks, pigments, dyes, illicit drugs, pharmaceuticals, proteins, and combinations and modifications thereof.

In specific aspects the illicit drug is cocaine, the organelle is mitochondria and the substrate is selected from the group consisting of fibers, clothing, hair, paper, money, computer chips, treated wood, laminate, metal, manipulated surfaces including mylar electrostatic lift films, plastic, and combinations and modifications thereof. In a related aspect the mass spectrometer is equipped with a nanospray source. In another aspect the system is used for analysis of documents, analysis of artworks, illicit drug detection, forensic and toxicology studies, and combinations and modifications thereof. In yet another aspect the extraction solvent comprises water, polar organic and inorganic solvents, mixtures of polar and non-polar solvents, and combinations and modifications thereof. It will be understood that addition of significant acid/base chemistry to the extraction solvent can modify the ionization process.

Yet another embodiment of the instant invention relates to a method for compositional analysis, concentrating one or more analytes or combinations thereof comprising the steps of: a) providing the one or more analytes in a first liquid phase mounted directly or indirectly on an inverted microscopic stage, b) providing an extraction system for an extraction of the one or more analytes from the substrate followed by a transfer to a detection system, wherein the detection system is coupled to the extraction system, wherein the extraction system comprises: (i) a workstation comprising a plurality of moveable nanopositioners, wherein the nanopositioners are capable of movement in a X-Y-Z plane, wherein the nanopositioners hold one or more probes, grippers, capillary tips or any suitable accessory for an extraction and transfer of a liquid phase, (ii) a pressure injector for delivery of a pressurized extraction solvent through the capillary tip, wherein the capillary tip is placed in close proximity to the substrate, wherein the extraction solvent is immiscible or partially miscible with the first liquid phase, (iii) a voltage source, (iv) a joystick or a digital controller for controlling the movement of the nanopositioners, and (v) a mass spectrometer connected to the extraction system (online) or not directly connected to the extraction system (offline) for receiving the one or more analytes transferred by the extraction system, c) solubilizing or partitioning the one or more analytes between the first phase and the extraction solvent by an injection of the extraction solvent onto the substrate, d) aspirating a mixture of the solubilized or partitioned analytes by the one or more capillary tips, e) mixing the aspirated mixture by a movement of the mixture in the capillary tube, f) injecting the aspirated analytes into the mass spectrometer to obtain a mass spectrum, and g) identifying the one or more analytes by a m/z ratio in the mass spectrum. The method as disclosed herein further comprises the step of determining a concentration of the one or more analytes in the substrate. In one aspect the step of determining the concentration is done by an injection of an internal standard, wherein the internal standard is a pure sample or a derivative of the analyte having a similar mass. In another aspect the one or more analytes are selected from the group consisting of biomolecules, lipophilic compounds, oils, triacylglycerols, vegetable oil products, cottonseed oil, serum, proteins, antibodies, and combinations and modifications thereof. In specific aspects the analyte is cottonseed oil or rabbit serum.

In another aspect the mass spectrometer is equipped with a nanospray source. In yet another aspect the extraction solvent comprises water, polar organic and non-polar organic solvents, mixtures of polar and non-polar solvents, and combinations and modifications thereof. It will be understood that addition of significant acid/base chemistry to the extraction solvent can modify the ionization process. In another aspect a non-limiting example of an extraction solvent is a 1:1 mixture of chloroform and methanol, comprising about 2% acetic acid. It will be understood by the skilled artisan that the choice of a solvent will depend on the system to be extracted.

In one embodiment the present invention relates to a system for compositional analysis, concentrating one or more analytes or combinations thereof of one or more analytes from a substrate comprising: an inverted microscopic stage mounted with or capable of holding the one or more analytes in a first liquid phase, an extraction system for an extraction of the one or more analytes from the substrate followed by a transfer to a detection system, wherein the detection system is coupled to the extraction system, wherein the extraction system comprises: a workstation comprising a plurality of moveable nanopositioners, wherein the nanopositioners are capable of movement in a X-Y-Z plane, wherein the nanopositioners hold one or more probes, grippers, capillary tips or any suitable accessory for an extraction and transfer of a liquid phase, a pressure injector for delivery of a pressurized extraction solvent through the capillary tip, wherein the capillary tip is placed in close proximity to the substrate, wherein the extraction solvent is immiscible or partially miscible with the first liquid phase, a voltage source, a joystick or a digital controller for controlling the movement of the nanopositioners, and a mass spectrometer connected to the extraction system for receiving the one or more analytes transferred by the extraction system. In one aspect the system can be used to determine a concentration of the one or more analytes in the substrate. In another aspect the step of determining the concentration is done by an injection of an internal standard, wherein the internal standard is a pure sample or a derivative of the analyte having a similar mass. In another aspect the one or more analytes are selected from the group consisting of biomolecules, lipophilic compounds, oils, triacylglycerols, vegetable oil products, cottonseed oil, serum, proteins, antibodies, and combinations and modifications thereof.

In specific aspects the analyte is cottonseed oil or rabbit serum and the mass spectrometer is equipped with a nanospray source. In another aspect the extraction solvent comprises water, polar organic and non-polar organic solvents, mixtures of polar and non-polar solvents, and combinations and modifications thereof. In another aspect the extraction solvent is a 1:1 mixture of chloroform and methanol, comprising about 2% acetic acid.

The present invention in one embodiment describes a fingerprint lift method for detecting trace amounts of one or more analytes from a solid substrate comprising the steps of: providing a cast, a mould or any other solid impression of a human finger, wherein the cast or the mould comprises one or more ridges duplicating the ridges found on the human finger, saturating the cast, the mould or the solid impression with an oil, a grease or a lipid by a spraying, a dipping or a coating process, lifting the analytes from the solid substrate by pressing or contacting the cast, the mould or the solid impression with the substrate, transferring the lifted analytes from the solid substrate to a microscopic slide or any other suitable solid support, and detecting the one or more analytes by generating a mass spectrum in a mass spectrometer, wherein the detection is done by identifying a m/z ratio of the analytes in the mass spectrum.

In one aspect the one or more analytes comprise explosives, drugs, and narcotics. In another aspect the analyte is cocaine. In another aspect the analyte is nitroglycerine (NG) and dinitrotoluene (DNT). It will be understood by a person skilled in the art that the technique of the present invention can be applied to literally hundreds of energetic materials. In yet another aspect the mass spectrometer system is equipped with a nanospray source. The system as described in the method of the present invention comprises: a) an inverted microscopic stage mounted with or capable of holding the solid support comprising the one or more analytes, b) an extraction system for an extraction of the one or more analytes from the support followed by a transfer to a detection system, wherein the detection system is coupled to the extraction system, wherein the extraction system comprises: (i) a workstation comprising a plurality of moveable nanopositioners, wherein the nanopositioners are capable of movement in a X-Y-Z plane, wherein the nanopositioners hold one or more probes, grippers, capillary tips or any suitable accessory for an extraction and transfer of a liquid phase, (ii) a pressure injector for delivery of a pressurized extraction solvent through the capillary tip, wherein the capillary tip is placed in close proximity to the support, (iii) a voltage source, (iv) a joystick or a digital controller for controlling the movement of the nanopositioners, and (v) a mass spectrometer connected to the extraction system for receiving the one or more analytes transferred by the extraction system. In another aspect the method further comprises the step of generating a background mass spectrum comprising any other analytes that may be expected to be present, the oil, the grease or the lipids or both, wherein the background spectrum is used to correct for interferences from the other analytes, the oil, the grease or the lipids or both.

Yet another embodiment describes a fingerprint lift method for detecting trace amounts of one or more dissolved analytes from a liquid comprising the steps of: (i) evaporating the liquid to obtain a solid residue, wherein the solid residue comprises the one or more analytes to be detected, (ii) providing a cast, a mould or any other solid impression of a human finger, wherein the cast or the mould comprises one or more ridges duplicating the ridges found on the human finger, (iii) saturating the cast, the mould or the solid impression with an oil, a grease or a lipid by a spraying, a dipping or a coating process, (iv) lifting the analytes from the solid residue by pressing or contacting the cast, the mould or the solid impression with the residue, (v) transferring the lifted analytes from the solid residue to a microscopic slide or any other suitable solid support, and (vi) detecting the one or more analytes by generating a mass spectrum in a mass spectrometer, wherein the detection is done by identifying a m/z ratio of the analytes in the mass spectrum.

In one aspect the one or more analytes comprise explosives, drugs, and narcotics. In another aspect the analyte is cocaine. In another aspect the analyte is nitroglycerine (NG) and dinitrotoluene (DNT). It will be understood by a person skilled in the art that the technique of the present invention can be applied to literally hundreds of energetic materials. In yet another aspect the mass spectrometer system is equipped with a nanospray source, wherein the system comprises: (i) an inverted microscopic stage mounted with or capable of holding the solid support comprising the one or more analyses, and (ii) an extraction system for an extraction of the one or more analytes from the support followed by a transfer to a detection system, wherein the detection system is coupled to the extraction system, wherein the extraction system comprises: a workstation comprising a plurality of moveable nanopositioners, wherein the nanopositioners are capable of movement in a X-Y-Z plane, wherein the nanopositioners hold one or more probes, grippers, capillary tips or any suitable accessory for an extraction and transfer of a liquid phase, a pressure injector for delivery of a pressurized extraction solvent through the capillary tip, wherein the capillary tip is placed in close proximity to the support, a voltage source, a joystick or a digital controller for controlling the movement of the nanopositioners, and a mass spectrometer connected to the extraction system for receiving the one or more analytes transferred by the extraction system. In yet another aspect the extraction solvent comprises water, polar organic and inorganic solvents, mixtures of polar and non-polar solvents, and combinations and modifications thereof. In yet another aspect the method further comprises the step of generating a background mass spectrum comprising any other analytes that may be expected to be present, the oil, the grease or the lipids or both, wherein the background spectrum is used to correct for interferences from the other analytes, the oil, the grease or the lipids or both.

In one embodiment the instant invention discloses a method for lifting prints, detecting one or more analytes, drug residues, or contaminants in a mixture, or any combinations thereof comprising the steps of: (i) placing a substrate or a film on top of and in contact with the print, the one or more analytes, drug residues, or contaminants in a mixture, or any combinations thereof, wherein the substrate or film comprises a metal coated surface and (ii) applying a voltage to the substrate or the film, wherein the application of the voltage results in a lifting, a retrieval or an adhesion of the print, the one or more analytes, drug residues, contaminants in a mixture, or any combinations thereof due to a combination of electrostatic and conductive forces. The method as described hereinabove further comprises the step of detecting the one or more analytes, the drug residues, contaminants in a mixture, or any combinations thereof by Raman spectroscopy or by generation of a mass spectrum in a mass spectrometer, wherein the detection is done by identifying a m/z ratio of the analytes in the mass spectrum. In one aspect the step of detection is performed by Surface Enhanced Raman Scattering (SERS). In another aspect the step of detection is performed by a mass spectrometer system equipped with a nanospray source. In yet another aspect the one or more analytes comprise explosives, drugs, narcotics, or any combinations thereof wherein the drugs are selected from the group consisting of cocaine, amphetamines, codeine, hydrocodone, and crystal meth. In other related aspects the substrate or the film comprises a polymer, a polyester, or any conductive material capable of lifting the one or more analytes from a surface and the film coating comprises metals selected from gold, silver, or any combinations thereof, wherein the metals are deposited by physical vapor deposition.

Another embodiment of the instant invention disclosed herein provides a method for lifting prints, detecting one or more analytes, drug residues, or contaminants in a mixture, or any combinations thereof comprising the steps of: i) placing an uncoated first substrate or a first film on top of and in contact with the print, the one or more analytes, drug residues, contaminants in a mixture, or any combinations thereof, wherein the analyte, the drug residue, contaminants in the mixture, or any combinations thereof adhere to and are collected onto the surface of the first substrate; ii) placing a coated second substrate or a second film on top of and in contact with the first substrate or first film comprising the collected one or more analytes, drug residues, contaminants in a mixture, or any combinations thereof, wherein the second substrate or the second film is a metal coated film; and iii) applying a voltage to the second substrate or the film, wherein the application of the voltage results in a lifting, a retrieval or an adhesion of the print, the one or more analytes, drug residues, contaminants in a mixture, or any combinations thereof due to a combination of electrostatic and conductive forces. In one aspect the step of detecting the one or more analytes, the drug residues, contaminants in a mixture, or any combinations thereof by Raman spectroscopy or by generation of a mass spectrum in a mass spectrometer, wherein the detection is done by identifying a m/z ratio of the analytes in the mass spectrum. In another aspect the one or more analytes comprise explosives, drugs, narcotics, or any combinations thereof wherein the drugs are selected from the group consisting of cocaine, amphetamines, codeine, hydrocodone, and crystal meth. In yet another aspect the substrate or the film comprises a polymer, a polyester, or any conductive material capable of lifting the one or more analytes from a surface. In a related aspect the film coating comprises metals selected from gold, silver, or any combinations thereof, wherein the metals are deposited by physical vapor deposition. In a specific aspect second substrate or film is coated with gold. In other aspects the first substrate or film and the second substrate or film may comprise same or different materials and a thickness of the metal coated films ranges from 25 nm-100 nm.

In yet another embodiment the present invention provides a method for identifying lipid components, determining lipid profiles, detecting relative amounts of different lipids, or any combinations thereof from a lipid storing substrate, body, tissue, cell, organelle, lipid droplets (LDs) or any combinations thereof comprising the steps of: i) providing a sample comprising the one or more lipid containing substrates, bodies, tissues, cells, organelles, LDs, or any combinations thereof; ii) providing an extraction system for an extraction of the one or more lipids from the lipid containing tissue, cell, organelle, lipid droplets (LDs) or any combinations thereof followed by a transfer to a detection system, wherein the detection system may be coupled to the extraction system; iii) dissolving the one or more lipids by an injection of the extraction solvent onto the substrate; iv) aspirating the dissolved lipids by the one or more capillary tips; v) injecting the aspirated lipids into the mass spectrometer to obtain a mass spectrum; and vi) identifying the one or more lipids by a m/z ratio in the mass spectrum.

The extraction system as described hereinabove comprises:
a) a workstation comprising a plurality of moveable nanopositioners, wherein the nanopositioners are capable of movement in a X-Y-Z plane, wherein the nanopositioners hold one or more probes, grippers, capillary tips or any other suitable accessory for an extraction and transfer of a liquid phase;
b) a pressure injector for a delivery of a pressurized extraction solvent through the capillary tip, wherein the capillary tip is placed in close proximity to the lipid containing substrates, bodies, tissues, cells, organelles, LDs, or any combinations thereof;
c) a voltage source;
d) a joystick or a digital controller for controlling the movement of the nanopositioners; and
e) a mass spectrometer that is off line or is connected to the extraction system for receiving the one or more dissolved analytes transferred by the extraction system.

The method as described hereinabove further comprises the steps of: i) determining a lipid profile from an extract of lipids or one or more lipid standards; and ii) comparing the identified lipids from the sample with the lipid profile from the extract of lipids or the lipid standards to determine the lipid profile of the sample, the relative amounts of the lipids in the sample, or any combinations thereof. In a specific aspect the mass spectrometer is equipped with a nanospray source and the substrate is mounted on an inverted microscopic stage. In another aspect the extraction solvent comprises water, polar organic and inorganic solvents, mixtures of polar and non-polar solvents, and combinations and modifications thereof. In yet another aspect the extraction solvent comprises 10 mM ammonium acetate in chloroform:methanol (1:1, v/v). In another aspect the lipids comprise triacylglycerol (TAG), monoglycerides, diglycerides, triglycerides, lipid derivatives like fatty acid methyl esters (FAME), or any combinations thereof. In another aspect the method described herein further comprises the optional step of isolating and purifying the lipid containing substrate, body, tissue, cell, organelle, LDs, or any combinations thereof.

In one embodiment the present invention relates to a method for identifying lipids, determining lipid content, profile, or both or any combinations thereof in a single-lipid droplet (LD) or directly from a lipid containing organelle comprising the steps of: i) providing one or more isolated and purified LDs or lipid containing organelle, wherein the LDs or the lipid containing organelle are obtained from a plant or an animal source; ii) providing an extraction system for an extraction of the LDs or the lipid containing organelle, followed by a transfer to a detection system, wherein the detection system may be coupled to the extraction system, wherein the extraction system comprises: a) a workstation comprising a plurality of moveable nanopositioners, wherein the nanopositioners are capable of movement in a X-Y-Z plane, wherein the nanopositioners hold one or more probes, grippers, capillary tips or any other suitable accessory for an extraction and transfer of a liquid phase; b) a pressure injector for a delivery of a pressurized extraction solvent through the capillary tip, wherein the capillary tip is placed in close proximity to the LDs or the lipid containing organelle, wherein the extraction solvent comprises 10 mM ammonium acetate in chloroform:methanol (1:1, v/v) spiked with a Tri 15:0 triacylglycerol (TAG) standard; c) a voltage source; d) a joystick or a digital controller for controlling the movement of the nanopositioners; and e) a mass spectrometer that is off line or is connected to the extraction system for receiving the one or more LDs or the lipid containing organelle transferred by the extraction system; iii) aspirating the LDs or the lipid containing organelle in the extraction solvent by the one or more capillary tips; iv) injecting the aspirated LDs or the lipid containing organelle into the mass spectrometer to obtain a mass spectrum; and v) identifying the one or more lipids by a m/z ratio in the mass spectrum.

The method of the present invention further comprises the steps of: determining a lipid profile from an extract of lipids or one or more lipid standards and comparing the lipids from the LDs or the lipid containing organelle with the lipid profile from the extract of lipids or the lipid standards to determine the lipid profile of the sample, the relative amounts of the lipids in the sample, or any combinations thereof. In one aspect the mass spectrometer is equipped with a nanospray source. In another aspect the detection system may comprise a Raman spectrometer. In yet another aspect the LDs or the lipid containing organelles may be stained using a lipid based dye or an imaging agent.

BRIEF DESCRIPTION OF THE DRAWINGS

For a more complete understanding of the features and advantages of the present invention, reference is now made to the detailed description of the invention along with the accompanying figures and in which:

FIG. 1A is a schematic of the nanomanipulator workstation. Two nanopositioners are capable of holding capillary tips used for nanospray ionization. The remaining two positioners utilize end-effectors (either tungsten probes or microgrippers) for sample manipulation;

FIG. 1B is a schematic of a nanopositoner holding a capillary tip for nanospray ionization. Here the extraction solvent is shown on the rayon fiber. A time-resolved schematic shows the retrieval of analyte particles into the tip;

FIGS. 6A-6C demonstrate the accumulation of BODIPY in the nanospray capillary extracted with chloroform while the aqueous solution simultaneously fades at: (FIG. 6A) ~0 minutes, (FIG. 6B) ~10 minutes, (FIG. 6C) ~25 minutes;

FIG. 8A shows the acid-catalyzed hydrolysis of trioleate with a [H]+ adduct at 885.5 m/z, [NH$_4$]+ adduct at 903.0 m/z, and [Na]+ adduct at 908.0 m/z by LPME-NMS with 1:1 (v/v);

FIG. 8B shows that the diacylglycerol fragment was effectively minimized by substituting 10 mM ammonium acetate in place of the glacial acetic acid. MS/MS (inset) of trioleate confirmed the characteristic diacylglycerol fragment at 603.5 m/z;

(FIG. 13A) caffeine extraction with nanomanipulator, (FIG. 13B) NSI-MS spectrum of caffeine. MH$^+$ peak is seen at m/z 195.00, (FIG. 13C) ESI-MS spectrum of cocaine wash from electrostatic lift. WI$^+$ peak is seen at m/z 304.73, (FIG. 13D) NSI-MS spectrum of cocaine extraction from electrostatic lift. MH$^+$ peak is seen at m/z 304.13;

FIG. 18A is an ESI MS/MS spectrum of H-PWSG-NH$_2$;

FIG. 18B is a NSI MS/MS spectrum of H-PWSG-NH$_2$;

FIGS. 23A and 23B are schematic diagrams of a two-step lifting process where, FIG. 23A is a primary lift containing both analyte (white) and matrix (gray) particles is covered with a gold-coated film and FIG. 23B is a secondary lift is performed to collect the analyte particles for SERS analysis, leaving the primary lift intact;

(FIG. 31A) the nanopositioner, set on an inverted microscope stage, electronically controls the x, y, and z positioning of a nanospray emitter through a user-operated joystick. The nanospray emitter is prefilled with a microextraction solvent and is directly connected to a pressure injector. Approaching purified LDs in buffer, the emitters can selectively load LDs of interest, microextract their lipid contents, and analyze their compositions by nanospray mass spectrometry, (FIG. 31B) Scale bar represents 2 µm;

(FIG. 32A) representative positive ion, high resolution TAG profile of purified LDs from mature cotton embryos (cv. Coker 312). Dominant TAG species are identified as ammonium adducts $[M+NH4]^+$ with peaks labeled according to the three fatty acids present in each TAG molecular species as identified through subsequent tandem MS analysis by collision induced dissociation (CID), (FIG. 32B) schematic of tandem MS of a TAG with acyl chains R1, R2, R3. Fragmentation of the R1 ester bond (blue line) produces a corresponding DAG plus hydrogen adduct (blue, R2 and R3) and free fatty acid (FFA) plus ammonia (blue, R1), (FIG. 32C) confirmation of acyl chain composition by tandem MS detects the diagnostic DAG product ions minus a free fatty acid compared with known masses. [94] DAGs represented in multiple TAGs shown are only labeled once for clarity. sn-positioning of each acyl chain was not determined. P, 16:0-palmitic acid; O, 18:1-oleic acid; L, 18:2-linoleic acid;

(FIG. 33G) representative TAG profiles of Bnfad2 (blue) and Coker 312 (red) using DOMS of the purified LDs shown in FIGS. 33C and 33D. Scale bars represent 10 µm (FIGS. 33A and 33B) and 2 µm (FIGS. 33C-33F). P, 16:0-palmitic acid; O, 18:1-oleic acid; L, 18:2-linoleic acid;

FIG. 34D, Bnfad2) acquired through direct organelle mass spectrometry of small LD populations (10-25 LDs) relative to conventional total lipid extracts. Predominant acyl chain combinations were quantified by integrating the absolute intensities of peaks identified through tandem MS, correcting for isotopic overlap, and converting to molecular percentages. P, 16:0-palmitic acid; O, 18:1-oleic acid; L, 18:2-linoleic acid;

(FIG. 35A) bright field snapshot image of a nanospray emitter directly sampling a single LD. Scale bar represents 5 µm, (FIG. 35B) representative TAG profiles with acyl chain designations of single LD from Tables 2 and 3 (Coker 312 LD6 and Bnfad2 LD6. LD-TAG peaks are attenuated according to the right axis to show resolution of peaks relative to spiked Tri 15:0 TAG standard represented by the left axis, (FIG. 35C) heterogeneity of TAG content within single seed LDs (n_7 for both Coker 312 and Bnfad2). Numerical values are in Tables 2 and 3. P, 16:0-palmitic acid; O, 18:1-oleic acid; L, 18:2-linoleic acid;

(FIG. 36A) representative confocal image of BODIPY 493/503 stained LDs of 48-h germinated roots, (FIG. 36B) bright field image of purified root LDs and resulting TAG profile (FIG. 36C, blue) relative to cotyledon cottonseed LDs (FIG. 36C, red). Cyclic fatty acid abbreviations are as follows: Sc, sterculic acid; Dsc, dihydrosterulic acid. Scale bars represent 10 µm. P, 16:0-palmitic acid; O, 18:1-oleic acid; L, 18:2-linoleic acid;

(FIG. 37A) sterculic, (FIG. 37B) dihydrosterculic, (FIG. 37C) fatty acids analyzed in neutral loss mode on a triple quadrupole MS. Dominant TAG species are identified as ammonium adducts $[M+NH4]^+$ with peaks labeled according to the total number of carbons followed by the total number of double bonds for that particular TAG mass-to-charge ratio. Underlined species in the malvalic/linoleic scan (FIG. 37A) correspond to TAGs with at least one sterculic or dihydrosterculic acyl chain.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

A technique involving the combination of nanomanipulation and nanospray mass spectrometry (NMS) for single cell, single organelle, and ultra-trace molecular analysis is described herein below.

Figure 11A:
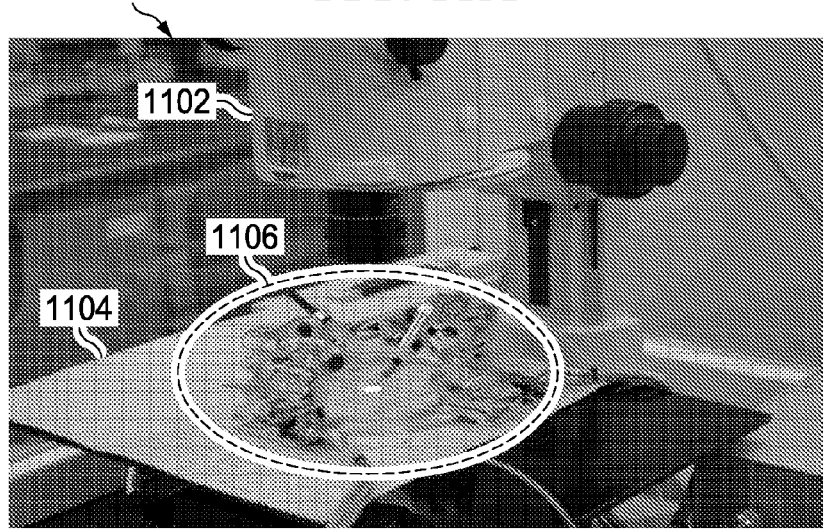
FIGS. 11A and 11B show ink extraction from a written document with the nanomanipulator.
Figure 11B:
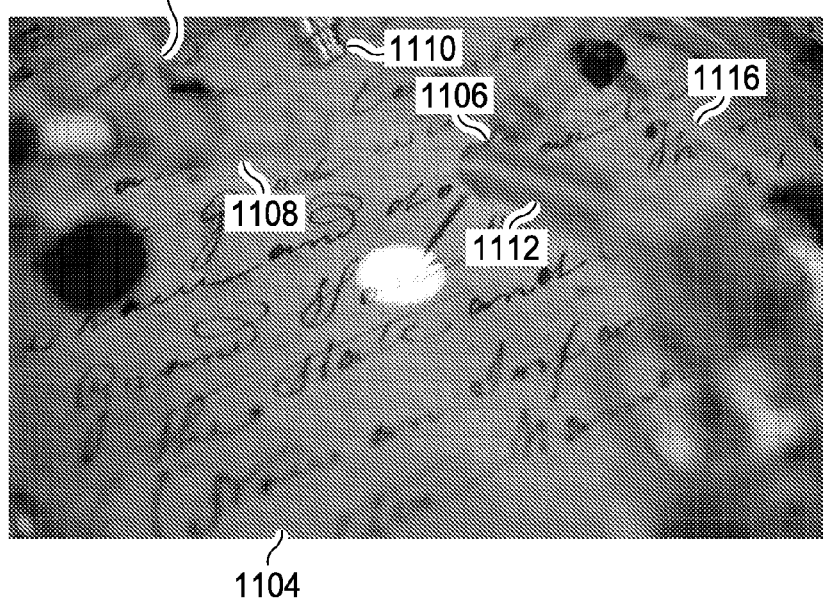

The advent of small volume analysis with mass spectrometry has opened the door to the study of micron and submicron analytes, and bringing the sampling directly to the area of interest. The nanomanipulator of the instant invention is a multistage bioworkstation consisting of a four-positioner system that has been directly coupled with nanospray mass spectrometry (NMS). This coupling allows for new significant applications developments in the areas of trace and document analysis within the forensic field. This technique has been applied to trace fiber analysis and electrostatic lifts for illicit drugs, as well as document and painting analysis (as seen in FIGS. 11A and 11B). In FIG. 11A The document or painting (1104) is placed on the stage of the microscope. The nanomanipulater assembly (1106) is placed on top of the document, underneath the microscope objective (1102). As seen in FIG. 11B the ability to connect two of the nanopositioners (1106 and 1108) to the pressure injector (1114 and 1116) allows for extractions using two capillary tips. In this case of the tips in lowered towards the document (1104) in order to perform an extraction of the ink. The other nanopositioners (1110 and 1112) can be equipped with tweezers or probes to carry out other processes.

The low detection limits and sample volumes make nanospray ionization-mass spectrometry the ideal instrument for trace analysis. The present inventors have demonstrated the technique by dissolving an electrostatic particle of cocaine from a fiber and lift, collecting the analyte solution in a nanospray tip, and transferring the tip directly to the mass spectrometer to complete the analysis. The technique of the present application was applied to document analysis. The importance of leaving minimal "footprints" behind to retain the integrity of the document is one of the most advantageous benefits of this technique Inks, as well as, paints and pigments were analyzed, illustrating the minimal damage to the document during analysis. The utility of this technique is evident through the minimal sample preparation and short analysis time. The technique presented herein could improve on current trace particulate analysis and document analysis by reducing both detection limits and sample size required to complete analysis.

Figure 10:
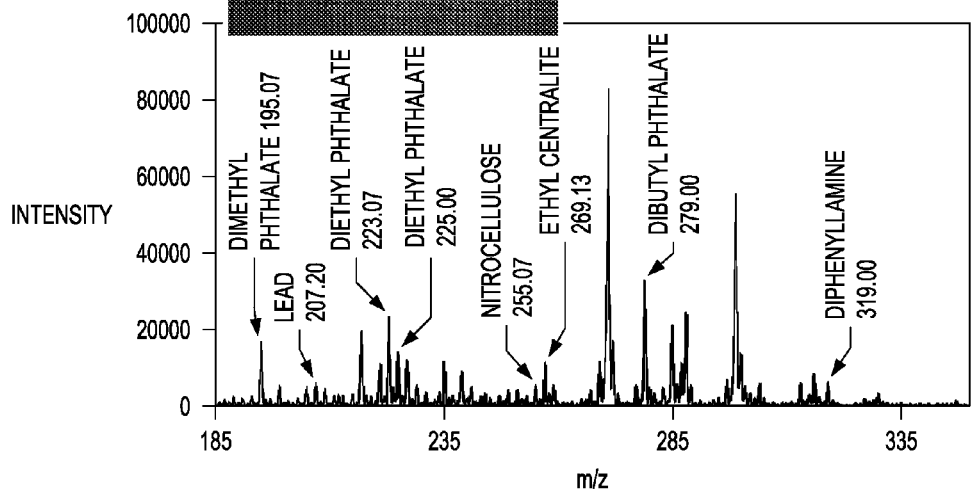
FIG. 10 shows a gunshot residue sample and accompanying mass spectrum.

The few applications described hereinabove are only a few among all of the possible applications especially with the ability to design and fabricate new end-effectors with unique abilities. The instant invention can be applied to direct cellular probing including toxicology studies and organelle analysis of single cells and also in forensic sciences (e.g., gunshot residue sampled from fibers 1004 as seen in FIG. 10).

The multistage bioworkstation used in the instant invention consists of a nanomanipulator stage with four nano-positioners which are attached to a cabinet with a piezo voltage source and a pressure injector. The bioworkstation is mounted to the stage of the inverted microscope; it can be easily transferred to other microscopes enabling access to different types of visualization (confocal vs. wide-field). The workstation can hold up to eight nano-positioners allowing multiple probing tips and end-effectors to be used if needed. There are two coarse mode nano-positioners which are driven by a stick slip drive. It has a PWM signal that is applied to an arm with a ceramic bead attached to the end. The arms path is an oval; the band sticks to a ceramic plate then slips back which repeats the cycle to generate the movement. The range of motion is 12 mm in the X and Z axes and 28 mm in the Y axis with a resolution of 100 nm. There are two fine nano-positioners having coarse mode abilities as well as an optional fine mode that has a 10 nm resolution. The fine mode nano-positioners are driven by a piezo-electric crystal, when high voltage is applied to the crystal it expands. The geometry and orientation of the crystal is responsible for the range of motion in each axis (X,Y,Z). The range of motion of the fine mode is 100 µm in the Z and X axes and 10 µm in the Y axis. The present inventors have an added motion in being able to manually tilt the nano-positioners. In total there are 4 degrees of motion.

The bio-workstation was coupled to nanospray mass spectrometry as shown in the image 100 in FIG. 1A. The nanomanipulator is placed on top of the microscope stage (114) on an inverted microscope (116). The nanomanipulator consists of four positioners; two which can be affixed with capillaries for nanospray extraction (102 and 108) the other two positioners can be used for probes and grippers (104 and 106). The specimen to be manipulated; for example, analyte particles (112) or fibers (110) are placed underneath the positioners (102, 104, 106, and 108). This coupling was made possible by adjusting the coarse nano-positioner to hold a nanospray tip. The process includes filling a nanospray tip with a nanospray solvent and an adducting ion then inserting it into the nanospray source and breaking the tip open. The nanospray tip is then transferred to the nano-positioner and the tip landed near the object of interest. The pressure injector gives a controlled amount of pressure (0.001 psi to 60 psi) to the tip to inject the solvent and dissolves the analyte of interest followed by pulling the dissolved analyte back into the tip. The nanospray tip is then transferred to the nanospray source and the analyte is analyzed based on its m/z as well as its fragment pattern, $MS^n$, this coupling allows for the analysis of multiple compounds.

The bio-workstation can also be coupled to other instruments including microfluidic systems allowing for the separation and analysis of a mixture of compounds. Microfluidic systems are now being directly coupled to mass spectrometry to analyze samples allowing for future sampling, separation, and analysis.

The capillary tips (100 nm to 5 µM, diameters) are attached to the nano-positioners which are connected to a pressure injector with an injection pressure of 60 psi and a fill pressure of 24 mmHg. Capillary tips can be used to sample directly from cells. The present inventors have set up sequences with up to four capillaries in order to increase productivity and expand the types of studies that can be performed. The pressure injector has a hold function allowing a beveled capillary tip to hold a cell if necessary. Capillary tips are as small as 1 µm with using a pressure of 60 psi to overcome the surface tension of water. It takes less to overcome the surface tension of different solvents with lower viscosity. Surfactants may be used to lower the surface tension and allow the injection and fill to take place.

In the past micromanipulation can be accomplished with fine motor drives. The instant invention however, includes the fine stick-shift technology of piezio allowing true nano manipulation offering a very distinct advantage. The stick-shift motion is from 3 nm to 100 nm. In addition, current manipulation techniques have a resolution of only 1 µm motion, ultra fine analysis requires better resolution, as provided by the present invention.

Direct probing from a sample surface directly coupled to mass spectrometry (MS) is a useful tool, helping to eliminate sample preparation and analysis time. Currently, there are three techniques at the forefront of direct-coupled surface sampling MS: desorption electrospray ionization (DESI) [1], surface sampling probe electrospray ionization [2], and dielectric barrier discharge ionization source (DBDI) [3]. DESI sprays charged solvent droplets onto an ambient surface which ionizes neutral analytes. The analytes are then desorbed from the surface and analyzed using MS [1,4]. DESI has been used to detect trace amounts of explosives as well as sampling directly from human skin [5,6]. Surface sampling probe electrospray ionization uses a liquid junction between the electrospray source and the surface to dissolve and then ionize the analyte, which is then electrosprayed into the MS [2,7]. This method has been used to sample drugs directly from thin tissue slices [8]. DBDI uses a dielectric barrier discharge to create a stable plasma flow that desorbs and ionizes the sample off of an ambient surface, then analyzes it using MS [3]. All of these techniques have great utility, but need a relatively large area (20-100 µm$^2$) for analysis.

Micromanipulation is a significant tool in the biological and chemical sciences. It is utilized primarily to manipulate small particles and cellular materials because of its precise movements. It is currently being used in the biological sciences for single cell transfer [9], to isolate specific bacterial cells from a group [10], and it has also been employed for sample preparation for MS analysis [11]. Mitochondria have been extracted from cells using micromanipulation and subsequently analyzed using electrophoresis [12].

Nanomanipulation as discussed herein will generally refer to the use of a commercially available instrument from Zyvex (Richardson, Tex.) that has the capability of manipulating samples as well as extracting target analytes from those samples. As the nanomanipulator was designed to be utilized with electron microscopy, the manipulator end-effectors have better than 5 nm translational resolution, which is beyond the optical limit. This allows for new advances in the biological and chemical sciences to be made through precise movements and minimally invasive sample manipulation.

EXAMPLE I

Trace Analyte Sampling

One of the current methods of probing trace analytes is the swab method, whereby an object's surface is swabbed using a textile sampling swab that is then put into a solvent to extract the analyte of interest [13]. This method is not the best way to collect trace analytes because of analyte losses and dilution of analyte concentration. Repetitive handling of the analyte, associated with multistep processes, can lead to sample contamination [14]. Additional difficulties arise when attempting to swab a single fiber, as analyte concentrations will be very low, making analysis difficult. Improvement in trace analyte sampling is needed to more accurately solve problems and collect trace evidence.

Mass spectrometry is a useful tool for trace analysis because of its high sensitivity, allowing it to be useful for a wide variety of compounds. Nanospray is an ideal ionization source to couple to nanomanipulation, because it reduces sample preparation time and requires a small concentration of analyte (pmol/µL). Nanospray is an ionization technique that, at best, requires 300 attograms ($10^{-18}$ g) of analyte with a minimum volume of 300 nL. Additionally, it is not as affected by salts as electrospray ionization, which further reduces sample preparation [15]. Liquid chromatography-electrospray ionization-mass spectrometry (LC-ESI-MS) has been used in the analysis of explosives [16] and other trace analytes because of the ability to deconvolute a large sample matrix. Using nanomanipulation, the nanospray tip is brought to the analyte to discriminate particle selection, which would help to both deconvolute the spectra and elucidate the identity of the analyte. These techniques can be applied to trace analysis as described herein, expanding current abilities, so that the trace is now able to be extracted and analyzed.

Materials: The solvents and chemicals utilized were chloroform ($CHCl_3$), glacial acetic acid (HOAc), Optima* LC/MS methanol (MeOH), and caffeine (Thermo Fisher Scientific Inc., Waltham, Mass.); no further purification was necessary. A sample of freebase cocaine was provided by the University of North Texas Police Department (Denton, Tex.). Millipore water was obtained using the Milli-QUF Plus (Millipore, Billerica, Mass.) with better than 18 MX salt content. Glass-bottom dishes were used to hold our samples (Mat Tek Corp., Ashland, Mass.), and analytes were probed from 100% rayon white bemberg lining. The MS utilized was an LCQ DECA XP Plus (Thermo Finnigan, San Jose, Calif.) with a nanospray ionization source (Proxeon Biosystems, Odense, Denmark). The inventors have also attached the nanospray source onto a a Thermo Finnigan TSQ 7000 Triple Quadrupole to run a similar analysis. An L200 nanomanipulator (Zyvex, Richardson, Tex.), coupled to a TE2000U Microscope (Nikon, Melville, N.J.) and a PE2000b four-channel pressure injector (MicroData Instrument Inc., S. Plainfield, N.J.) were used to retrieve the analyte from the fiber.

Methods: The L-200 nanomanipulator 100 is mounted to a Nikon TE2000U inverted microscope (114). The nanomanipulator employs four nanopositioners (102, 104, 106, and 108) that can be controlled using a joystick and/or digital input (FIG. 1A). The nanopositioners have two modes of action that allow for precise control of their movements. In the coarse mode of action, the nanopositioners have a range of motion of 12 mm in the X and Z axes and 28 mm in the Y axis. The fine mode of action allows for a range of motion of 100 µm in the X and Z axes and 10 µm in the Y axis. The nanopositioners are further distinguished by the type of manipulation tools they use. Two nanopositioners are capable of holding end-effectors (either tungsten probes 106 or microgrippers 104) that can be utilized in either the coarse or fine mode with 3.4 nm translational resolution. The remaining two nanopositioners (102 and 108), which are run in coarse mode only, hold capillary tips and are capable of 100 nm translational resolution (FIG. 1B). As seen in FIG. 1B the nanopositioner (152) is connected to a pressure injector (156) via plastic tubing (158). The positioner is controlled in the x, y, and z directions (154) and placed in close proximity to the fiber (164) which is on the microscope stage (166). The nanospray tip (160) is preloaded with extraction solvent (162). The solvent is injected onto the sample (168). The PE2000b pressure injector (156) is used to supply up to 60 psi of injection pressure and 24 inches Hg of fill vacuum to the capillaries, allowing us to retrieve the analyte of interest. The capability of the nanomanipulator to hold up to eight nanopositioners is beneficial because it allows one to conduct multiple probes simultaneously and thus, increases the instrument's capabilities and efficiency.

The Au/Pd-plated nanospray tips (160) were loaded with an appropriate solvent, and then the tip was broken using the nanospray source head. A blank was run to determine any solvent contamination, and a background spectrum of the solvent was taken. The tip was then transferred to the nanomanipulator for trace analyte probing from a rayon fiber (164) that was doped with the analyte of interest and placed in a glass-bottom dish (168). The rayon fiber (164) was tacked down to minimize the movement of the fiber and, therefore, the movement of the analyte on the fiber. The particle of interest was found on the fiber, and then the nanospray tip (160) was landed near it, <1 µm away. The nanospray tip then injected the solvent (162) onto the analyte. After the analyte had dissolved, the solvent/analyte solution was retrieved back into the tip (160). The nanospray tip (160) was then transferred directly to the nanospray ionization source and the sample analyzed.

Figure 2A:
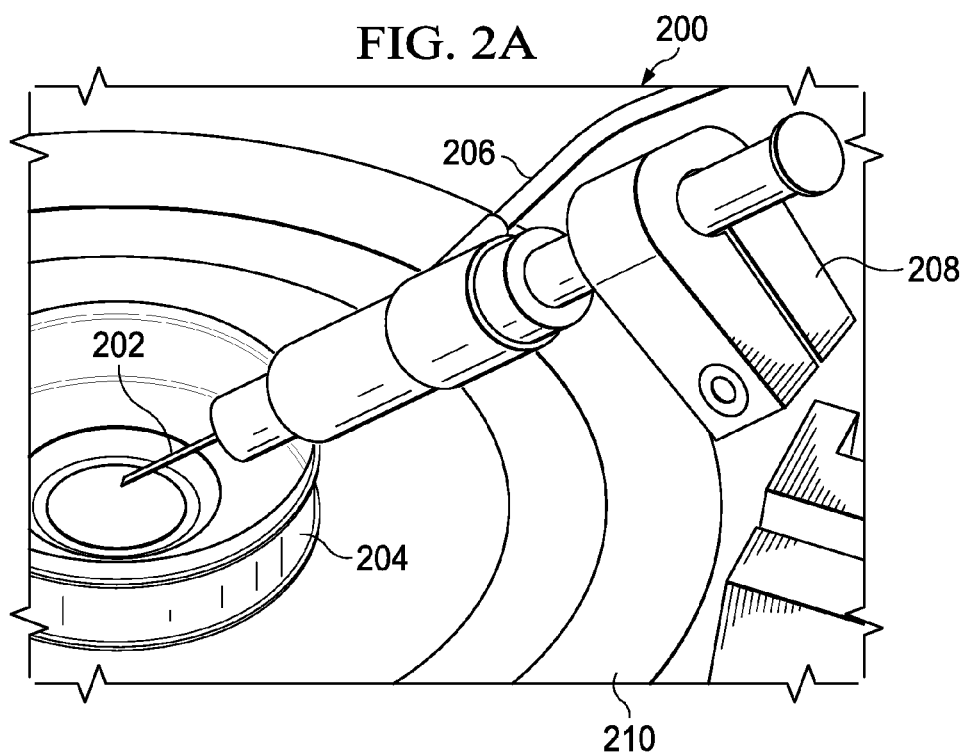
FIG. 2A shows the nanomanipulator positioner with the nanospray tip probing an analyte.
Figure 2B:
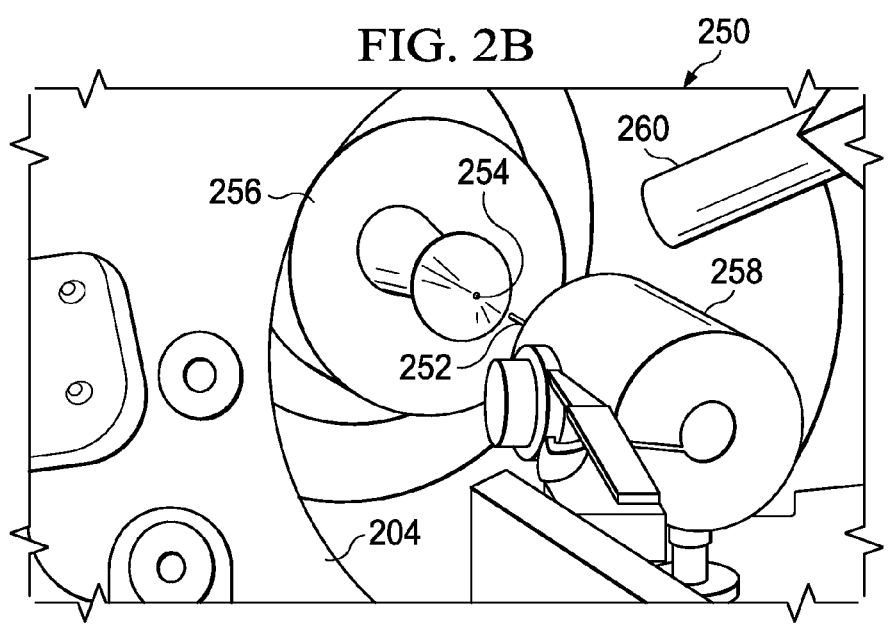
FIG. 2B shows the nanospray ionization source showing the nanospray tip that was transferred directly from the nanomanipulator.
Figure 3:
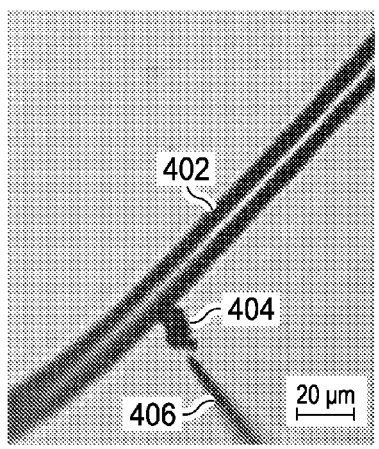
FIG. 3 shows a rayon fiber doped with analyte before extraction, the caffeine particle is on the rayon fiber and the nanospray tip is landed in close proximity.

FIG. 2A shows one of the positioners (208) of the nanomanipulator with a nanospray tip (202) retrieving an analyte. The sample of interest is placed in a dish (204) which is placed on the microscope stage (210). The nanopositioner (208) is affixed with a nanospray capillary (202) and placed in close proximity to the sample. A pressure injector is connected to the positioner with plastic tubing (206). FIG. 2B shows the tip mounted onto the nanospray ionization source (258). Cocaine was used to illustrate this technique. The nanospray capillary (252) is placed in the nanospray housing (258). A mini light (260) is attached to the camera mount (204) is shone on the mass spectrometer inlet (254 and 256). When sampling, 50:50 MeOH: $H_2O$ with 1% HOAc was used as the solvent and 3 µL was loaded into the nanospray tip. The tip (406) was landed next to the analyte (404) as shown in FIG. 3. A particle (404) is adhered to a rayon fiber (402) and a nanospray capillary (406) is placed near the particle for extraction. The nanomanipulator used an injection pressure of 20.8 psi for a duration of 11 ms delivered from the pressure injector and a fill pressure of 65.0 psi with a fill time of 50 ms. The sample was then analyzed in the positive ion mode using a 2 kV extraction voltage on the NSI-MS. The mass spectrum of cocaine can be seen in FIGS. 5A and 5B.

Figure 5A:
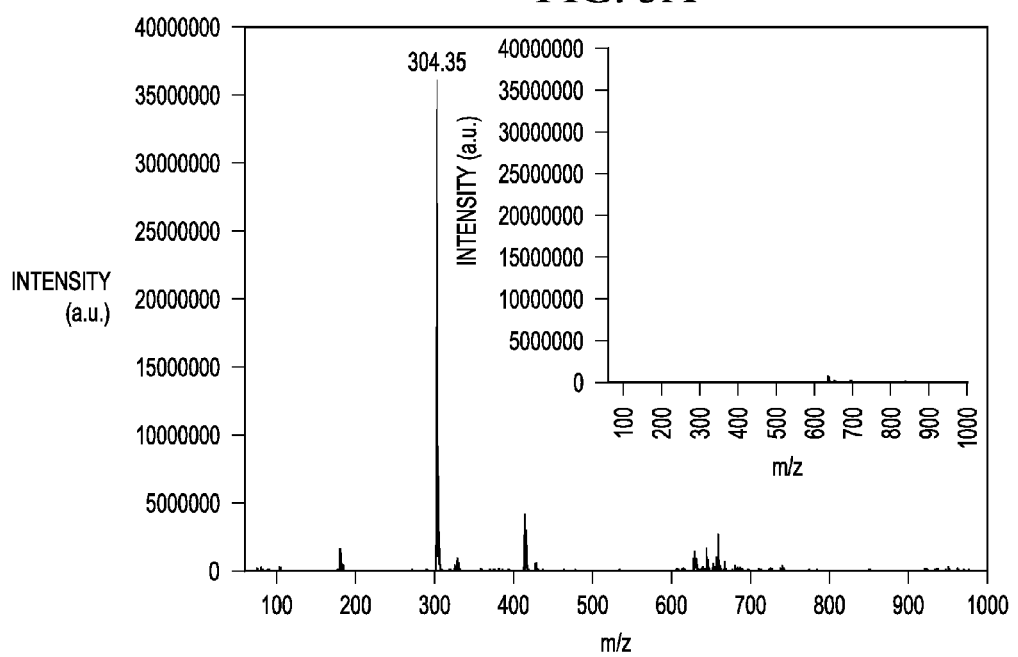
FIG. 5A is the mass spectrum of cocaine (MW: 303.35 g/mol) taken in positive ion mode after extraction from a single rayon fiber. The MH$^+$ peak appears at m/z 304.35. The inset shows the mass spectrum collected from an extraction on the fiber with no analyte present.
Figure 5B:
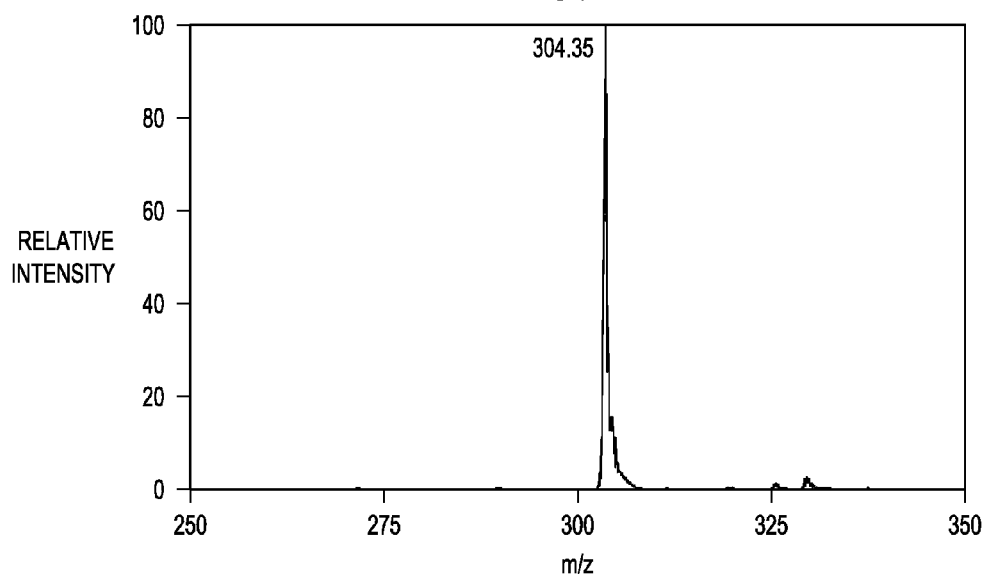
FIG. 5B is a blow-up of mass spectrum shown in FIG. 5A between m/z 250-350.

Cocaine trace particles were sampled directly from a single rayon fiber using the nanomanipulator and then analyzed using NSI-MS. FIG. 5A shows the mass spectrum of cocaine after directly probing a trace particle from the rayon fiber. As analysis was completed by NSI, the $MH^+$ peak is most prominent and appears at m/z 304.35, as well as the characteristic fragment peak at m/z 181.94. The inset of FIG. 5A displays the blank when the solvent was allowed to extract on the fiber with no analyte present. As can be seen from the inset, the fiber contributed no appreciable peaks to the mass spectrum of cocaine. FIG. 5B displays a blowup of the m/z 250-350 range.

Figure 4:
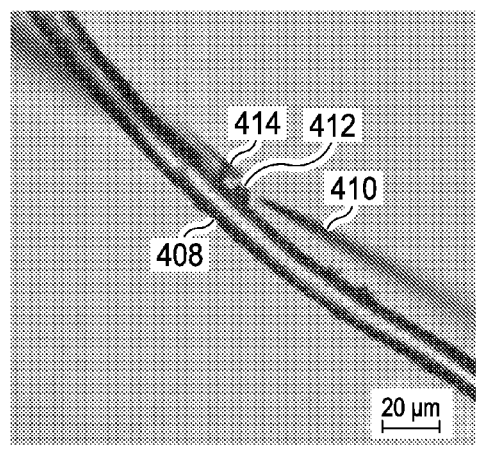
FIG. 4 shows a rayon fiber doped with analyte before extraction with a two capillary method with a histidine particle between the capillary tip on the left and the nanospray tip on the right.
Figure 9A:
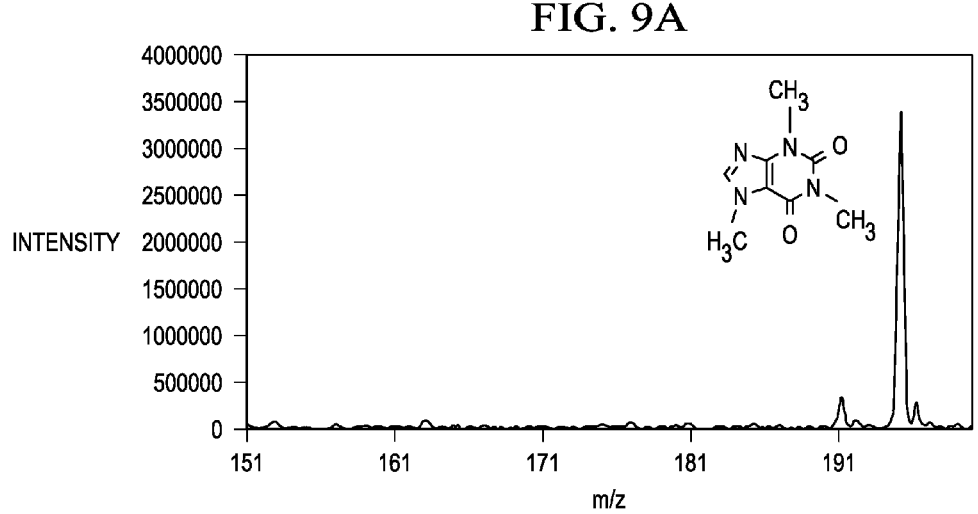
FIGS. 9A and 9B show the mass spectra of caffeine and histidine respectively.
Figure 9B:
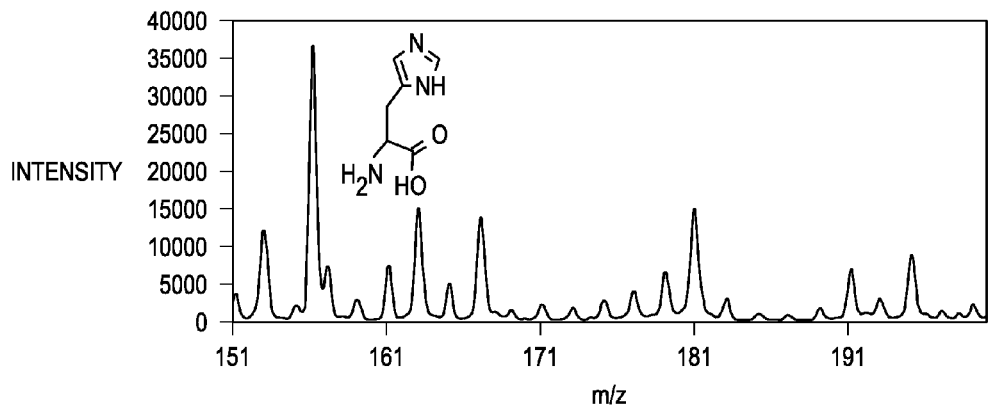

The results clearly show that the nanomanipulator coupled to NSI-MS is an effective instrument to probe trace analytes from fibers. It is an improvement in trace analyte probing from a single fiber, allowing for new experimental procedures to be created and smaller amounts of analyte to be sampled. The nanomanipulator reduces cost of sampling from fibers because of the minimal sample preparation and the reduced analysis time. Computer encoding of the positioners may be implemented to automate the procedure. Being able to recover trace analytes from a single fiber allows for better analysis of crime scenes, and the reduced sample size and volume required for NSI-MS allows for the ability to retrieve a higher sample concentration. Although the research for this article has focused on cocaine, this technique has also been applied to other particulate analyte standards including caffeine and histidine (FIGS. 9A and 9B), and the limit of detection by NSI-MS is on the order of 7 pg (1 pg=$10^{-12}$ g) for histidine, which demonstrates the extreme sensitivity achievable by this technique. This technique has also been applied to analysis of single organelles and protein extraction from silicon beads, currently being developed by the present inventors. It is important to have a solvent to dissolve the sample as well as provide a steady spray flow. Some nonpolar compounds will not dissolve in any of the solvents appropriate for nanospray, so it is important to utilize a two capillary system with one capillary containing a solvent to dissolve the analyte, and the other capillary containing the nanospray solvent that retrieves the dissolved analyte. FIG. 4 illustrates the two capillary system used with some nonpolar analytes. A particle (412) is adhered to a rayon fiber (408) and two nanospray capillaries (410 and 414) are placed in close proximity to the particle for extraction. Diffusion will occur, and the small amount of nonpolar solvent with the analyte of interest will mix with the nanospray solvent, and the resulting solvent/analyte mixture can be analyzed using the NSI-MS. The nanomanipulator is also capable of liquid-liquid phase microextractions to sample trace analytes and gain higher sample concentration from a dilute analyte in a liquid sample and then complete analysis.

The example discussed hereinabove centered around the analysis of particulates on fibers which are particularly well suited for analysis by an inverted microscope but that by no means limits this method to fibers. The technique presented here works equally well for hair, paper, money, computer chips, treated wood, laminate, metal, manipulated surfaces including mylar electrostatic lift films, plastic, or any other surface where trace particulate analytes are expected. Difficulties arise with some of these specimens because they are not all equally suited to examination by an inverted microscope. In this case, the nanomanipulator stage could be transferred to a noninverted microscope.

EXAMPLE II

Liquid-Phase Microextraction-Coupled NSI

Advancements made in chemical separation instrumentation have coincided with the development of liquid-phase microextraction (LPME) in which small volumes (nL to µL) are used to partition and concentrate analytes based on their solubility within two immiscible or partially miscible liquid phases. Implementation of this miniaturized liquid-liquid extraction (LLE) method has traditionally been carried out as a single-drop solvent extraction [18, 19] or through a porous polymeric hollow fiber [20]. Each method enhances separation and concentration efficiency for many applications relative to the LLE and allows the coupling to analytical instrumentation developed for minimal sample volumes.

The first drop-in-drop solvent extraction method (SDME) as developed by Liu and Dasgupta [21] utilized a multitube assembly to suspend a water-immiscible organic microdrop (~1.3 µL) within a larger continuously supplied aqueous droplet. The apparatus measured the concentration of the analyte through a fiber optic absorbance detector and was amenable to liquid/gas chromatography by pumping away the concentrated analyte. Jeannot and Cantwell [22, 23]

simultaneously developed a LMPE apparatus in which a gas chromatographic syringe suspended an organic microdrop that could be withdrawn and directly injected in the GC. The more recent development of continuous-flow microextraction (CFME) [24] utilized an HPLC solvent delivery system forcing the organic microdrop to continuously make contact with a fresh and flowing sample solution. In addition, a solvent extraction apparatus developed for MALDI experiments [25] forms a nanoliter size organic droplet surrounded by an aqueous sample within a micropipette tip that can subsequently be deposited on a MALDI matrix for direct MS analysis. Alternatively, Shen and Lee [20] developed a hollow-fiber solvent extraction method that contains organic solvent within a hollow fibrous membrane immersed in aqueous solvent amenable to GC.

The improvements in nanospray mass spectrometry (NMS) in terms of versatility and sensitivity have led to an emphasis on analyzing small molecular concentrations and volumes. Nanomanipulation has traditionally been discussed in terms of manipulation of nanometer size objects with a nanometer size end-effector with (sub)nanometer precision [26]. The present inventors have developed a versatile LPME technique for nanoliter to microliter volumes that is amenable to direct NMS analysis (LPME-NMS). A multistage bioworkstation (FIG. 1A) consisting of four nanopositioners was coupled to an inverted microscope allowing the possibility to visualize, manipulate and analyze small samples. The utility of LPME-NMS was illustrated by extracting and analyzing molecules from a fluorescent dye dissolved in an aqueous solvent, non-polar polymer additives in vertebrate serum, and triacylglycerols within industrial refined cottonseed oil.

Sample Preparation: BODIPY (493/503, D-3922), 4,4-difluoro-1,3,5,7,8-pentamethyl-4-bora-3a,4a-diaza-s-indacene, a fluorescent neutral lipophilic dye was purchased from Invitrogen (Carlsbad, Calif.). Tripentadecanoin (1,2,3-Tripentadecanoylglycerol) was purchased from Sigma-Aldrich (St. Louis, Mo.). High purity Optima™-grade solvents were purchased from Fisher Scientific (Hampton, N.H.). Cottonseed oil processing fractions were provided through the coordination of David Kinard (National Cottonseed Products Association) from a refinery in west Texas. The vertebrate serum sample was prepared by Proteintech Group Inc. (Chicago, Ill.) from an antibody preparation directed to recombinant plant fatty acid amide hydrolase and processed by affinity column chromatography.

Nanomanipulator: The Biometric L200 nanomanipulator workstation developed by Zyvex (Richardson, Tex.) combines four nanopositioners (FIG. 1A) with a piezo voltage source and a pressure injector situated on an inverted microscope stage (TE2000U, Nikon, Melville, N.Y.). The nanomanipulator has two modes of motion along the X, Y, and Z axes. The fine mode has 100 microns of travel in the X and Z axis and 10 microns of travel in the Y axis with 3.4 nm resolution controlled by piezo-electric crystals. The coarse mode has 12 mm of travel in the X axis and Z axis and 28 mm of travel in the Y axis with 100 nm resolution. The positioners consist of end-effectors made up of six isolated, low impedance electrical connections and two glass capillary attachments. The end-effectors are used for manipulation and, if needed, low impedance electrical characterization. Probes and capillaries attached to the positioners can be manually landed onto the sample and manipulated electronically using a joystick to control the end-effector's position. The capillaries are connected by Teflon tubing to a PM 2000B Programmable 4-Channel Pressure Injector (Microdata Instruments, South Plainfield, N.J.).

Liquid-phase microextraction: In LPME a liquid phase (Phase I, aqueous in practice) containing the analyte of interest is in direct contact with an immiscible extractant liquid phase (Phase II, organic solvents in practice) [27]. The analyte of interest will then diffuse into its preferred phase based on its distribution coefficient $\kappa$ [27]. There are many experimental factors that influence the analyte's extraction capability including its compatibility within the phases, pH of the phases, extraction time and agitation of phases, as well as the volume ratio of the extractant and donor phases [28]. Thermodynamic and kinetic considerations must also be taken in account to predict extraction behavior [22]. The thermodynamic equilibrium concentration in the organic phase $$C_{o,eq} = \kappa C_{aq,eq} = \frac{\kappa C_{aq,initial}}{1 + \kappa V_o / V_{aq}} \quad (1)$$

where $C_{aq,initial}$ and $C_{aq,eq}$ are the initial and equilibrium aqueous phase concentrations, demonstrates that although it might not be feasible to reach equilibrium due to time constraints, a sufficiently large distribution coefficient, $\kappa$, is necessary for efficient extraction [22]. In order to maximize $\kappa$ and concentrate the analyte in the extracted phase, it is crucial to minimize the volume ratio $V_o/V_{aq}$ of the organic and aqueous phases [22]. Kinetically, the observed rate constant (s−1) validates that for rapid analysis the interfacial area (Ai) and mass transfer parameters ($\beta 0$) must be maximized and the volume of the aqueous phase (Vaq) minimized [22].

$$k = \frac{A_i}{V_o} \overline{\beta}_o \left( \kappa \frac{V_o}{V_{aq}} + 1 \right) \quad (2)$$

Liquid-phase microextraction was carried out by backloading an extraction solvent (typically 3 μL) with GELoader™ tips (Eppendorf, Westbury, N.Y.) into the nanospray capillary (FIG. 1B). The nanospray capillary mounted to the L200 nanomanipulator was subjected to a positive balance pressure (<1.0 psi) to minimize capillary action at the tip opening while breaking through the sample's surface. A programmed C# script was used to control the agitation of the capillary by transversing the plated sample parallel to the capillary opening. The C# script has the flexibility to vary the velocity (0 to ~500 μm/sec), direction (x,y,z) and time to carry out a specific agitation pattern. The program carried out for the LMPE trials typically proceeded for 10 minutes back-and-forth parallel to the capillary opening multiple times at 500 μm/sec while also running perpendicular to the capillary opening at approximately 20 μm/sec to perform LMPE on as much of the sample as possible. The capillary was removed and mounted to the nanospray source for immediate analysis.

Mass Spectrometry: A Proxeon nanospray source (Proxeon Biosystems, Odense, Denmark) was mounted to a Thermo LCQ Deca XP Plus quadrupole ion trap (Thermo Fisher Scientific Inc., Waltham, Mass.). Samples in 1:1 (v/v) chloroform:methanol containing 1-2% glacial acetic acid (or alternatively, 10 mM aqueous ammonium acetate where noted) were infused through New Objective (Woburn, Mass.) Econo12 PicoTip™ Emitter platinum coated nanospray capillaries (1±0.2 μm). The ion source conditions consisted of a 0.6 to 1.2 kV spray voltage, an ion-transfer capillary temperature of 275° C., and an ion-transfer capillary voltage of 3.0 V. Mass spectra were acquired using the LCQ Tune software program in the positive ion mode with 3 microscans and a continuous acquisition time. The mass spectra were analyzed with the XCalibur 2.0 software package. Tandem mass spectrometry (MS-MS) performed on the cottonseed oil samples was used to confirm the identity of the triacylglycerols (data not shown). Tandem spectra were acquired in positive ion mode with a typical isolation width of 5.0 m/z, normalized collision energy of 35%, activation Q of 0.250, and an activation time of 30 milliseconds.

Figure 6A:
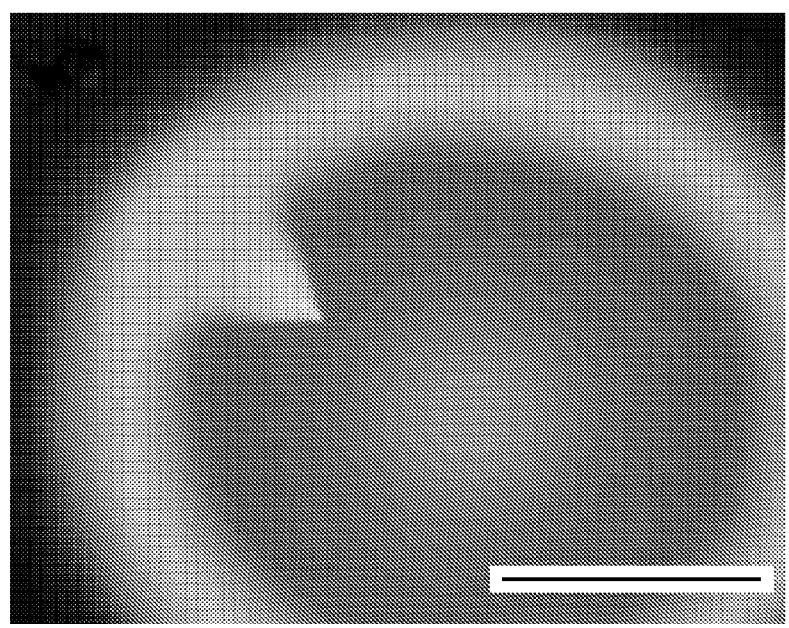
Figure 6B:
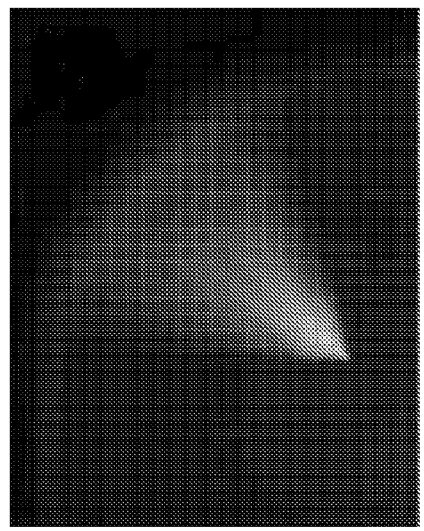
Figure 6C:
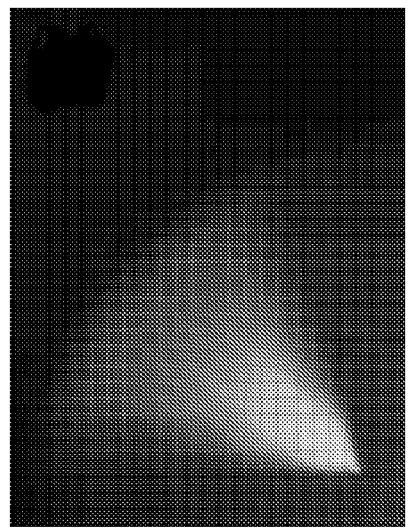
Figure 6D:
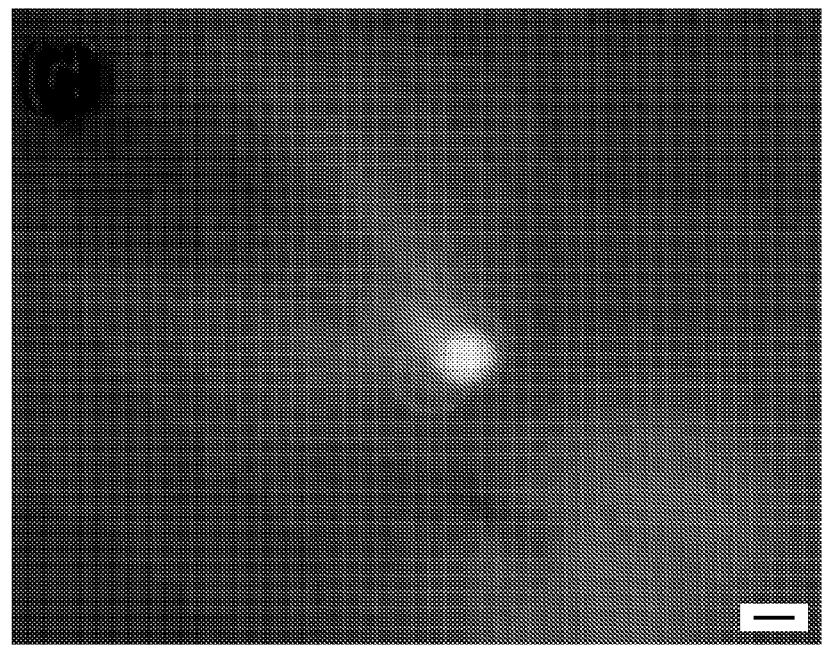
FIG. 6D shows another uncoated, empty nanospray capillary within the sample confirming the results were not resulting from autofluorescence of the extraction solvent. Scale Bars ~100 μm for FIG. 6A and ~5 μm for FIG. 6D.
Figure 6E:
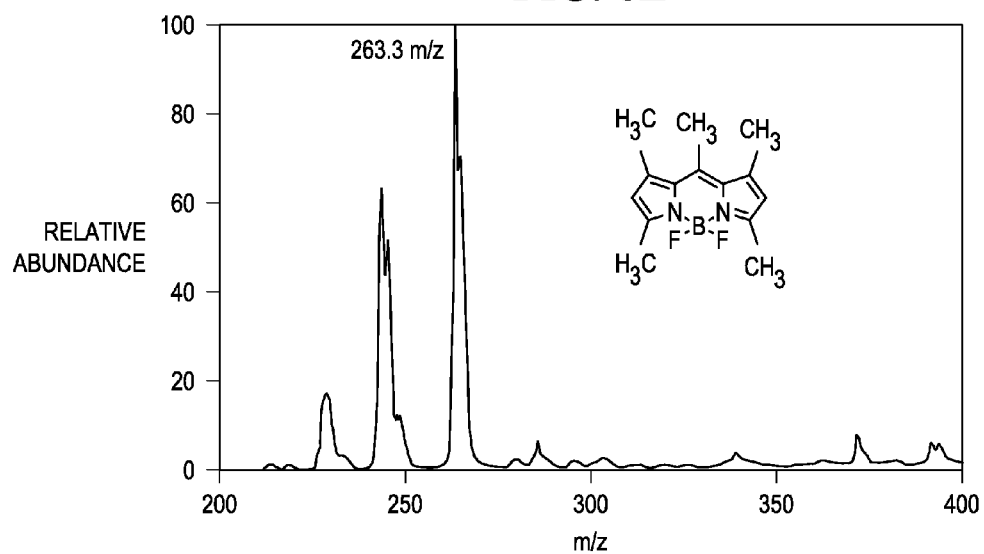
FIG. 6E is a nanospray mass spectra of BODIPY 493/503 dye sampled through LPME-NMS with 1:1 (v/v) chloroform: methanol containing 2% glacial acetic acid. A dominant peak of 263.3 m/z confirmed that the [BODIPY+H]+ was successfully extracted.

The development of LPME-NMS was first visualized by extracting the neutral lipid-specific fluorescent dye, BODIPY 493/503, within an aqueous background (2.5 µg/mL) via an uncoated chloroform-loaded capillary. The dye quickly concentrated within the pulled capillary tip portion in a time-dependent manner and was effectively extracted from the aqueous solution (FIGS. 6A-6C). The intense and prolonged fluorescence within the pulled capillary tip portion suggests a multifold concentration took place within nanoliters of chloroform. Negative control LPME experiments performed with an empty capillary (FIG. 6D, NC tip on the right), an aqueous loaded capillary (not shown), as well as an aqueous solution lacking the BODIPY dye (not shown) confirmed the validity of the LPME technique and the fluorescence within the capillary tip was not due to autofluorescence of the extraction solvent. Bearing in mind that uncoated nanospray capillaries could not be used directly for MS analysis, efforts were made in subsequent studies to eliminate the extraneous transfer step of the extract to a coated capillary and perform for the first time a direct coupling of LPME and NMS. A series of 10 minute BODIPY extractions with coated nanospray capillaries confirmed a dominant BODIPY peak at m/z 263.3 (FIG. 6E) supporting compositional consistency within the technique.

Figure 7:
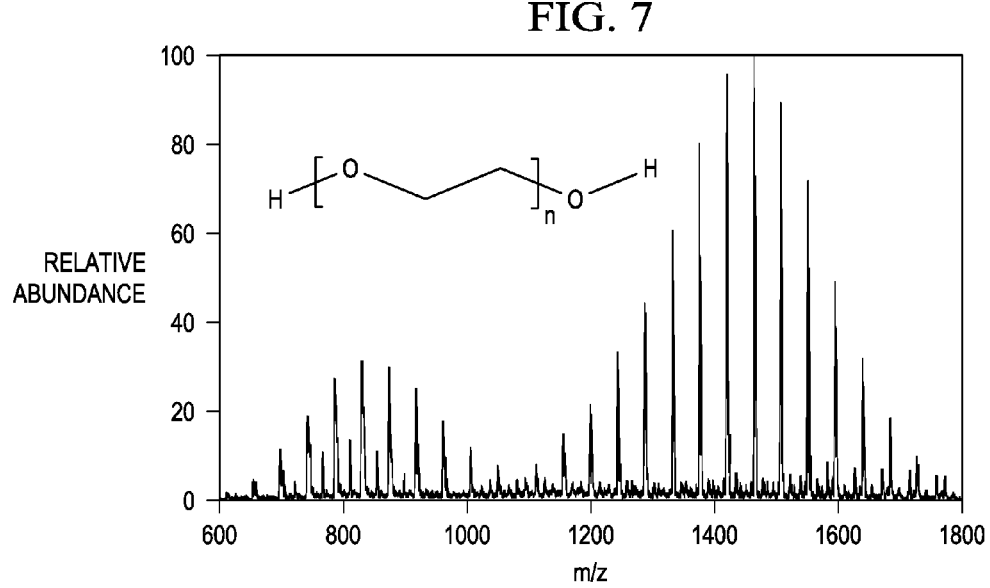
FIG. 7 shows two series of polyethylene glycol (PEG) chain polymers of 44 m/z units apart, average masses of 830.5 m/z and 1464.1 m/z, were extracted with 1:1 (v/v) chloroform:methanol containing 2% glacial acetic acid from vertebrate serum sample that had been processed by affinity column chromatography.

The selective extraction of lipophilic compounds from a complex biological sample was optimized to analyze extracts directly within the sampling capillary as a means to eliminate losses and streamline the direct coupling of LPME to NMS. Toward this goal, a sample of rabbit serum that had been subjected to affinity column chromatography (to purify antigen-specific antibodies) was sampled by performing the extraction directly with a solution (1:1 (v/v) chloroform: methanol plus 2% glacial acetic acid) that served as both an extraction solvent and an infusion solvent for ionization. The chloroform-methanol mixture is a common extraction solvent for lipophilic molecules [29] and its ratio can be adjusted to preferentially select for more or less polar analytes. However, due to the high volatility, very low surface tension, and low dielectric constant of chloroform [30], it was established the ratio has to be carefully considered for direct coupling of LPME to NMS. Other combinations of organic infusion/extraction solvents may be selected for a preferential extraction but it is important to consider whether the solution will still serve as an appropriate nanospray ionization solvent [30]. NMS confirmed that a polymer series of polyethylene glycol (PEG at 44 m/z apart), a common additive to stabilize affinity-purified antibody preparations, was selectively extracted from the serum samples (FIG. 7). The abundance of PEG and its high affinity for the extraction solvent likely overwhelmed the appearance of other less prominent lipophilic compounds that might have been present, such as triacylglycerols and cholesterol, especially since their concentrations would have been extremely low in these affinity-fractionated serum samples [31].

Figure 8C:
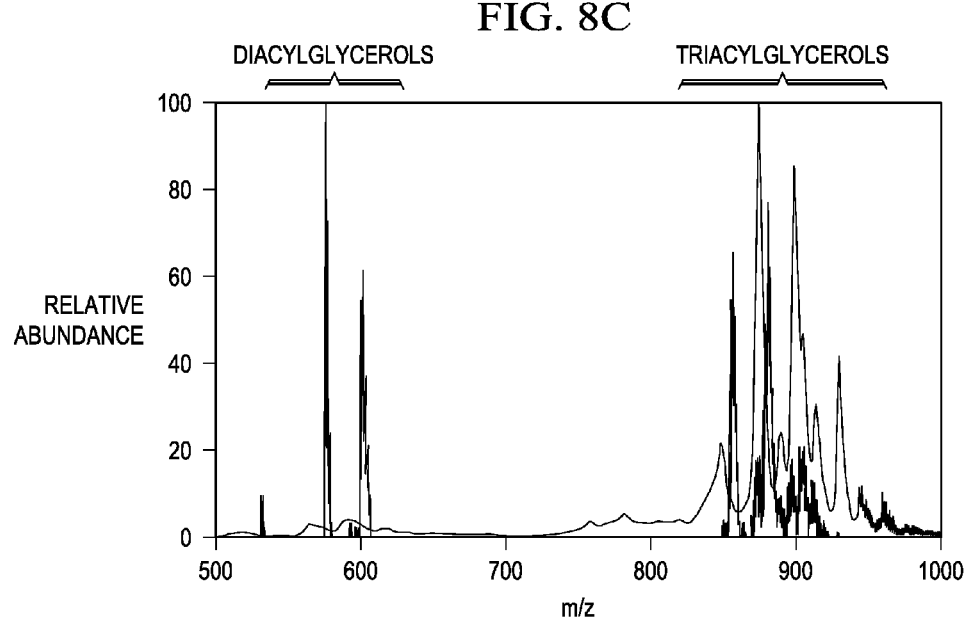
FIG. 8C is a representative acid-catalyzed hydrolysis spectra by LPME extraction with 1:1 (v/v) chloroform:methanol containing 2% glacial acetic acid of refined cottonseed oil (black lines) produced an abundance of diacylglycerol fragments (hydrogen adducts) for PL at 575.5 m/z, PO at 577.5 m/z, LL at 599.5 m/z, OL at 601.5 m/z, and OO at 603.5 m/z where P is Palmitate, L is Linoleate, and O is Oleate. (grey lines) The diacylglycerol fragments were effectively minimized by substituting 10 mM ammonium acetate in place of glacial acetic acid which produced triacylglycerols of primarily ammonium adducts.
Figure 15A:
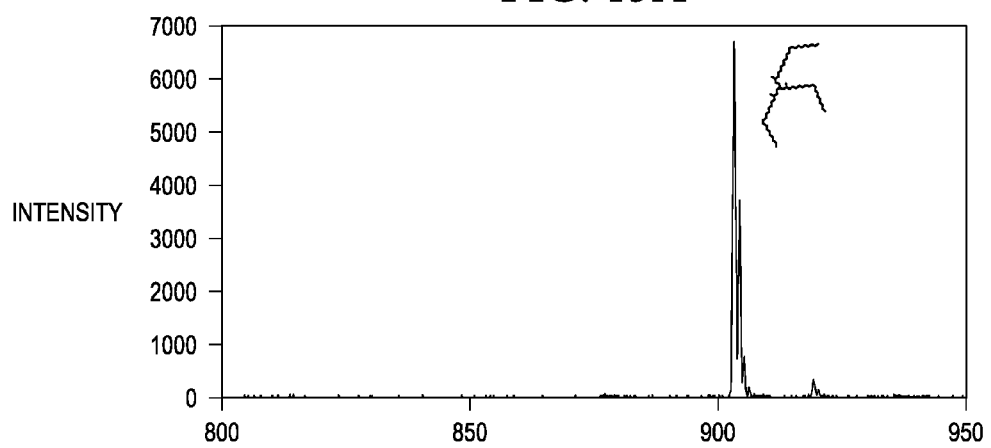
FIG. 15A is a mass spectrum of trioleate (1,2,3-tri-(9Z-octadecenoyl)-sn-glycerol) standard dissolved in 1:1 CHCl$_3$/CH$_3$OH plus 2% acetic acid.
Figure 15B:
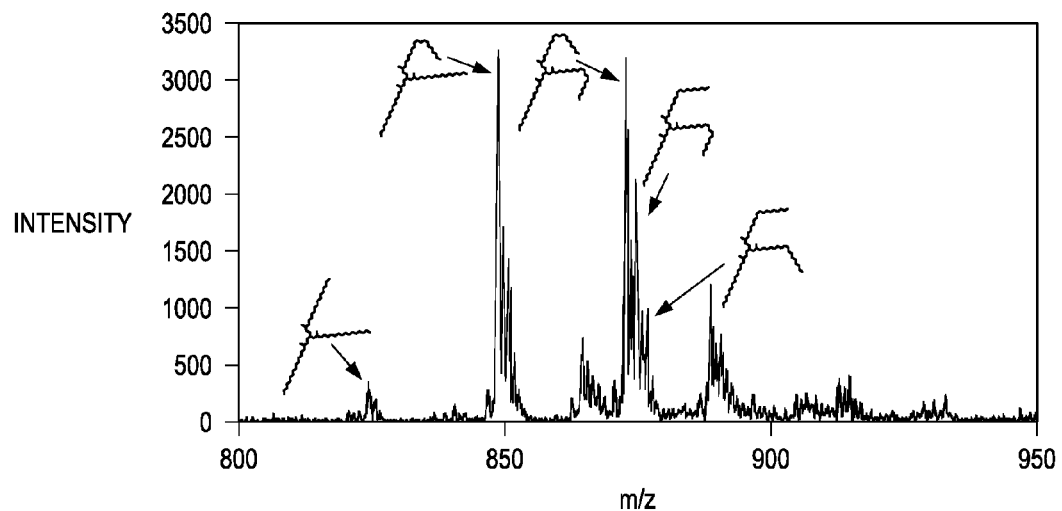
FIG. 15B is a mass spectrum of triacylglycerols extracted directly from lipid droplets of cotton seed (Gossypium hirsutum) with chemical structures of corresponding m/z peaks.

Additional studies were designed to profile multiple biomolecules in a complex mixture of industrial relevance. Trioleate (1,2,3-tri-(9Z-octadecenoyl)-glycerol) was used to standardize LPME-NMS under ideal extraction and purification conditions. Although trioleate was not within an aqueous background the compound (liquid at room temperature) is slightly immiscible with static organic solvents inside the pulled tip region of the capillary. Interestingly, upon extraction it was evident that under acidic conditions (2% glacial acetic acid as the protonation source) an acid-catalyzed hydrolysis reaction (FIG. 15A) [32] of the trioleate was taking place within the capillary tip to produce the corresponding diacylglycerol fragment, dioleate (1,2-di-(9z-octadecenoyl)-glycerol) (FIG. 8A). It was also apparent that triacylglycerols had a higher affinity for sodium and ammonium cations than for hydrogen ions present in solution (FIG. 15B).

Figure 14:
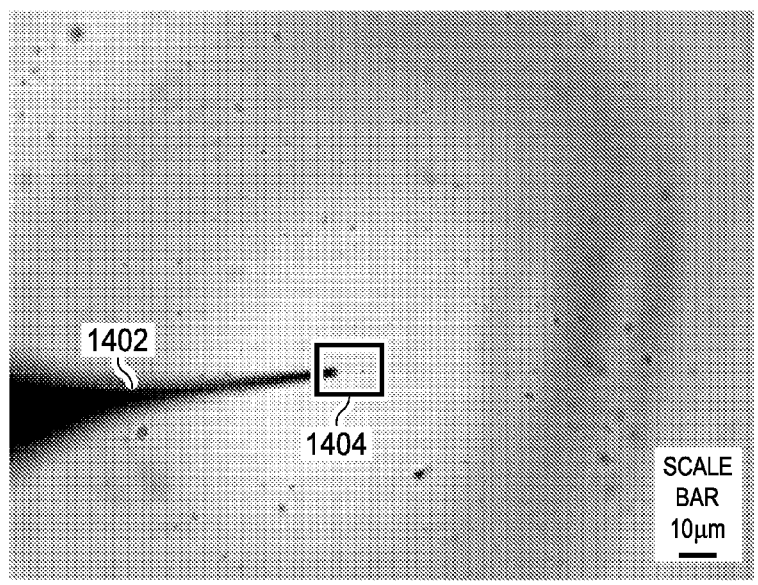
FIG. 14 Bright field image of purified lipid droplets from cotton seed (Gossypium hirsutum) being directly sampled with a nanospray emitter. Scale Bar=10 microns.

LPME-NMS of industrially refined, bleached and deodorized cottonseed oil (FIG. 8C, black lines) was then analyzed under identical extraction conditions as trioleate to demonstrate the profiling of multiple triacylglycerols within a single medium. FIG. 14 is a bright field image of purified lipid droplets (1404) from cotton seed (*Gossypium hirsutum*) being directly sampled with a nanospray emitter (1402). Molecular species profiles of triacylglycerols within cottonseed oil were established by a combination of direct infusion of refined cottonseed oil, oil body extracts of cottonseed embryos under the same ionization conditions (not shown), and previous literature values [33-36]. Under acidic conditions, LPME-NMS of cottonseed oil revealed that the production of diacylglycerols was prominent relative to the concentration of triacylglycerols within a relative short extraction period.

The acid-catalyzed hydrolysis reactions were reduced by substituting 10 mM ammonium acetate (FIG. 8B and FIG. 8C grey lines) as the adduction source. The reproducibility of the technique was evaluated in a separate set of experiments by adding tripentadecanoin (1,2,3-tripentadecanoylglycerol) as an internal standard at $\frac{1}{12}$ the mass of cottonseed oil. Although a solid at room temperature, mild heating at 55° C. of tripentadecanoin within the cottonseed oil produces a homogenous sample before LPME was carried out. Three replicate extractions were carried out for each time point 30, 120, and 240 seconds with the first two minute-scan by NMS (Table 1). The first two minutes of the nanospray allowed sufficient time for the elimination of background ions at the longest time-point and was chosen to demonstrate the reproducibility of concentration within the pulled tip region (BODIPY results above show a multifold concentration in the tip). As expected the absolute abundance of the internal standard and cottonseed oil increased linearly ($R^2$=0.944) over time with the relative concentration of triacylglycerols to internal standard approaching the theoretical amount (Table 1). Hence the LPME-NMS based approach allows for the rapid quantitative analysis of industrially derived, vegetable oil products. Moreover, these studies indicated the expanded utility of monitoring controlled chemical reactions within nanospray capillaries during extraction and direct analysis by NMS.

The variation in extraction efficiency and analyte quantification is likely a consequence of the minimal interfacial interaction, control of the balance pressure bringing the two interfaces together, surface charge effects and limited agitation at the capillary tip opening. Considering that the interfacial area of an average nano-capillary is from ~0.50 to ~1.15 µm2 (diameter 0.8 to 1.2 µm), the mass transfer of the extracted molecule must be significantly large to concentrate the solute within the organic phase. The interfacial area is significantly less than single organic drops with other current methods [36] and pushes the limits for a kinetically favorable transfer event. The extraction conditions above attempted to take advantage of the high solubility between lipophilic compounds and organic solvents as well as a concentration gradient at the interfacial barrier. The balance pressure was manually controlled due to the slight variations within tip diameter. This parameter is the most difficult to control in attempting to force the two interfaces to make contact without essentially injecting a portion of the organic solvent onto the aqueous sample. The surface charge effects are evident with coated nanospray capillaries in complex solutions or cellular material as "debris" tends to migrate towards and attach itself to the tip openings (even with a positive balance pressure at the tip end). The agitation of the capillary tip was relatively mild compared to vortexing during liquid-liquid extraction or microfluidic devices. The velocity with which the capillaries move through the sample could likely be increased to simulate a more vigorous extraction. Nonetheless, inclusion of internal standards in the samples demonstrates the accurate quantification capabilities of this small-volume approach.

TABLE 1

Reproducibility of LMPE-NMS for extracting cottonseed oil.

| Extraction Time (seconds) | Average Total Ion Count (×10$^7$) | Average Predicted C/S TAG Quantity (g)$^a$ | RSD of Predicted C/S TAG Quantity (%) |
|---|---|---|---|
| 30 s (n = 3) | 1.8 | 0.113 | 1.4 |
| 120 s (n = 3) | 3.7 | 0.125 | 2.0 |
| 240 s (n = 3) | 10.8 | 0.142 | 0.5 |

C/S—Cottonseed Oil,
TAG—Triacylglycerol,
RSD—Relative Standard Deviation
$^a$The average predicted cottonseed TAG quantity extracted was determined through back calculation of absolute peak areas versus a known quantity of internal standard.

Figure 13A:
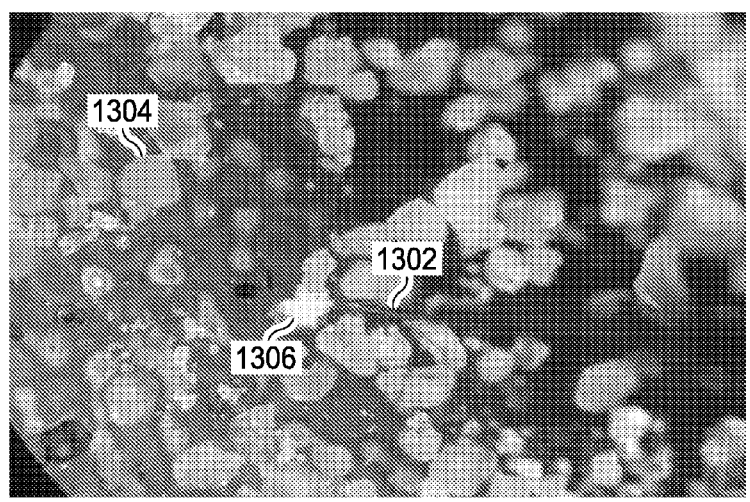
FIGS. 13A-13D show.
Figure 13B:
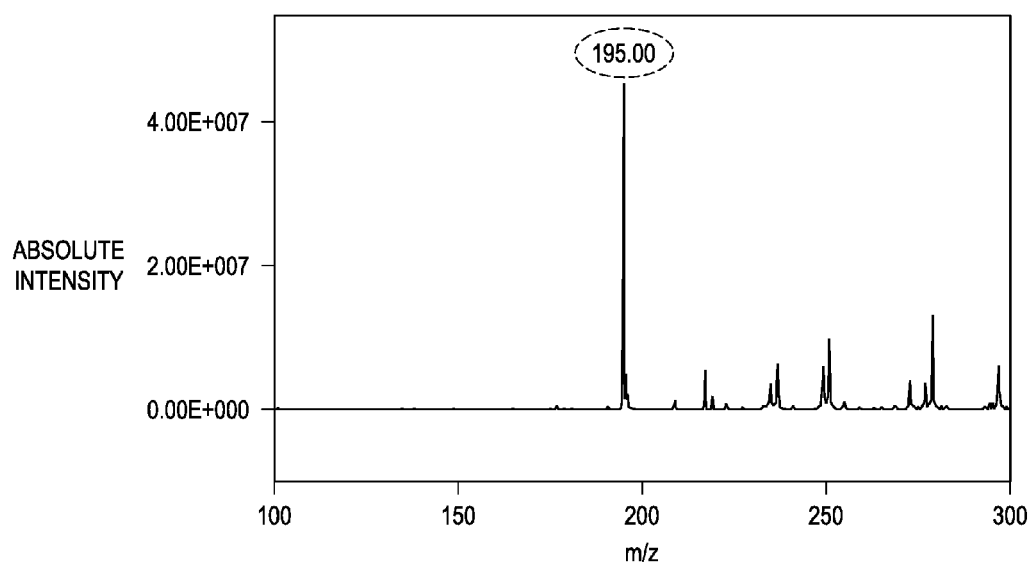
Figure 13C:
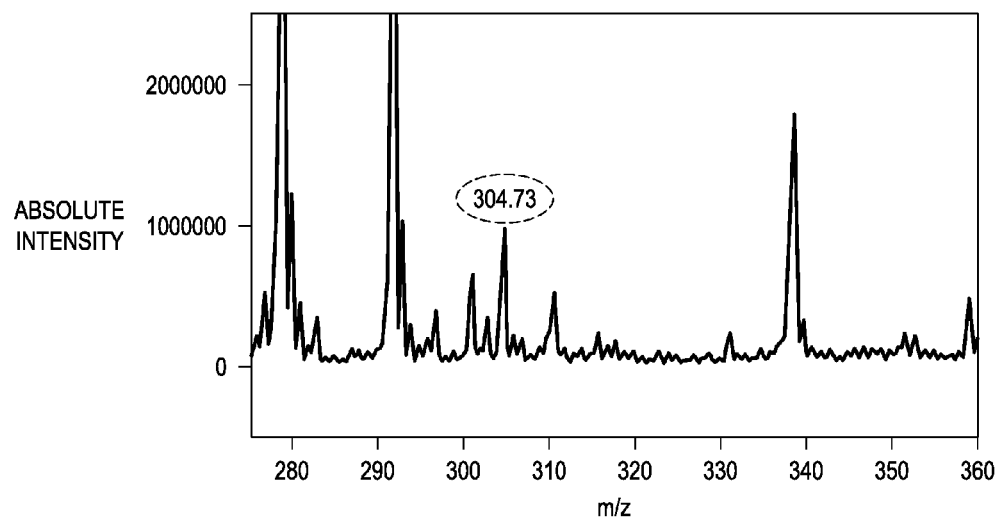
Figure 13D:
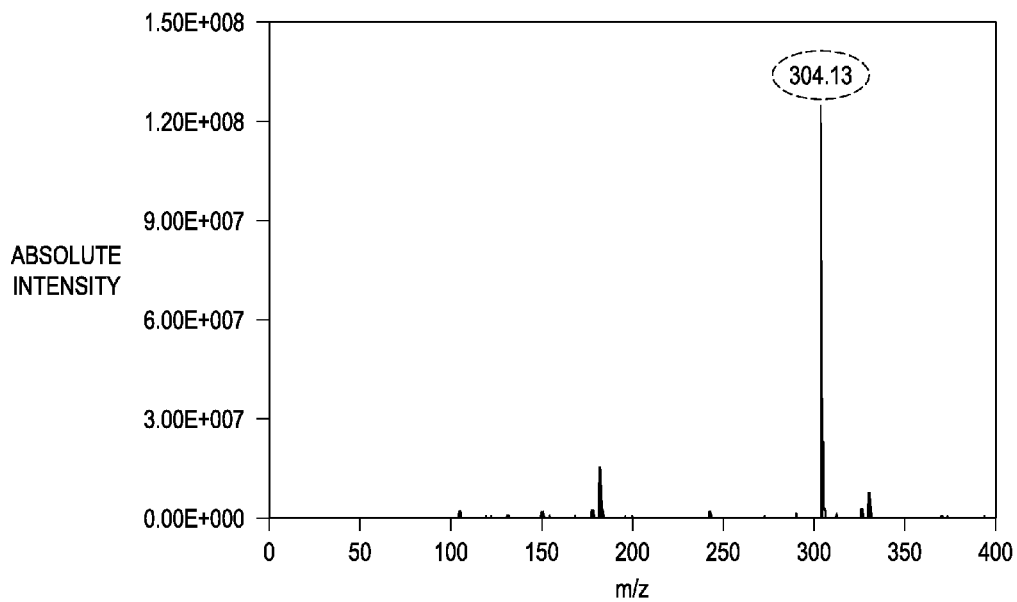

The present inventors have described a novel instrument and a method of nanomanipulation coupled to NSI-MS as an effective tool to analyze trace analytes found on fibers, with the successful analysis of cocaine. The inventors recovered trace particles of cocaine from rayon fibers using the nanomanipulator and subsequently analyzed the trace by directly taking the sample from the nanomanipulator to the NSI-MS (FIGS. 13C and 13D). The inventors have also successfully analyzed caffeine using the method described herein (FIGS. 13A and 13B). In FIG. 13A the particle of interest (1306) is combined with a soil mixture (1304) and electrostatically lifted. The nanospray capillary (1302) is placed near the analyte particle for extraction. These examples clearly demonstrate the functionality and utility of the nanomanipulator coupled to NSI-MS to improve upon the current methods of analysis of trace analytes found on fibers. In the field of trace analysis, preconcentration techniques produce only positive results for metal chelates; therefore, a better option might be a preconcentration technique like evaporation, extraction methodologies, or changing the sampling procedure to obtain a more concentrated sample [17]. Advantages of NSI-MS include having the capability to analyze samples with limited volumes (as low as 300 nL) and low limits of detection and would eliminate the need for any such preconcentration technique.

Figure 16:
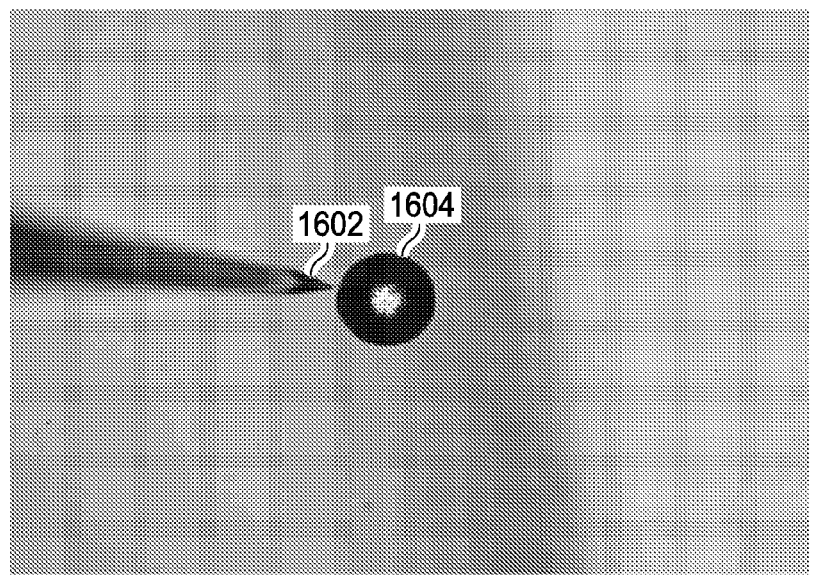
FIG. 16 shows a NSI tip landed near peptide coated solid support.
Figure 17A:
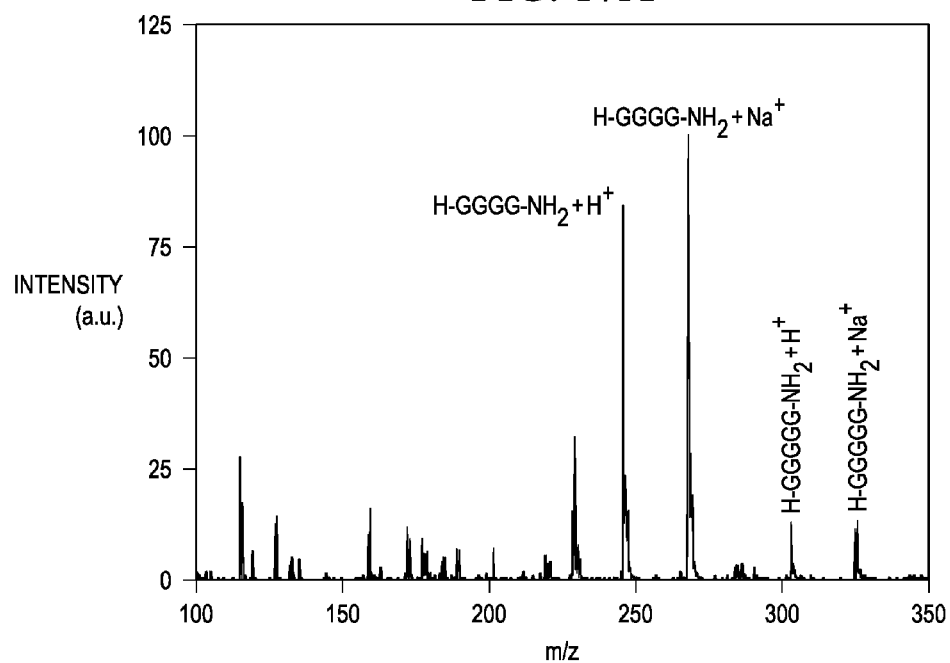
FIG. 17A is a mass spectrum of a polyglycine peptide sequence bulk sample as analyzed by NSI-MS.
Figure 17B:
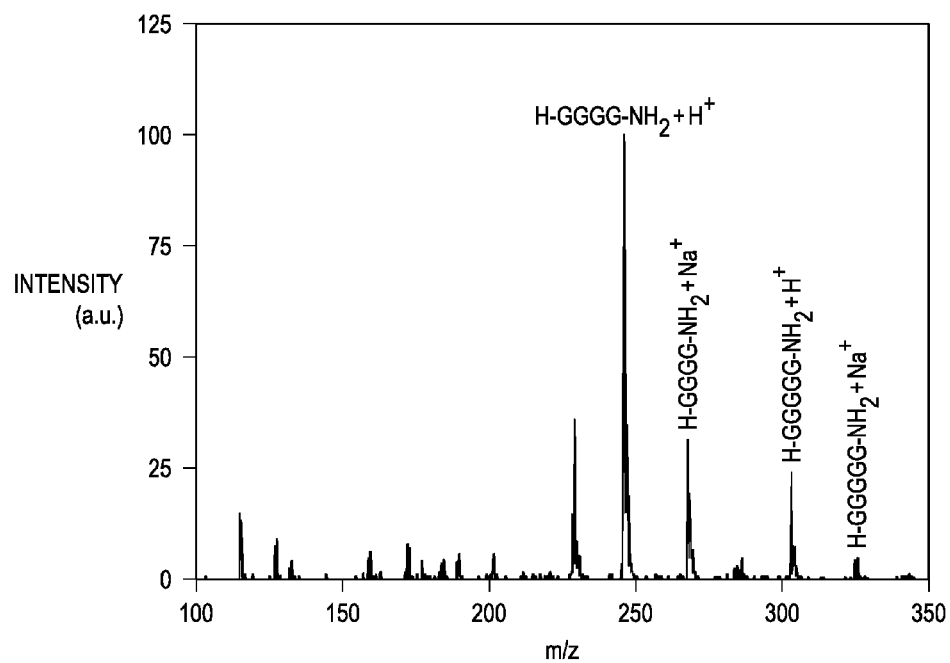
FIG. 17B is a mass spectrum of a polyglycine peptide sequence single bead as analyzed by NSI-MS.

Some applications of NSI-MS are shown in FIGS. 16, 17A, 17B, 18A, and 18B. FIG. 16 shows a NSI tip (1602) landed near peptide coated solid support (1604). FIGS. 17A and 17B show mass spectra of a polyglycine peptide sequence bulk sample and a polyglycine peptide sequence single bead analyzed by NSI-MS, respectively. FIGS. 18A and 18B show comparative mass spectra of H-PWSG-NH2 as analyzed by ESI MS/MS and NSI MS/MS, respectively.

The inventors further describe a LMPE-NMS approach to rapidly sample complex mixtures of industrial, chemical, and biological materials for compositional analysis. The implementation of a few design modifications such as improving the effective interfacial area, balance pressure, and agitation of the extraction would result in additional quantitative ability for reproducibility and quality control. Industrially, the technique described hereinabove could be an alternative method to quickly sample compounds that are only produced in micro-quantities in a minimal number of steps eliminating sampling methods that traditionally result in significant analyte losses. Chemically, the technique could be used to monitor reactions of a compound that became selectively extracted upon production. Finally, the L200 nanomanipulator system, with control of multiple end-effectors (FIG. 1A) of the present invention also provides the possibility of performing LMPE-NMS within miniaturized biological systems as a system to profile compounds by selective extraction while visualizing samples.

EXAMPLE III

Retrieval of Drug and Explosive Residues

Figure 12A:
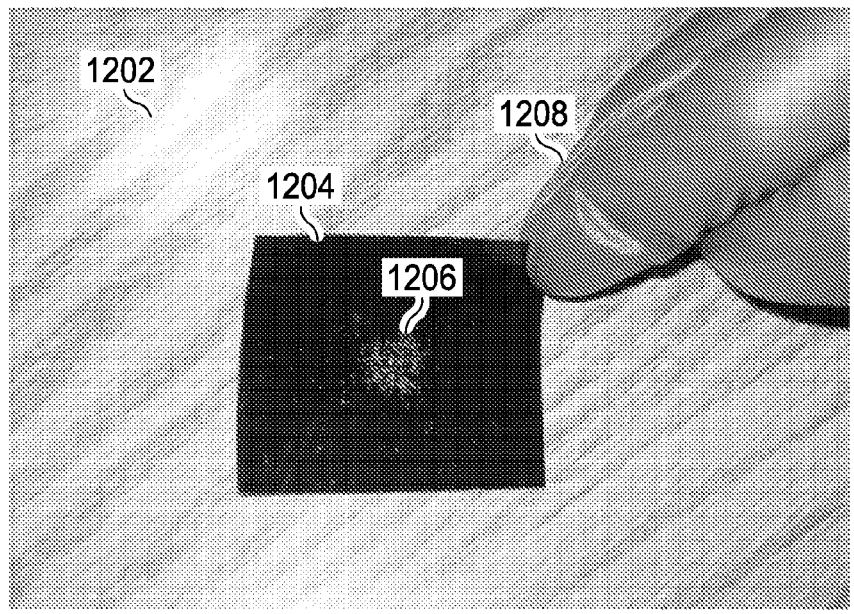
FIGS. 12A and 12B show a caffeine/soil lift done with the electrostatic lifter.
Figure 12B:
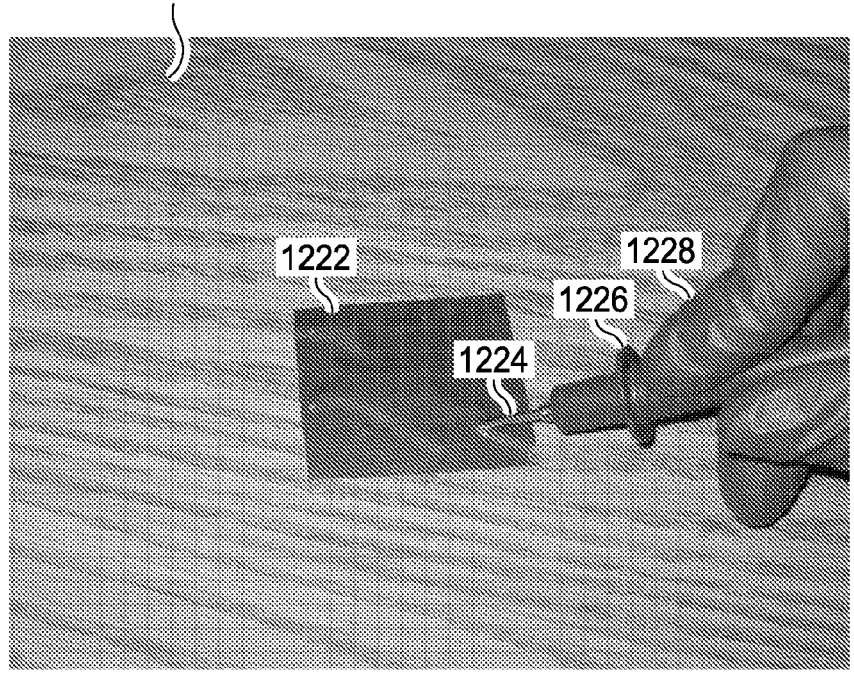

The retrieval of drug and explosive residues in ultra-trace amounts poses a challenging task for most trace analysts due mostly to instrumental limitations. The instrumental analysis of ultra-trace amounts serves as a hindrance to obtaining productive results. Detection of extremely small quantities is usually beyond most operational standards of instruments and cannot be done with quality results. This issue has prompted the development of techniques combined with instruments to achieve quality results that include higher sensitivity and selectivity of analytes. However, the retrieval of drug and explosive residues from fingerprint impressions is a method that does not receive much attention. Although there are many techniques that can image the friction ridge detail of fingerprint impressions, not many advance their techniques to the extraction of particulates contained by impressions. Electrostatic lifting applies the concept of imaging the particulates of soil and other particles (1206) to outlining the footwear impressions made on surfaces (FIGS. 12A and 12B). In FIG. 12A The mylar film (1204) is used to electrostatically lift particles (1206) from a surface (1202) by hand (1208). In FIG. 12B the voltage insulator (1226) houses the probe (1224) used to apply voltage to mylar film (1222) which is placed on top of the surface (1220). The present inventors have used ruthenium tetroxide (RTX) as a developing technique and not just as a powder. Fingerprinting makes use of different types of powders specific to developing fingerprints in order to record friction ridge detail. Chemical imaging of trace amounts of residue from fingerprints as been implemented in the identification of analytes according to their chemical signature exhibited in spectra through the use of infrared spectromicroscopy [37]. However, since most impressions are made at the scene of the crime, it is not always a simple task to retrieve these particles for analysis. The amount that is there may not be enough for analysis as well. The modification of GC-MS method is another technique that has been implemented to facilitate the preparation of residue components of fingerprints in order identify analytes present [38]. This method still requires a certain amount of preparation of the components retrieved before instrumental analysis can commence.

The detection of ultra-trace amounts of explosives is a task that often becomes daunting due to the multiplicity of factors involved in doing explosives analysis. The chemical makeup of explosives varies tremendously making it very difficult to use a standard method of analysis [39]. Solvent systems often vary according to type of explosive and instrumental method utilized. There is a multitude of instrumentation designed for explosive residue detection each implementing a unique methodology of analysis. Most of these types of analysis are elemental based to identify components in the explosive mixtures so as to pinpoint one particular type of explosive. A range of technical approaches have been researched and tested toward the improvement of explosives analysis. One strategy utilizes laser-induced breakdown spectroscopy to identify trace amounts of explosive components [40]. However, this is a destructive technique that does not allow reprieve if not utilized correctly the first time. Much analysis time does go into this type of sensor technology to correlate results. The method also has to take into account specific factors such as oxygen and nitrogen exposure from the air and also has to make modifications of the type of gas flow to the instrument in order to obtain spectra from residues.

Nanomanipulation-coupled with nanospray ionization provides a straight forward approach to drug and explosives analysis. Crystal extraction provides an ample signal for detection of ultra-trace amounts of analyte residue. Sensitivity and selectivity has been demonstrated with this instrumental technique along with other hyphenated techniques to this instrumentation. The benefits of approach include the elimination of sample preparation along with immediate analysis. This technique is minimally destructive and offers the ability to utilize optical imaging techniques to improve the identification of chemical analytes.

Figure 19:
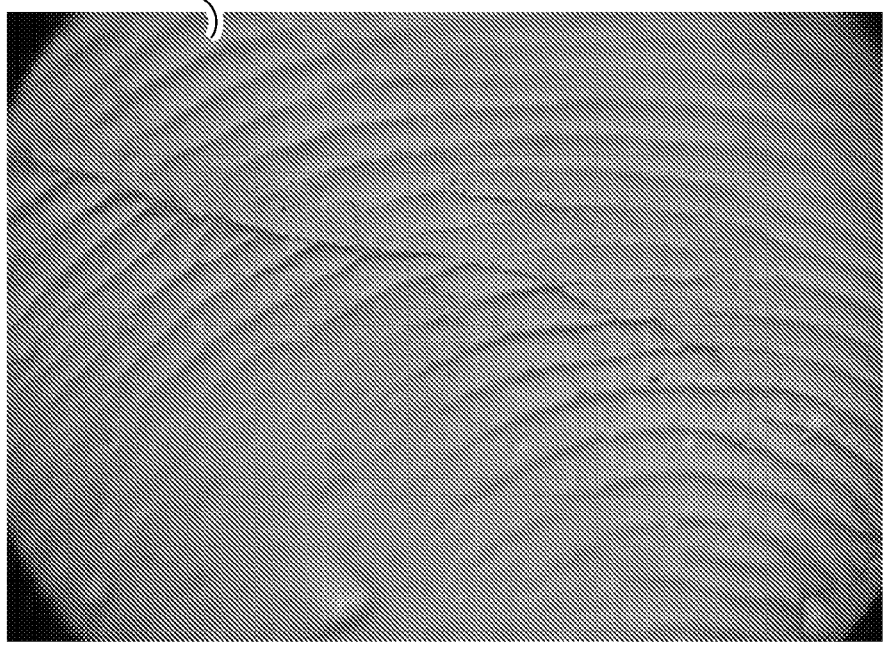
FIG. 19 shows a microscopic friction ridge detail captured up close.

Ultra-trace amounts of drug and explosive residues were lifted with a cast of a finger impression made from a casting material. The purpose of this casting material was to reproduce the friction ridge detail (1902) that would be visibly found on a human finger (FIG. 19). The finger cast was utilized to attract the chemical residues imitating the same method used for taking fingerprints. The finger cast was slightly saturated with a cooking spray oil to imitate the oils naturally secreted from the eccrine glands on the skin's surface of the finger. The chemical residues were lifted off a microscopic slide with the saturated finger cast and impressed onto another slide for nanomanipulation-nanospray ionization. The drug and explosive residues were lifted in this manner to mimic the transfer of residue to the finger that could be theoretically done in a real life scenario.

Figure 20:
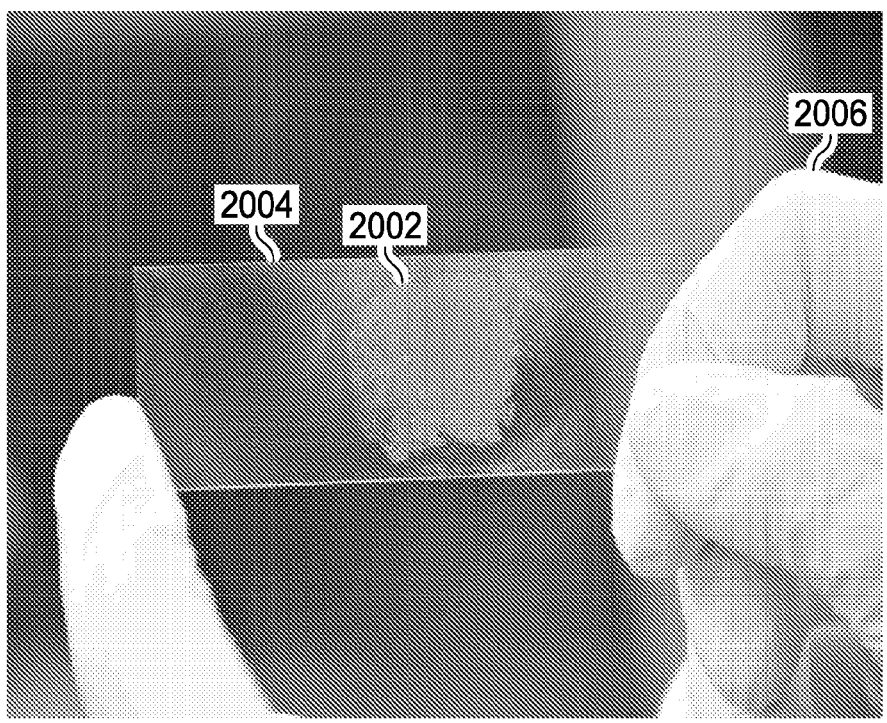
FIG. 20 shows a fingerprint lift of cocaine/red fluorescent powder.
Figure 21:
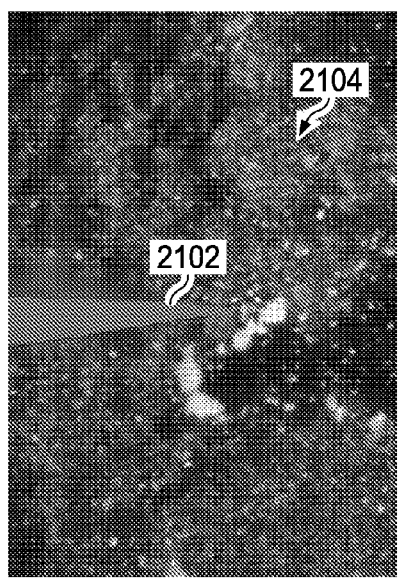
FIG. 21 shows cocaine extraction from fingerprint lift.
Figure 22:
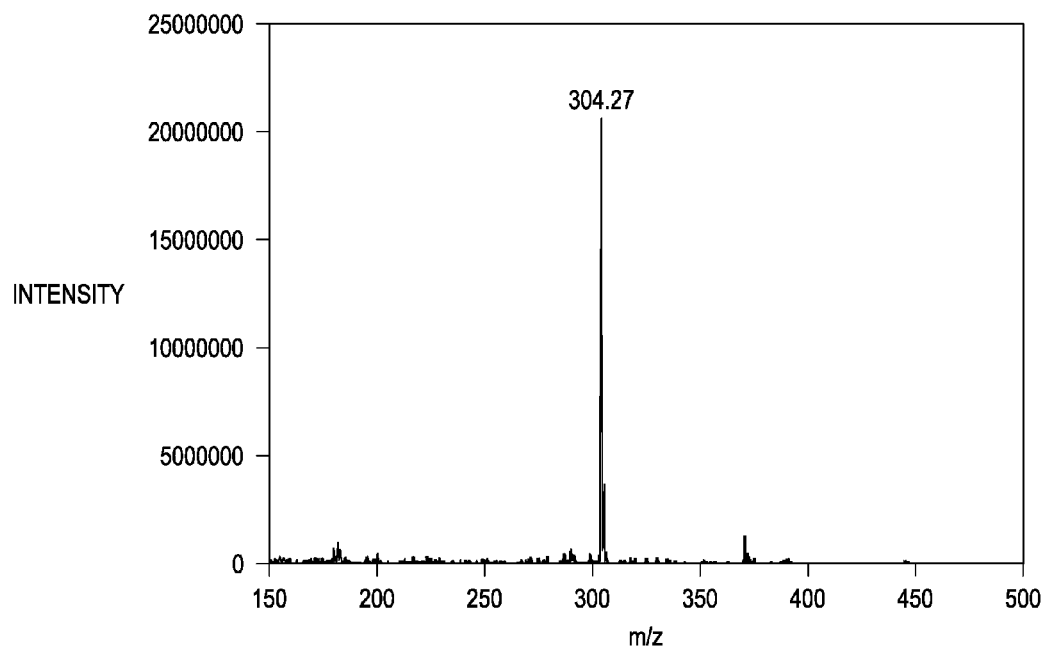
FIG. 22 is a NSI-MS Cocaine Extraction Spectrum. Parent ion peak is at m/z 304.27.

The drug utilized in this study was powder cocaine in the amount of <0.0050 g. The drug was uniformly mixed with red fluorescent fingerprint powder (2002) prior to lifting (FIG. 20). UV fluorescence imaging was done on this uniform mixture (2002) to investigate the possible verification of cocaine among a fluorescent powder matrix (not shown here). Extraction of the drug residue from this uniform mixture (2104) took place with nanomanipulation-coupled with nanospray ionization-mass spectrometry (NSI-MS) (2102) following UV fluorescence imaging (FIG. 21). The instrument settings for NSI-MS analysis were 2 kV for the voltage utilizing 10 µL of a 50:50 methanol/water solution with 1% acetic acid for extraction. The MH$^+$ peak for cocaine was seen at m/z 304.27 on the NSI-MS spectrum (FIG. 22). Spectra were also taken on various types of fingerprint powders to obtain a background spectrum for each powder to examine any interferences to the drug analyte (data not shown). Background spectra were taken from red and orange fluorescent powders as well as white and black powders. The analysis was done with ESI-MS in order to do dilutions of each powder. The mass range was kept the same as the powder cocaine in order to examine any interferences to the MH$^+$ peak of the drug analyte. The dilutions were kept at a 1/10 concentration using a 50:50 methanol/water solution with 1% acetic acid.

The ESI-MS spectra of each powder ran for two minutes in positive mode at 5 µL/min with a voltage of 4 kV. An ESI-MS spectrum was also taken of the cooking spray oil using the same procedure as the fingerprint powders (data not shown). The purpose was to examine any interference from the cooking spray oil as well. The spectra for most of the powders and cooking spray oil show very little indication of interference.

The explosive residues utilized in this study were nitroglycerine (NG) and dinitrotoluene (DNT) stored in methanol. An amount of 10 µL from each explosive solution (1 mg/mL) was evaporated off to retrieve the solid residue particles. The lifting and extraction of these particle residues followed the same procedure as the powder cocaine. The settings for NSI-MS analysis were a voltage of 2.5 kV utilizing 10 µL of solution. NSI-MS analysis for the explosive residues ran for 2 min each in negative mode for NG. The solution mixture containing 5 µL of NH4NO3, 10 µL of NH4Cl, and 100 µL of methanol/water solution with 10 µL of acetic acid was utilized in the extraction process. The purpose of this solution mixture was to form the adduct peaks with the explosive residues to exhibit the presence of the explosives residue due to instability of the parent ions. For DNT the solvent used was 500 µL methanol, 500 µL water containing 1 mg of ammonium acetate. 10 µL of this solution was used for NSI-MS analysis. The spray voltage was 2.0 kV, the scan time was 1 min in the negative mode. NSI-MS spectra were obtained on each explosive residue prior to the finger print lift studies to gather standards for comparison.

EXAMPLE IV

NSI-MS for Drug Residue Extraction Coupled to Surface Enhanced Raman Scattering (SERS)

The method of residue extraction through electrostatic lifting provides a distinctive mode of performing ultra-trace analysis. These lifts provide a medium for analyte extraction via NSI-MS. This method of extraction can be coupled to Raman spectroscopy for supplemental verification of analytes using surface enhanced Raman scattering (SERS). The gold surface used for SERS provides an enhanced effect on peak signal intensity allowing ultra-trace amounts to be detected more effectively. The gold plating of electrostatic lifts allows for a two-fold method of analysis incorporating improved detection of ultra-trace amounts along with selective probing of the desired analyte.

Raman spectroscopic methods are conventionally utilized for spectral analysis of small and large compounds in limited amounts. The method is nondestructive in nature and normally requires no sample preparation, making it very efficient. The methods employed provide increased sensitivity of analyte detection. Many of these Raman spectroscopic methods have been advanced to provide ultra-trace detection of analytes by modifying the surface which analytes are absorbed or adhered to for analysis [41]. They have also been coupled to other techniques to improve overall analysis and sensitivity of detection. Surface enhanced Raman scattering (SERS) has come about to provide improved peak signal intensity from samples analyzed [42]. Enhancement of the Raman signal with metal substrates has been studied to understand the effect of light and metal surface interaction as to improve signal intensity of the analytes [43].

The technique has been implemented in a wide range of analytical applications utilizing and experimenting with various metal substrates[44]. For single particle analysis, colloidal silver solutions have been utilized and shown to enhance detection of analytes [45]. SERS has been employed in many types of small and large molecule analysis as well as various types of applications involving bioselective species[41]. The modification of antigens with gold nanoparticles has been demonstrated with SERS to track antibody production, detection was exhibited in the femtomolar range [46]. Selective capture of particular disease causing bacteria by antibody production has been shown using SERS exhibiting an increased cell readout of 630 to 740 cells/mL in the appropriate buffer solution[47]. Chemical change induction of bacteria by antibiotics has been monitored using a developed SERS-active substrate for analysis [48].

Raman spectroscopic analysis has been incorporated in the characterization of various illicit drugs in trace and ultra-trace amounts. The spectroscopic method is versatile in accommodating various drug analysis procedures. The detection of cocaine in solid particle mixtures has been performed using Raman spectroscopy implementing principal component analysis to facilitate quantitation[49]. This method of analysis provides a technique for obtaining effective quantitation of illicit drugs in mixtures utilizing Raman spectroscopy. Cocaine residue on human nail surfaces has been examined with Raman spectroscopy coupled with confocal microscopy to view the particles through a nail varnish matrix[50]. This method examined a way to improve analysis by eliminating the matrix effect of the nail varnish toward analysis. The heighted attention of the SERS method has lead to the research and development of methods that improve illicit drug analysis. For instance, the examination of gold and silver colloidal suspensions used in SERS to detect amphetamine sulfate has been conducted to compare both in regards to Raman signal enhancement and surface adsorption[51]. The screening of ecstasy tablets has been successfully performed to detect relative amounts of MDMA present in various tablets utilizing silver colloids[52]. The development of improved metal substrates has further advanced the SERS method. Identification of trace amounts of morphine, codeine, and hydrocodone have been detected with SERS using silver nanoparticle substrates to enhance signal intensity and eliminate fluorescence of these compounds[53]. The use of silver halide matrices has been implemented for the detection of amphetamine in confiscated drug tablets[54]. The coupling of the SERS method with other instrumental methods has been developed as well to advance the improvement of drug analysis especially when dealing with biological matrices. Trace amounts of narcotic drugs in biological fluids have been detected with SERS coupled with high performance liquid chromatography (HPLC) as a way to achieve more sensitivity by reducing the matrix[41]. Many pharmaceutical companies favor the SERS method over other analytical methods due to the overall efficiency and effectiveness of the procedure. SERS is ideal for pharmaceutical drug analysis due to the fact that no sample preparation is required and that analysis of samples can be done in either the solution based or solid form of the analytes in a steadfast manner[55]. The fact that polymorphic behavior of drugs can manifest during spectral analysis provides another reason for pharmaceutical companies to employ SERS[56]. Increased sensitivity can still be achieved while avoiding this issue. The SERS technique has also been implemented in the procedure for cleaning pharmaceutical manufacturing equipment in order to verify cleaning by industrial standards[57]. The coupling of SERS with nanomanipulation has been implemented to provide supplementary characterization of drug analytes. This coupled method has been done to characterize drug analytes on 50 nm gold-plated electrostatic lifts to verify their adherence to the lift via electrostatic lifting[58]. Spectra of these drug analytes have been collected in our lab using SERS to provide parallel verification with NSI-MS in other studies.

Electrostatic dust lifting is a method that is utilized in the lifting of prints from many types of surfaces. Surfaces range from a table top to the body of a deceased. The electrostatic lifting process involves the use of a high voltage instrument to apply an adjustable voltage to the metallic side of a Mylar film to lift dust particulates off a surface[59]. Normally the use of the electrostatic lifting process is reserved for crime scene investigations to record prints left on a surface[60]. Results with the electrostatic dust lifter are usually achieved with ease and great success as compared with other dust print lifting devices[61]. The technique of lifting dust prints has been modified to lift drug particulates in the present invention. The chemical extraction of drug analytes from these electrostatic lifts are being performed with nanomanipulation as opposed to the traditional photography utilized in the recording of ridge detail. The electrostatic films were coated beforehand with gold to enhance peak signal intensity of the drug analytes present in the soil matrix for the performance of SERS.

The gold-plating of the electrostatic films for spectral enhancement used in SERS allows for the desired analyte to be detected among a background matrix. The combination of electrostatic lifting with SERS provides an inventive approach to performing trace and ultra-trace analyses of drug particulates. The approach is fast and effective, eliminating the need for sample preparation. This coupled technique has the potential to expand to other types of trace work that require solid particle retrieval and analysis. The combined method can also be employed with other types of trace methods such as nanomanipulation.

For the electrostatic lifts, Mylar® film (DuPont Wilmington, Del.) was used as the lifting substrate and a Pathfinder lifter (CSI Equipment ltd. Woburn Sands, England) was used to apply voltage to the films during the lifting procedures. For SERS, gold was deposited on the films in 25, 60, and 100 nm layers using chemical vapor deposition. Raman SERS spectra were obtained using a T64000 triple-grating Raman instrument (HORIBA JobinYvon Inc. Edison, N.J.), which focused on the sample surface through a 100× microscope objective. Excitation was accomplished with a 532 nm diode-pumped solid-state laser (QED Lasers), attenuated to approximately 34 mW. Backscattered light was captured with the objective, guided through the spectrometer and detected using a liquid nitrogen cooled CCD camera.

Caffeine was used to validate the procedure and to probe the effectiveness of the gold-coated films for use in SERS analysis. First, a small quantity of pure caffeine (<0.003 g) was placed on clean countertop and a 1.0 in2 sheet of Mylar® was placed over it. Voltage was then applied to the film with the lifting apparatus for twenty seconds in order to retrieve the caffeine. The sample was then observed under the Raman microscope, and particles of approximately 1-3 μm in diameter were chosen for spectral analysis (unless otherwise noted). This procedure was repeated for each of the gold-plated films.

To test the selectivity of the lifting procedure, small quantities of caffeine (<0.003 g) and soil (~0.020 g, primarily sand) were mixed and then lifted with Mylar® and the gold-plated films. The films were weighed before and after each lift in order to determine the amount of material collected. Raman was used to analyze the lifted material. This procedure was then used to lift and analyze samples of rock cocaine, crystal meth, and ecstasy provided by the University of North Texas Police Department (Denton, Tex.).

An area of the gold-plated film (60 nm) containing both sand and cocaine particles was selected for the imaging experiment. Spectra were collected at 5.0 μm increments in a 60 μm by 80 μm grid and baseline corrected. Of the resulting spectra, the intensity of the cocaine peak at 1004 cm$^{-1}$ was used to create a contour plot of the area imaged.

Quantitative amounts of gold (25-100 nm films) were deposited on the Mylar® in order to strike a balance between the lifting effect of the substrate and the SERS enhancement from the gold. All of the gold-coated films preferentially lifted analyte particles and only trace quantities of soil. The sizes of the analyte particles that were lifted varied from roughly 0.5 mm to 1.0 μm in diameter. Overall, this might suggest that the electrostatic properties of the organic analyte particles are more accommodating to the gold substrate due to a higher polarizability over the soil matrix. This effect may also be augmented by the conductive nature of the metal film.

Given the tendency of the gold-coated films to selectively lift the organic analyte (2304) particles as opposed to the soil matrix (2302) from a solid substrate, support or any solid surface (2308), a two-step approach (FIGS. 23A and 23B) (2300) would act to further improve this method. In this instance, the print can be lifted using an uncoated film, effectively collecting both the analyte (2304) and matrix particles (2302) comprising the print. This could be directly followed by a second lift performed by covering the initial lift with a gold-coated film (2306) and applying voltage (2310) to collect latent drug residues. This would provide both an effective print lift, and a substrate on which to collect and analyze the drug residues via SERS.

Figure 24:
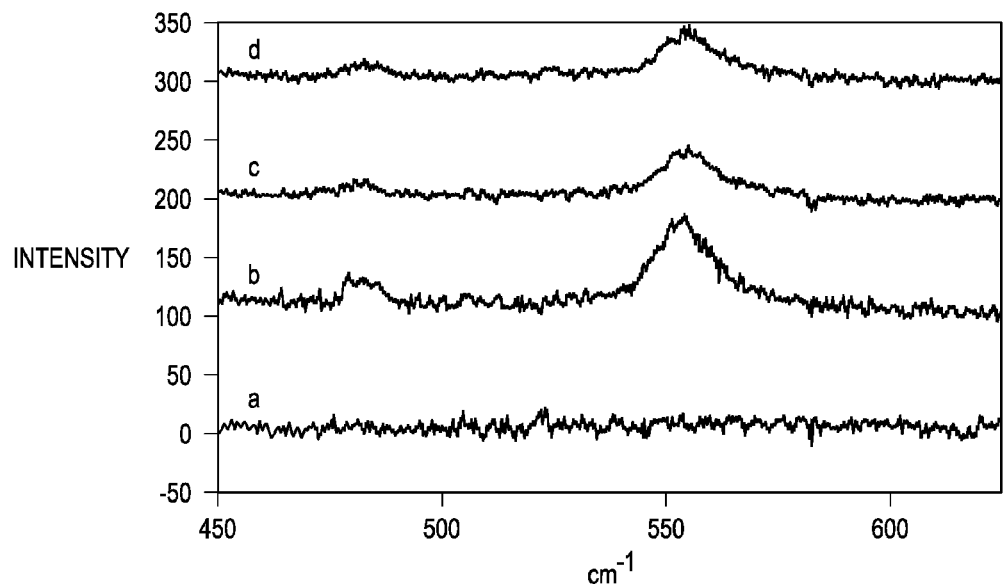
FIG. 24 is a Raman spectrum for the caffeine standard on a) Mylar® film, b) 25 nm gold film, c) 60 nm gold film and d) 100 nm gold film.
Figure 25:
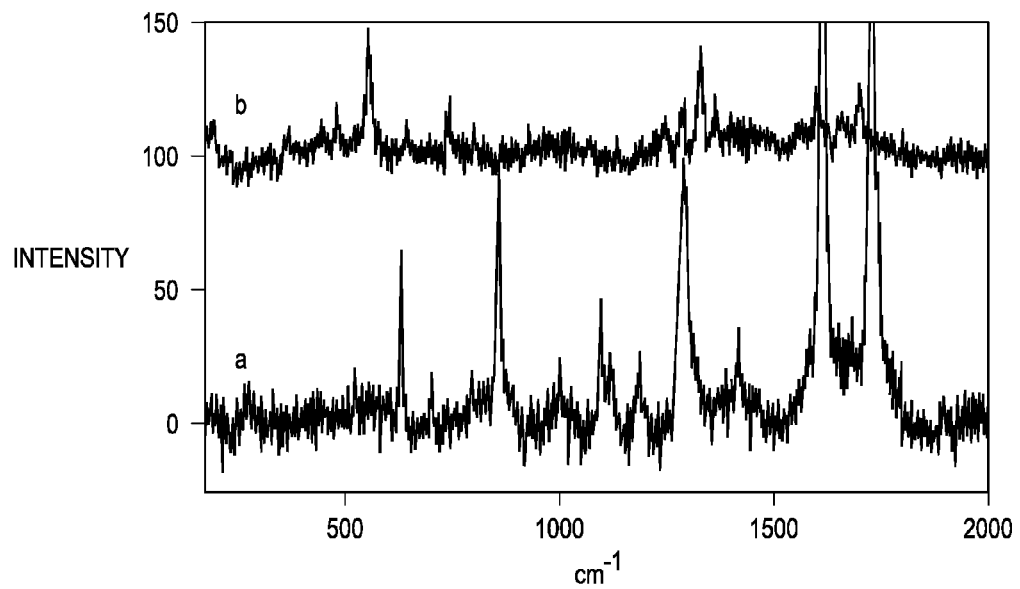
FIG. 25 is a comparison of the full spectra for a) caffeine on Mylar® and b) caffeine on the 100 nm gold film.

FIG. 24 shows the spectra obtained from the caffeine lifted on the four films. On the uncoated Mylar®, only peaks characteristic of the film itself are observed. The spectrum from the 25 nm gold film displays the larger peak from caffeine (at 551 cm-1). At 60 and 100 nm gold coverage, the peaks arising from the film have been fully suppressed, and the caffeine signal is readily identifiable. Full spectra, showing the suppression of the Mylar® Raman signals, can be seen in FIG. 25 for the caffeine on Mylar® and the caffeine on the 100 nm gold film. The spectra from the caffeine-soil mixture showed no notable differences from the caffeine standard and have thus been omitted. There was a notable increase in the mass of lifted particles on the uncoated film, however the mass of particles lifted by gold-coated films still could not be determined due to the trace quantities recovered.

Figure 26:
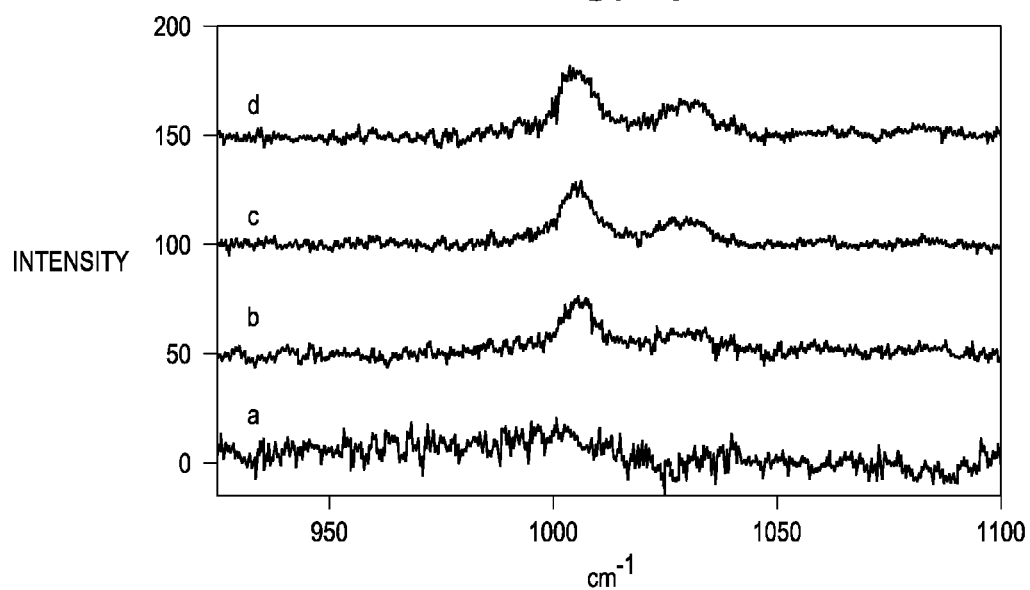
FIG. 26 is a Raman spectrum for cocaine on a) Mylar® film, b) 25 nm gold film, c) 60 nm gold film and d) 100 nm gold film.
Figure 27:
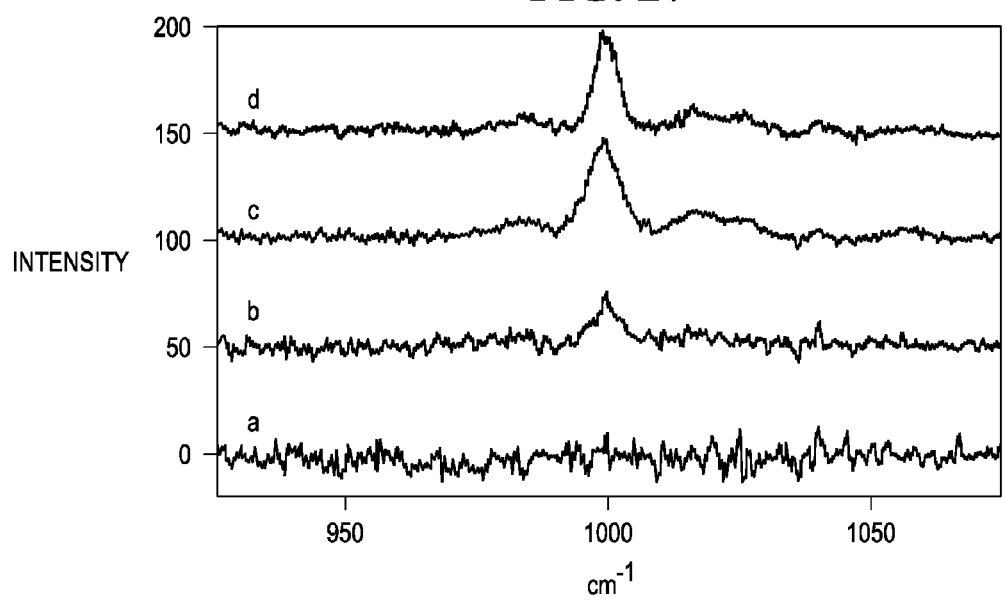
FIG. 27 is a Raman spectrum for crystal meth on a) Mylar® film, b) 25 nm gold film, c) 60 nm gold film and d) 100 nm gold film.
Figure 28:
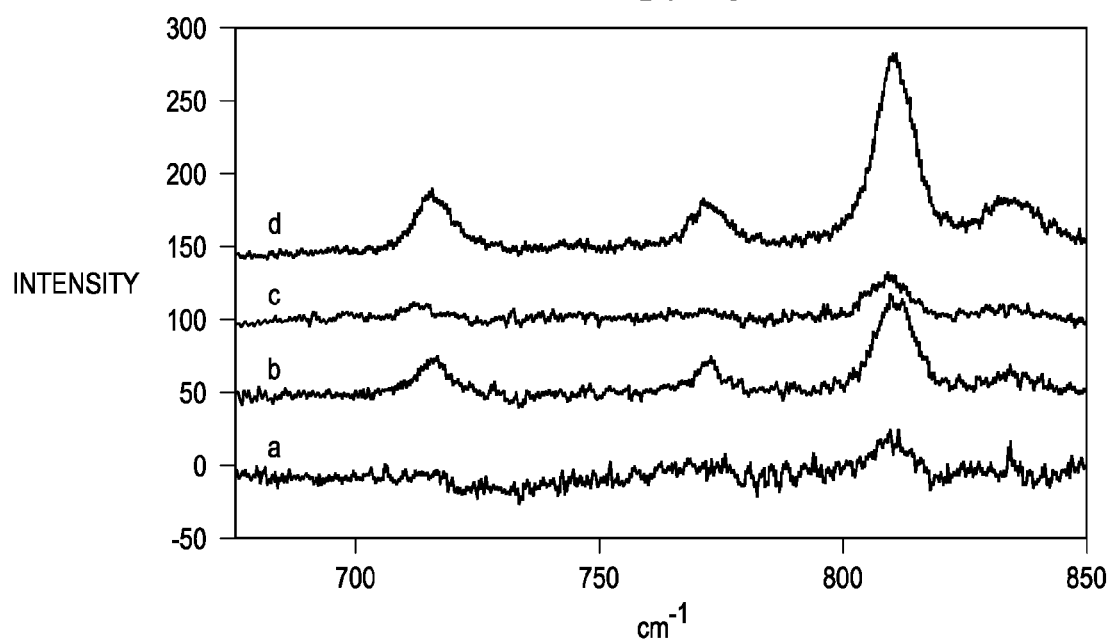
FIG. 28 is a Raman spectrum for MDMA on a) Mylar® film, b) 25 nm gold film, c) 60 nm gold film and d) 100 nm gold film.

FIGS. 26 through 28 show the spectra collected from the mixtures of the drug samples and soil lifted on the four different films. Again, no analyte peaks are observed on the uncoated films with the exception of a small peak at 810 cm-1 in the spectrum for ecstasy. In this case, a significantly larger particle (~10 μm in diameter) was chosen for analysis due to excessive scattering of the laser line and baseline noise in the spectrum. The spectra for the 25 nm films show no signs of the spectral peaks for the film, displaying a successful suppression of the background signal. While this is true, the signal for crystal meth remains low, showing only the most intense peak in the spectrum near 1000 cm-1. The 60 and 100 nm gold films both show enhancements in the Raman spectra of crystal meth and cocaine. The spectrum for ecstasy on the 60 nm gold film shows a marked reduction in signal strength; however, this is likely to be the result of particle selection and not the effect of the gold substrate. Overall, the 60 and 100 nm gold films showed the best consistent enhancement of the Raman signal.

Figure 29:
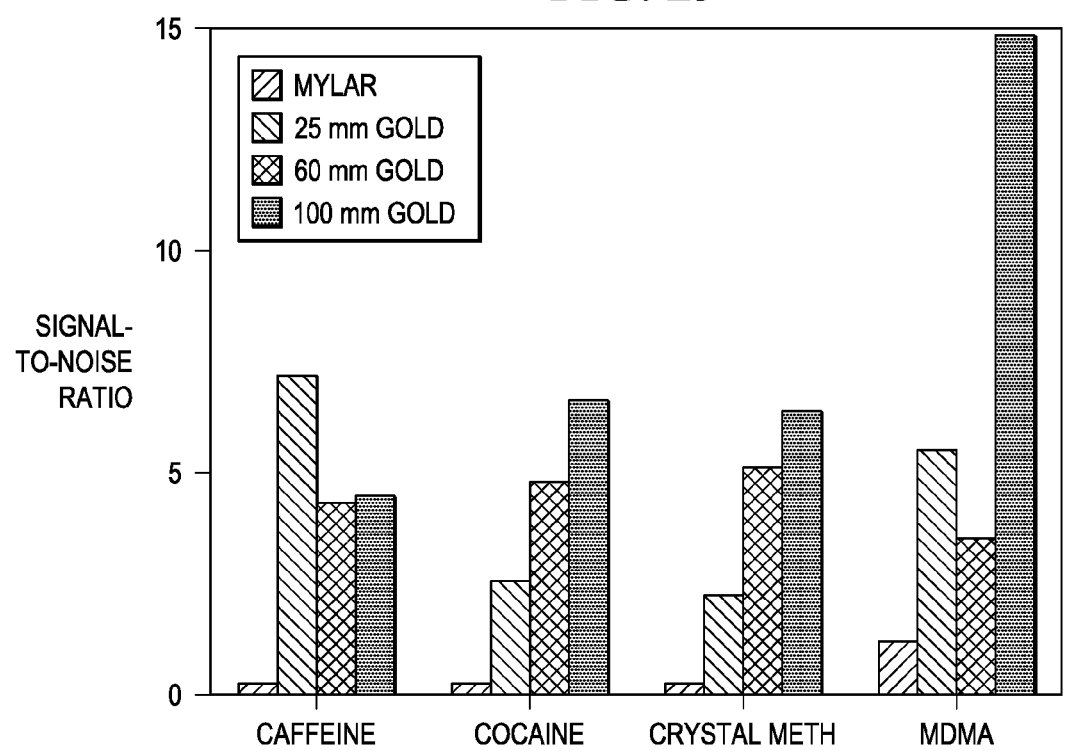
FIG. 29 is a comparison of the signal-to-noise ratios for the four samples on each of the films.

FIG. 29 shows the signal-to-noise ratio (SNR) for the four samples on each of the four substrates. For caffeine, cocaine and crystal meth, the SNR on the uncoated Mylar® is zero, due to the lack of spectral peaks representing the analyte. For the caffeine standard, the 25 nm gold film shows a marked increase in the SNR. It should be noted that the full spectrum on the 25 nm film displayed both spectral peaks for caffeine and the Mylar® film. Only at 60 nm were the peaks from the film fully suppressed. For the three illicit drug samples, it can be seen that the SNR increases with presence of thicker gold layers (with the exception of the aforementioned MDMA sample).

Figure 30A:
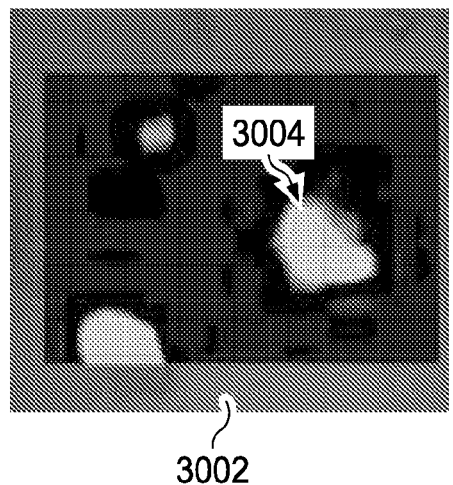
FIGS. 30A-30C are microscope images of the area mapped in the Raman analysis of cocaine and sand (FIG. 30B), contour map overlaid on the image (FIG. 30A) showing areas of cocaine signal in grey and white (the threshold peak intensity for white is 12.23 a.u.), and three-dimensional plot of the Raman image with the microscope image overlaid (FIG. 30C)
Figure 30B:
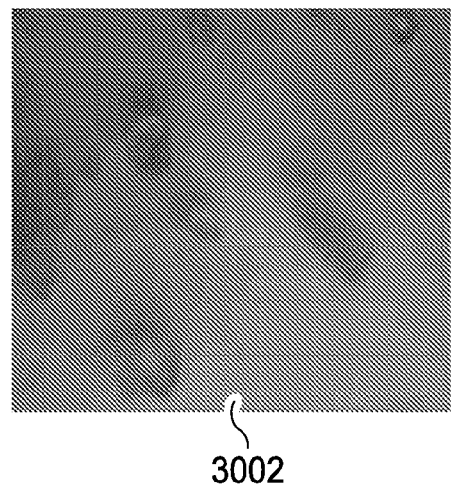
Figure 30C:
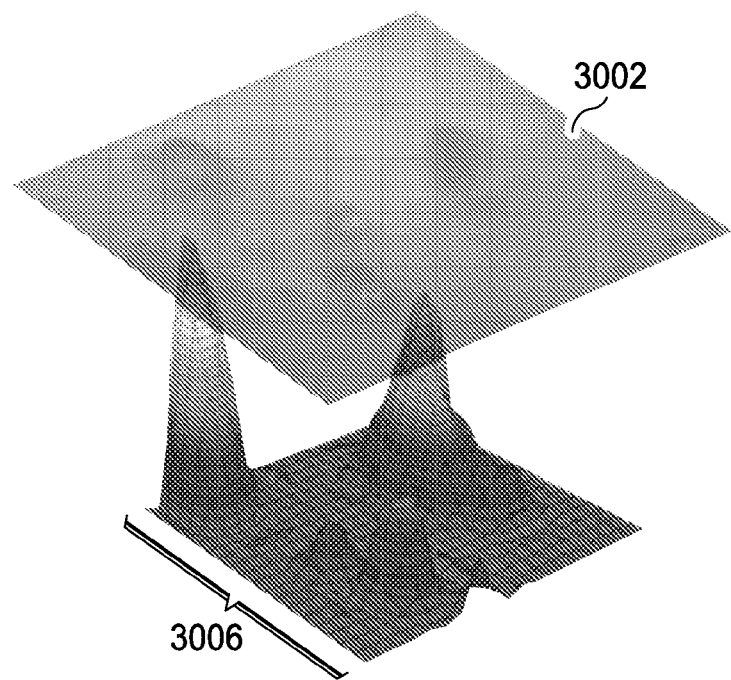

FIGS. 30A-30C show both the microscope image (3002) of the section used in the imaging study (FIGS. 30A and 30B) and the resulting Raman map (3006) of the surface (FIG. 30C). Of the particles visible on the surface, three can easily be identified as rock cocaine (3004) based on the Raman spectra of the surface. This method of screening lends itself to quick identification of the particles and can be followed with additional particle-specific analysis such as nanoextraction and identification with NSI-MS.

The coupling of the electrostatic lifting method with gold-coated Mylar® films has been shown to be an effective process in the analysis of ultra-trace drug residues. By selectively lifting analyte particles over the matrix, the overall time for microscopic screening of the lift contents is effectively reduced. This also lends itself to analyte-specific extraction while keeping the original lifted print intact. In addition to this, the gold coatings on the films provide an effective substrate on which to perform SERS analysis. The analyte spectra display significant signal increases with the presence of the gold films, and the peaks arising from the film substrate are reduced or eliminated.

EXAMPLE V

Direct Identification of Lipid Composition in Lipid Droplets (LDs) by Nanospray Mass Spectrometry LDs are organelles that are specialized for the storage of neutral lipids and as such provide energy-rich reserves in all cellular organisms[62]. Understanding LD ontogeny is of major importance to human physiology; on the one hand, seed oils packaged in LDs make up a growing proportion of daily caloric intake in most diets around the world, and on the other hand, the regulation of lipid storage and mobilization underlies significant human health issues: obesity, diabetes and cardiovascular disease.

Although storage is considered the principal role of neutral lipids, LDs in nonfat storing tissues recently have become more appreciated for their dynamic nature and functional roles independent of storage. These roles include acyl reserves for phospholipid recycling [63], lipid signaling [64], membrane trafficking [63, 65], inflammation and cancer [66], and host-pathogen interactions [67, 68]. These various functions attributed to LDs vary with cell type and likely are manifested by differences in droplet composition. The basic structural model of LDs in plant seeds provides a thermodynamically stable organization that is thought to be conserved throughout eukaryotes, although the nature of the lipids and proteins associated with droplets varies with cell/tissue type. The structure describes a neutral lipid core (triacylglycerols in plant seeds and/or steryl esters in other organisms or cell types) surrounded by a phospholipid monolayer with specific proteins associated with the LD surface[69]. Although the endoplasmic reticulum is considered by most to be the major cellular location for LD biogenesis, droplets associate frequently with other subcellular compartments, presumably to carry out unique functions [70].

The recent emphasis on studying the formation and turnover of these organelles and the importance of this compartment to general cellular physiology has prompted the development of advanced analytical tools for these organelles. Visualization of cytosolic LDs has commonly been carried out by conventional light microscopy and confirmed by histochemical and/or fluorescent neutral lipid specific stains (e.g. Sudan III, Nile Red, and BODIPY derivatives[71-73]. Electron microscopy, such as transmission electron microscopy or freeze-fracture and low temperature scanning electron microscopy, have supported the description of the fine ultrastructure of LDs within various plant and mammalian tissues yielding information on structural variability among an assortment of mutants and under a range of environmental conditions[74-77]. More recently, third-harmonic generation microscopy [78] and high resolution, nonresonant confocal Raman microscopy [79] have been developed to selectively image unstained LDs unveiling novel interactions in complex cellular environments. In combination with two-photon and second-harmonic generation microscopy, third-harmonic generation microscopy offers three-dimensional spatial resolution that can be used to visualize LDs for long periods. Raman-based microcopy can even provide some molecular composition information for LDs within single cells.

The rapidly developing field of lipidomics has led to a renewed effort to analyze triacylglycerol (TAG) prevalence and composition within LDs by mass spectrometric approaches [63]. Many studies have now detailed the complex fragmentation patterns for the complete structural elucidation and quantification of TAGs [80-82]. Supported by advances in bioinformatics (LIPID MAPS) [83], improvements in mass spectrometry, and availability of unique purified standards, it is now feasible to achieve comprehensive lipid identification and quantification directly from complex mixtures. For lipidomics applications, lipids most often are extracted from tissues or cell lines in organic solvents, losing the spatial information of lipid organization within the original sample. Others have combined mass spectrometry with microscopy approaches such as MALDI-MS [84], secondary ion MS (SIMS) [85], and desorption electrospray ionization (DESI)-MS [86] to preserve spatial context with composition information, but the resolution currently remains at the cellular/tissue level, and the compositional analysis is limited and incomplete.

Here, we have developed a novel technique for direct organelle mass spectrometry (DOMS) that couples direct visualization with detailed mass spectrometric analysis of organelles. A multifaceted nanomanipulator, previously demonstrated to extract peptides from a single bead [87] and extract and analyze trace fiber analytes [88], was equipped with glass nanospray emitters prefilled with organic solvent capable of extracting the lipid contents out of LDs. This approach is illustrated herein with LDs from diverse plant sources (*Gossypium hirsutum* and *Arabidopsis thaliana*). The inventors demonstrate the capability to directly sample populations of purified LDs as well as perform single-organelle mass spectrometry and lipid characterization. To illustrate the utility of this approach, the inventors show a compositional shift in TAG profiles in LDs purified from modified oleic cottonseed lines previously generated by the inventors (dominant-negative expression of Bnfad2 [89, 90], the presence of cyclic fatty acids in TAGs of cotton root LDs, and the molecular comparison between *Arabidopsis* seed and leaf LDs. These new approaches complement existing analytical and cell biology techniques and can be extended to the analysis of LDs and organelles from other organisms. This approach will help facilitate new studies about LD heterogeneity and the molecular nature of subcellular compartments in cellular systems.

Plant Growth Conditions: Cottonseeds were propagated under air-conditioned greenhouse conditions at 30° C. and supplemented with sodium vapor lamps to extend day length to 16 h. Opened bolls were harvested, and seeds were delinted in a table top, 10-saw laboratory gin. Seeds were from cultivar Coker 312 (nontransgenic) or were from transgenic lines (T5 generation) in the Coker 312 background, expressing a nonfunctional allele of the *Brassica napus* $\Delta$12-desaturase (Bnfad2) under the control of a seed-specific promoter [91, 92]. These seeds displayed reduced oil, elevated oleic acid phenotype relative to Coker 312 seeds [91, 92]. Intact embryos (mostly cotyledon tissues) were harvested from desiccated seeds following seed coat removal. Roots were collected on ice from germinated cottonseeds (cv. Coker 312) grown in the dark at 30° C. for 48-72 h. *Arabidopsis* wild type (Col 0) seeds were obtained from the *Arabidopsis* stock center at Ohio State University and propagated in house. Plants were grown in soil at 21° C. in a 16-h light/8-h dark cycle (between 45 and 65 mol/m2/s).

Imaging Lipid Droplets in Situ: LDs were imaged by confocal scanning fluorescence microscopy using BODIPY 493/503 to selectively visualize LDs in situ. All tissues were fixed in 4% w/v paraformaldehyde in 50 mM PIPES, pH 7.0, and stained with 1-10 µg/mL BODIPY 493/503. For BODIPY imaging, excitation of BODIPY was at 493 nm. Emission wavelength for BODIPY-stained LDs was 520 nm, exposed for 0.4-10 s with no gain. In leaves, chloroplast autofluorescence was acquired with an excitation of 493 nm and an emission wavelength at 692 nm exposed for 0.4 s. Images were acquired with a Zeiss 200 M optical microscope fitted with a CSU-10 Yokogawa confocal scanner (McBain Instruments) and captured with a digital camera (Hamamatsu, Phoenix, Ariz.). LD morphology and localization were characterized using the McMaster Biophotonics Facility and NIH ImageJ software (version 1.43T).

Lipid Droplet Purification: LDs from unfixed embryos of mature cottonseeds were isolated and purified in 100 mM Tris-HCl, 600 mM sucrose, 10 mM KCl, 1 mM EDTA, essentially as described by Chapman and Trelease [91] and based on methods developed by Huang [92]. Embryos were chopped into ~1-mm pieces with a razor blade in ice-cold buffer and purified through a sequential series of three floatations through 500 mM sucrose at 10,000×g (Sorvall SS-34 rotor or HB-6 rotor in a Sorvall RC 5C centrifuge or in a Centronix Microcentrifuge 1236V for smaller sample sizes). LDs were purified in a similar manner from cotton roots (at least 500 mg fresh weight) of 48-72-h-old seedlings, *Arabidopsis* leaves of 40-day-old plants (~8 g of fresh weight), or *Arabidopsis* seeds (10 mg). LDs from *Arabidopsis* leaves are few in number, and a final ultracentrifugation step (TLA-100 rotor at 100,000×g for 1 h, with a Beckman TL100 ultracentrifuge) helped to enrich these organelles in the top layer. For some studies, 50 mM PIPES-NaOH, pH 7.0, buffer was employed for homogenization and floatation. For all purifications, the fat pads were carefully collected with a spatula, and the LDs were suspended in buffer on ice. LDs were stained with 0.1-1 µg/mL of BODIPY 493/503 in 50 mM PIPES buffer.

Nanomanipulator Work Station: The Biometric L200 nanomanipulator work station developed by Zyvex (Richardson, Tex.) and the present inventors combined four nanopositioners (3102) with a piezo voltage source and a PM 2000B programmable four-channel pressure injector (3104) (Microdata Instruments, South Plainfield, N.J.) situated on an inverted microscope stage (3110) (TE2000U, Nikon, Melville, N.Y., diagrammed in FIG. 31A and FIG. 31B). The nanomanipulator has two modes of motion along the x, y, and z axes. The fine mode has 100 microns of travel in the x and z axis and 10 microns of travel in the y axis with 3.4 nm resolution controlled by piezoelectric crystals. The coarse mode has 12 mm of travel in the x axis and z axis and 28 mm of travel in the y axis with 100-nm resolution. The positioners consist of end effectors made up of six isolated, low impedance electrical connections and two glass capillary attachments. The end effectors are used for manipulation and, if needed, low impedance electrical characterization. Probes and capillaries (3106) attached to the positioners can be manually landed onto the sample and manipulated electronically using a joystick (3112) to control the position of the end effector. The capillaries (3106) are connected by Teflon tubing to a PM 2000B programmable four-channel pressure injector. LDs were visualized by epifluorescence, bright field, or differential scanning interference optics during collection (Nikon NIS elements), and the lipids (3108) were microextracted in 10 mM ammonium acetate in chloroform:methanol (1:1, v/v) in the capillary before MS. For single-lipid droplet analysis, the extraction solution was spiked with a Tri 15:0 TAG standard at a final concentration of 2 µM.

Nanospray Mass Spectrometry: A Proxeon nanospray source (Proxeon Biosystems, Odense, Denmark) was mounted on a Thermo LCQ Deca XP Plus quadrupole ion trap (Thermo Fisher Scientific). The lipids in the nanospray emitters (New Objective (Woburn, Mass.) Econo12 PicoTip™ Emitter platinum-coated or PROT12 break-to-open platinum emitters (tip opening diameters were 1±0.2 µm and 1-10 µm, respectively) were subjected to typical ion source conditions consisting of a potential of 0.8 to 1.5 kV, capillary temperature of 200° C., and capillary voltage of 3.0 V. Mass spectra were acquired using the LCQ Tune software program in the positive ion mode with three microscans and a continuous acquisition time. The mass spectra were analyzed with the XCalibur software package (version 2.0). Tandem mass spectrometry (MS/MS) analyses were used to confirm the identity of the triacylglycerols by a characteristic diacylglycerol fragment. Tandem spectra were acquired in positive ion mode with a typical isolation width of 3.0 m/z, normalized collision energy of 35%, activation Q of 0.250, and an activation time of 30 ms. Quantitative estimates of molecular compositions were calculated in Microsoft Excel with in house algorithms integrating peak areas, correcting for isotopic overlap, and when available normalizing to internal standards.

Conventional Lipid Extraction: Total lipids were extracted from LDs purified from mature embryos of desiccated seeds (cv. Coker 312, without and with a *Brassica* FAD2 nonfunctional allele) using the method of Bligh and Dyer [93]. Total lipid extracts were dissolved in 10 mM ammonium acetate in chloroform:methanol (1:1, v/v) and characterized by nanospray mass spectrometry or converted to fatty acid methyl esters and analyzed by gas chromatography equipped with a flame ionization detector. [91]

Fatty Acid Methyl Ester Preparation and Analysis: Additional total lipid extracts of the purified LD fractions were converted into fatty acid methyl esters. Fatty acid methyl esters were prepared by transesterification with 1 N methanolic HCl at 85° C. for 2 h. A heptadecanoic acid (C17:0) standard was added to aid quantification. Fatty acid methyl esters were separated on a 30 m×0.25 mm inner diameter Supelcowax 10 fused silica capillary column on a HP 5890 Series II Plus gas chromatograph with an initial oven temperature of 200° C. increasing at a rate of 1.3° C./min to a final temperature of 230° C.

Electrospray Mass Spectrometry: Because the ion trap is limited in its ability to carry out precursor-product scans, additional acyl chain information was derived from analysis of total lipid extracts of LD fractions purified from cotton (seed, root) and *Arabidopsis* tissues (seed, leaf) using a Waters Micromass Quattro Ultima triple quadrupole mass spectrometer (Waters, Milford, Mass.). Typical scanning conditions for a direct infusion rate of 10-20 µl/min were carried out in positive ion mode with a 3-3.5 kV spray voltage, 40 V cone voltage, and a scan range of 750 to 1000 m/z. The desolvation and source temperatures were maintained at 200 and 80° C., respectively, and the desolvation and cone gas flows were set at 300 and 80 liters/hr, respectively. Tandem scans (MS/MS), whether detecting the precursor ions that lost a particular acyl chain in neutral loss mode or single precursor-product species, were performed with collision energy of 30 V with a scan range from 400 to 1000 m/z.

Figure 31A:
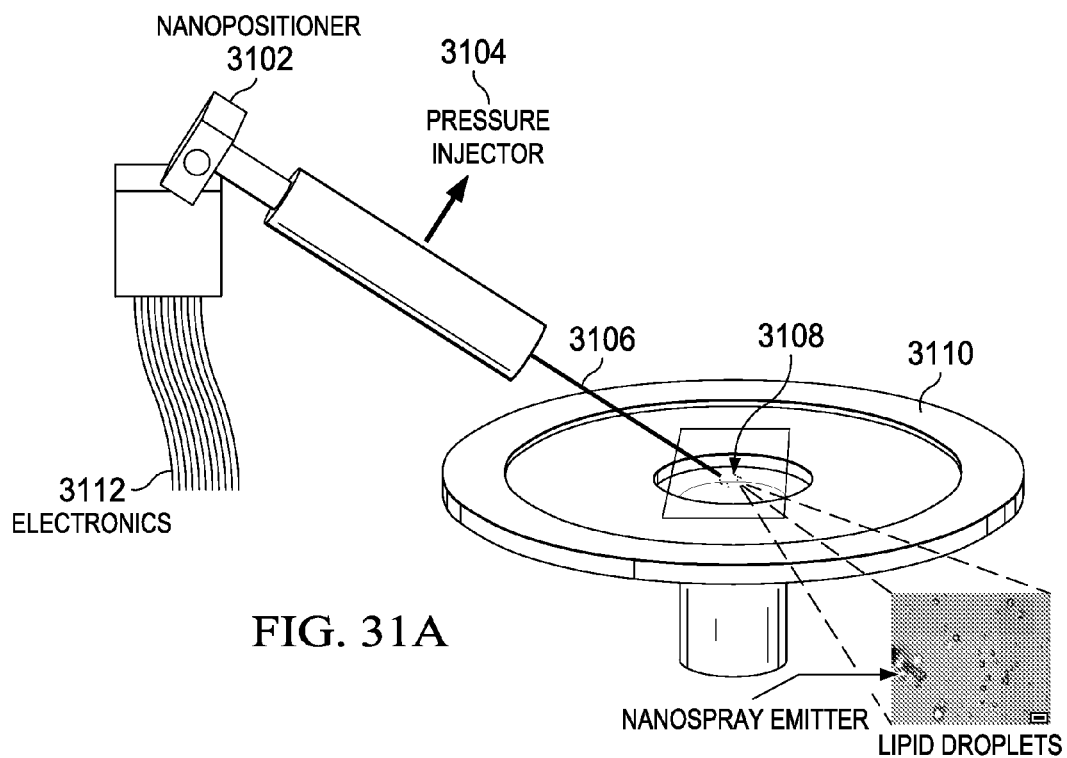
FIGS. 31A and 31B show a schematic of direct organelle mass spectrometry. A schematic representation of DOMS using the L200 nanomanipulator coupled to nanospray mass spectrometry.
Figure 31B:
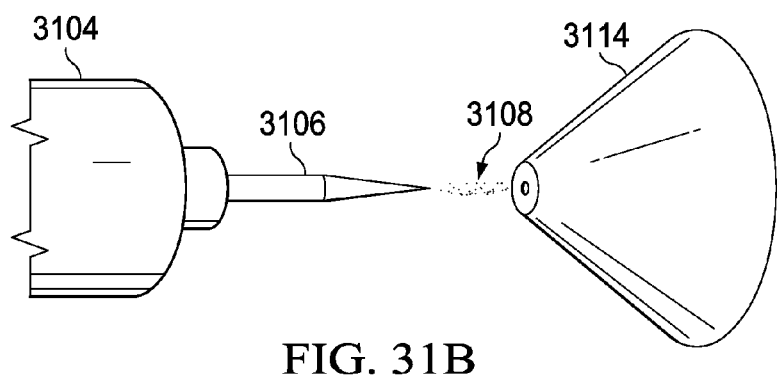

Direct Organelle Mass Spectrometry: Interfacing direct organelle sampling with nanospray mass spectrometry required the incorporation of nanospray emitters that could control the liquid flux at the tip opening in contact with the sample of interest while also sufficiently concentrating the extracted lipids to detect their composition with high resolution. The development of a nanomanipulator apparatus (FIG. 31) [87] coordinated the positioning of up to four emitters in a three-dimensional plane situated on the stage of an inverted light microscope for maximum working distance. Emitters, prefilled with an organic microextraction solution that served the dual purpose of extracting the lipids from the droplets and facilitating the formation of nanospray droplets, were positioned adjacent to purified LDs (FIG. 31A). Direct interfacing of the emitter with a dynamic pressure injector provided the sensitivity necessary to fill nanoliter volumes (usually between 5-30 psi of fill pressure) and selectively capture individual organelles. After sampling LDs, the emitters were remounted onto the nanospray apparatus (FIG. 31B) for chemical analysis.

Figure 32A:
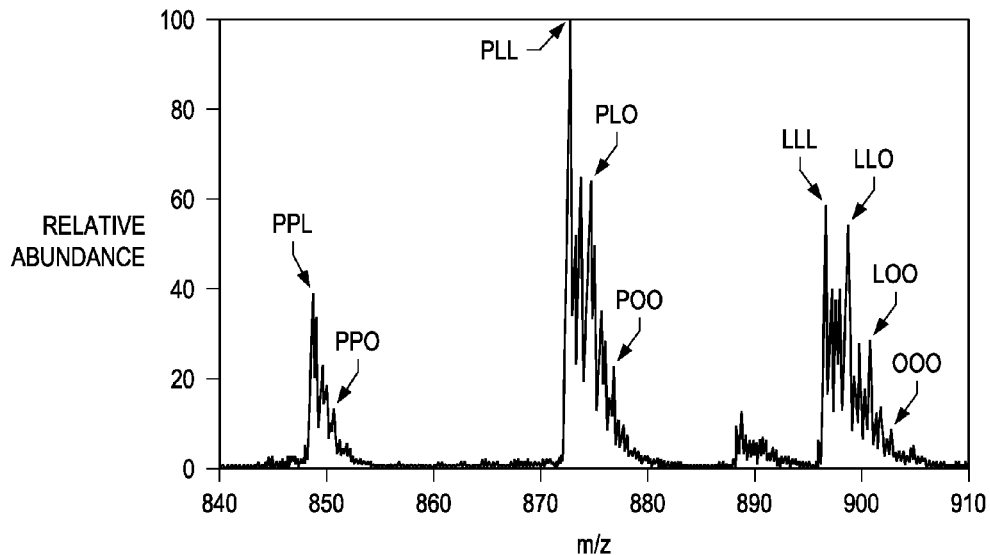
FIGS. 32A-32C shows the TAG profiles of purified cottonseed lipid droplets analyzed by DOMS.
Figure 32B:
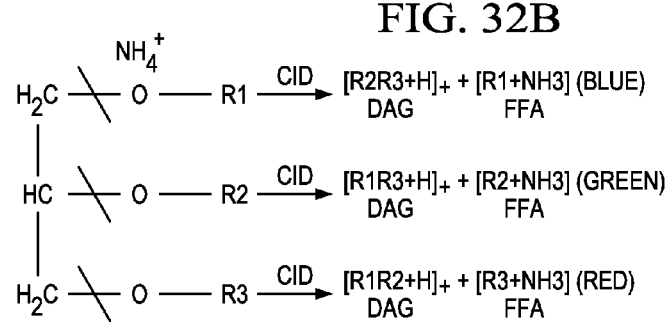
Figure 32C:
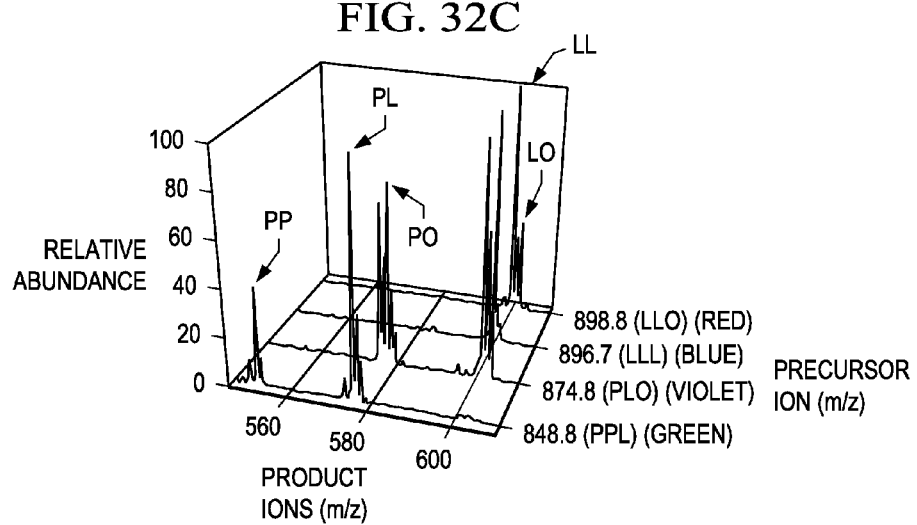

Lipid Droplet Characterization: To test the DOMS approach, LDs were purified from mature cotton embryos (cv. Coker 312) due to their abundance within seed tissues, relative ease of purification and the known composition of TAGs in standard cottonseed oil [33]. These LDs, suspended in ~100 µL, were somewhat variable in size (~0.5-2.0 µm diameter) (FIG. 31A) but retained similar spherical morphology to that observed in situ. A random sampling of approximately two dozen LDs produced a high resolution spectrum of TAGs (FIG. 32A). The TAG molecular species under these conditions were of sufficient concentration to analyze by MS/MS and confirm/assign acyl composition (FIGS. 32B and 32C). Tandem MS of TAG precursor ions produce diacylglycerol product ions that lead to a high confidence of acyl chain identification [94]. The TAG acyl chain distribution in purified cottonseed LDs primarily consisted of linoleic (18:2), oleic (18:1), and palmitic acids (16:0).

Figure 33A:
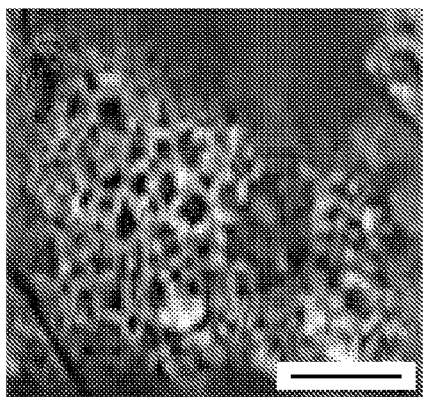
FIGS. 33A-33G show the characterization of lipid droplets from high oleic cottonseed mutants. Representative in situ confocal images of mature cotton embryos from wild type (cv. Coker 312) (FIG. 33A) and a transgenic line expressing a Brassica nonfunctional allele of a delta-12 fatty acid desaturase (Bnfad2) stained with BODIPY 493/503, (FIG. 33B). Purified LDs of Coker 312 (FIGS. 33C and 33E) and Bnfad2 (FIGS. 33D and 33F) mature embryos visualized in bright field and stained with BODIPY 493/503.
Figure 33B:
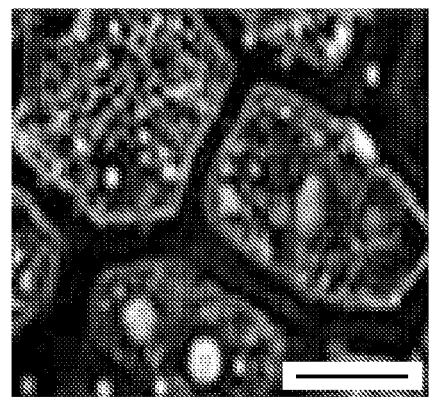
Figure 33C:
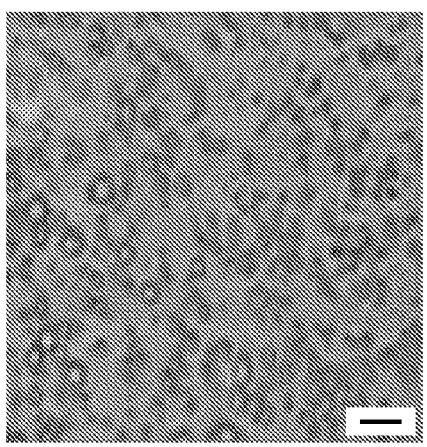
Figure 33D:
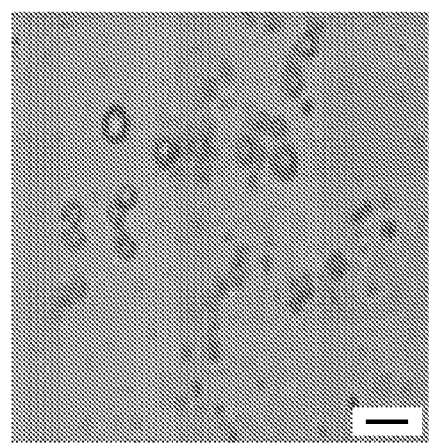
Figure 33E:
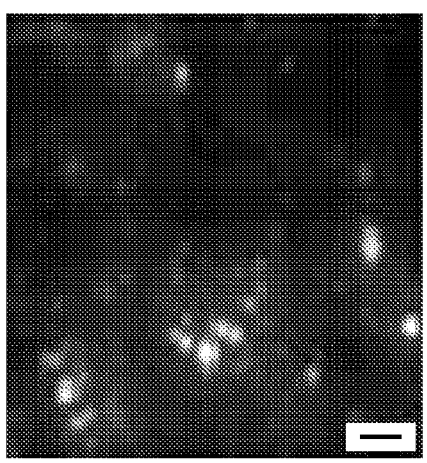
Figure 33F:
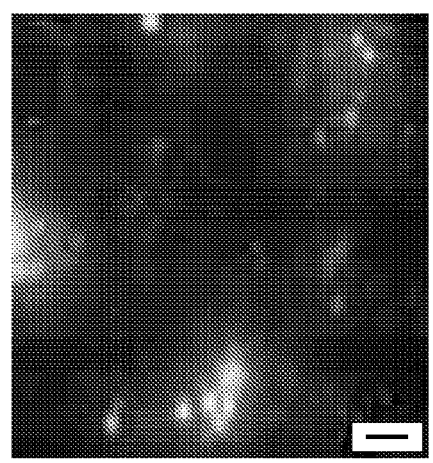
Figure 33G:
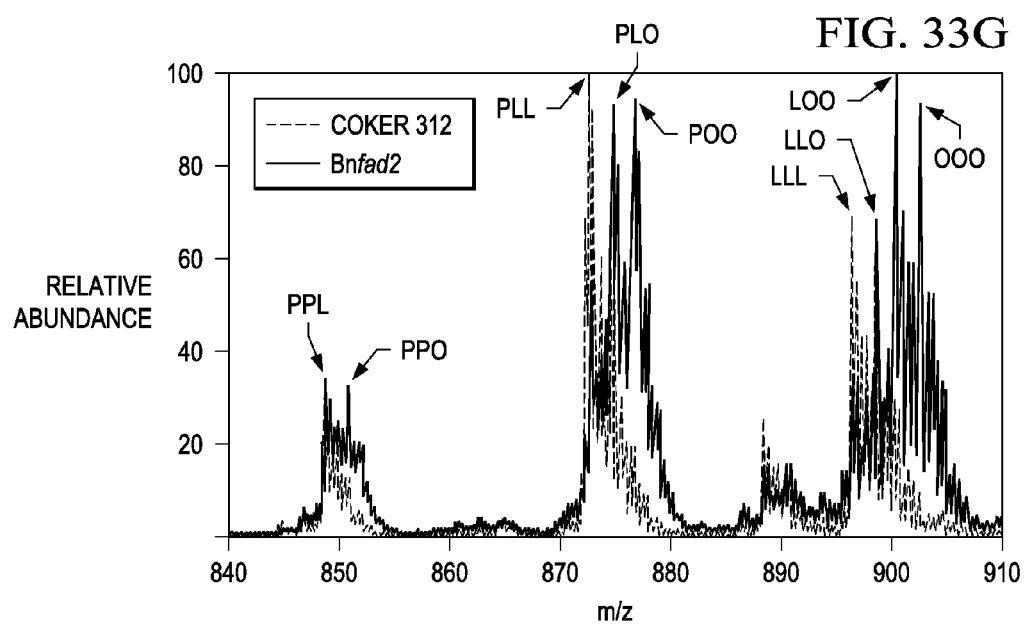
Figure 34A:
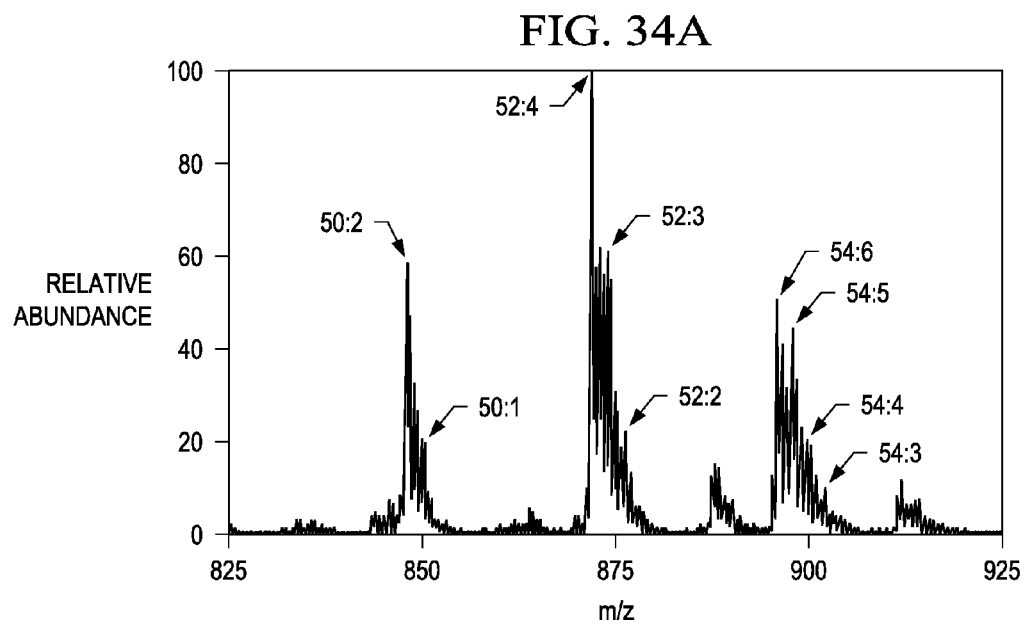
FIGS. 34A-34D show the validation of DOMS with conventional total lipid extracts. Representative TAG profiles from total lipid extracts of purified LDs from mature cotton embryos of Coker 312 wild type (FIG. 34A) and Bnfad2 transgenic (FIG. 34B) lines. Dominant TAG species are identified as ammonium adducts $[M+NH4]^+$ with peaks labeled according to the total number of carbons followed by the total number of double bonds for that particular TAG mass-to-charge ratio. Quantitative comparison of molecular TAG content (FIG. 34C, Coker 312.
Figure 34B:
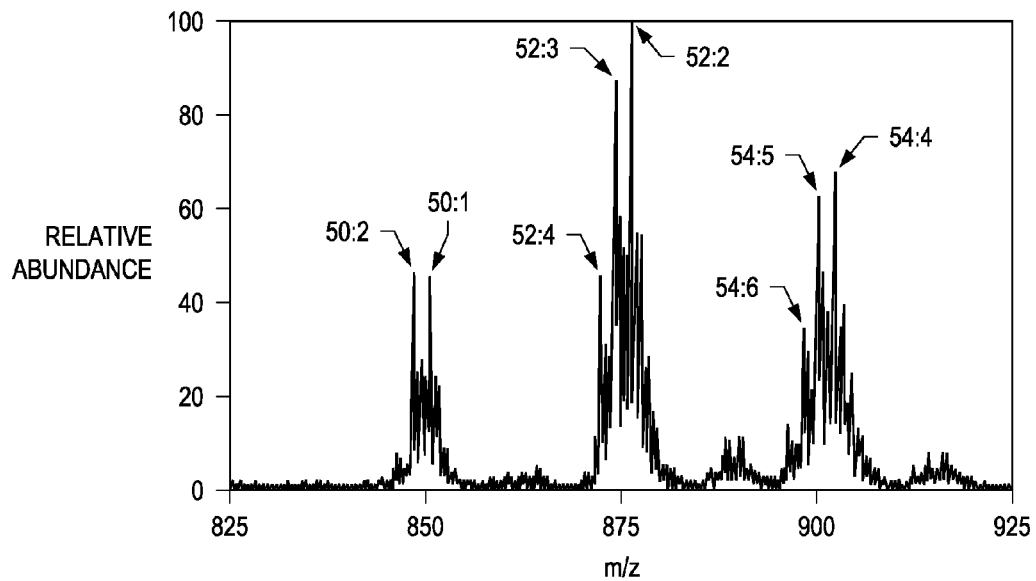

Most LDs share a similar spherical morphology despite some significant alterations in the composition of their neutral lipid core or surrounding phospholipid/protein-lined monolayer [69, 73, 90]. However, the size of LDs is much more variable depending on tissue type [62] and/or metabolic state [73, 90]. Expression of a *Brassica* nonfunctional allele of a δ-12 fatty acid desaturase (Bnfad2) in a Coker 312 wild type background produces fewer and larger LDs in cotyledons (FIGS. 33A and 33B) [90]. Purification of these LDs was verified by bright field (FIGS. 33C and 33D) and epifluorescence microscopy (stained with a neutral lipid specific fluorescent dye, BODIPY 493/503) (FIGS. 33E and 33F). Direct sampling of these Bnfad2 LDs showed a distinct shift toward increased oleic acid (18:1) acyl chain distribution within TAG at the expense of linoleic acid (18:2) (FIG. 33G) that was confirmed qualitatively and quantitatively with conventional chemical extractions of total seed lipids (FIGS. 34A and 34B) and analysis of total fatty acid content by gas chromatography equipped with a flame ionization detector, consistent with suppression of endogenous oleic acid desaturation by FAD2 (dominant-negative mutation). Hence, with this approach, it was possible to demonstrate directly a change in molecular composition at the organelle level in these metabolic mutants.

Figure 34C:
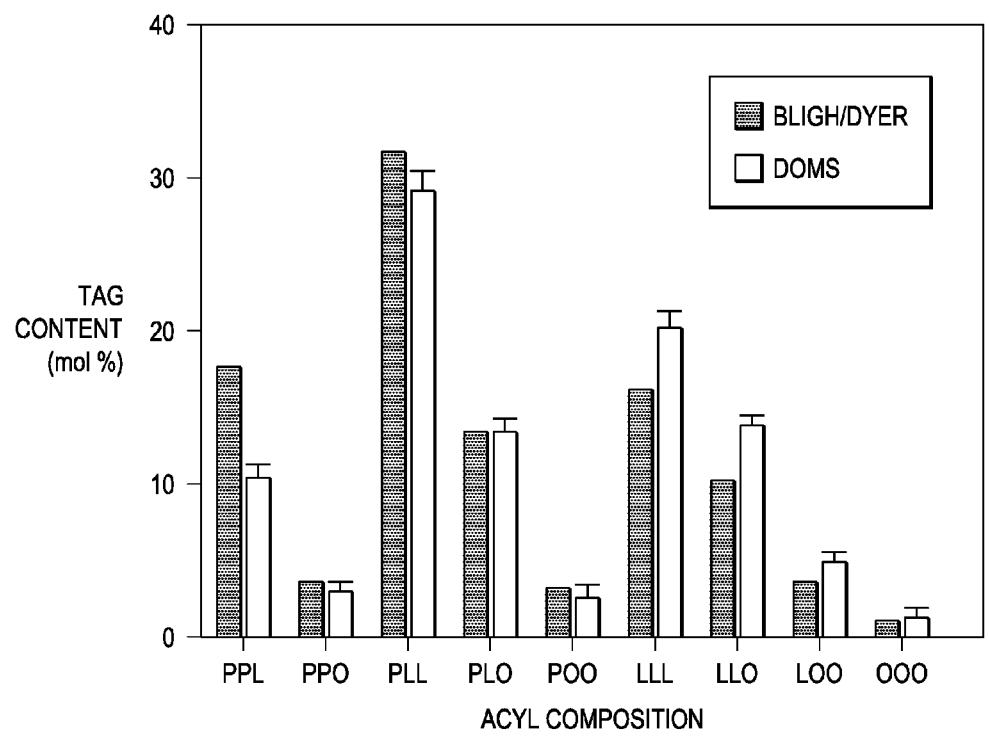
Figure 34D:
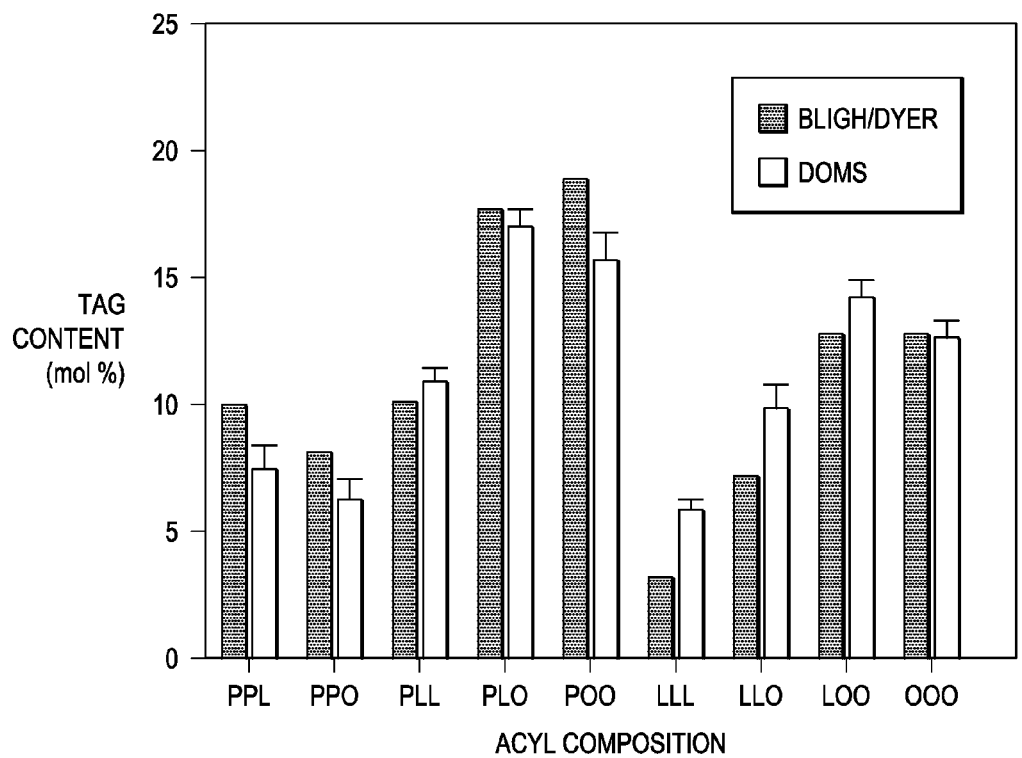

Sampling multiple LDs resulted in sufficient TAG concentrations within the nanospray emitters to allow for detailed compositional information to be acquired through tandem MS. The overall variability in TAG composition from sampling small, random populations of cottonseed LDs (10-25 droplets per sample) was relatively low (FIGS. 34C and 34D). Direct visualization and sampling of a single Bnfad2 LD (FIG. 34B) required fine tuning the filling conditions to prevent multiple LDs from entering the tip and obscuring the final suspension of LD.

Figure 35A:
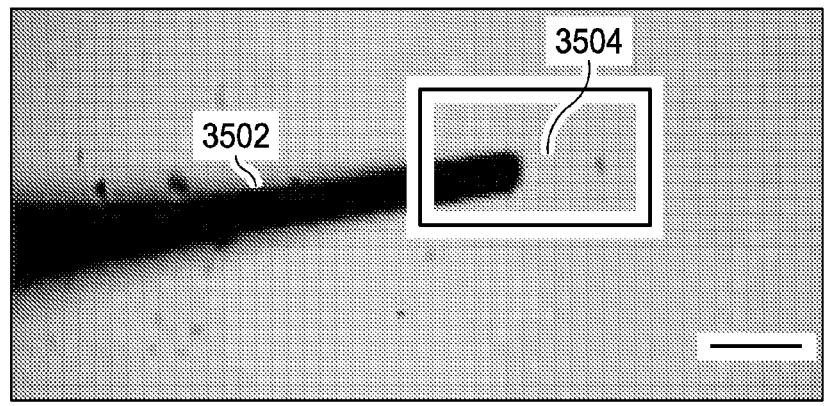
FIGS. 35A-35C show single lipid droplet mass spectrometry and lipid droplet heterogeneity.
Figure 35B:
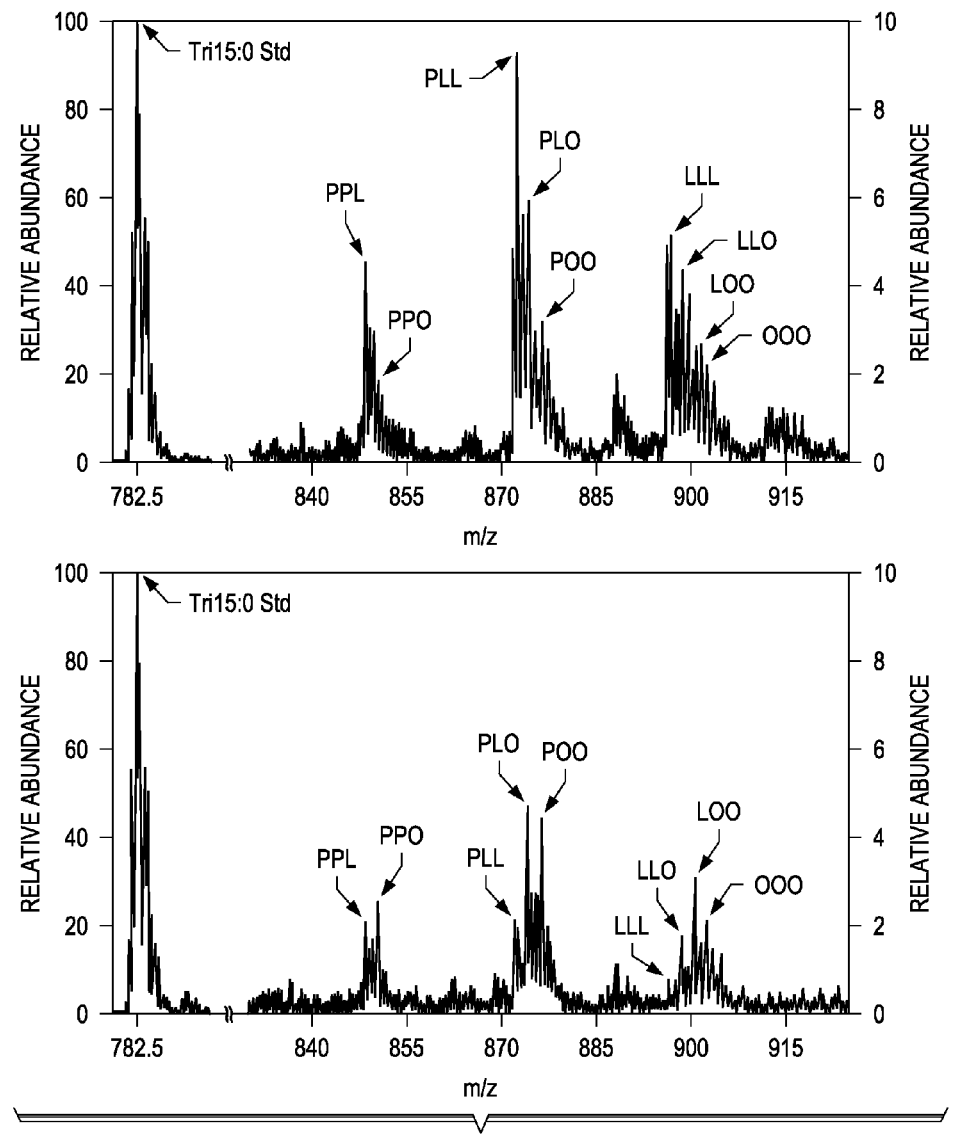
Figure 35C:
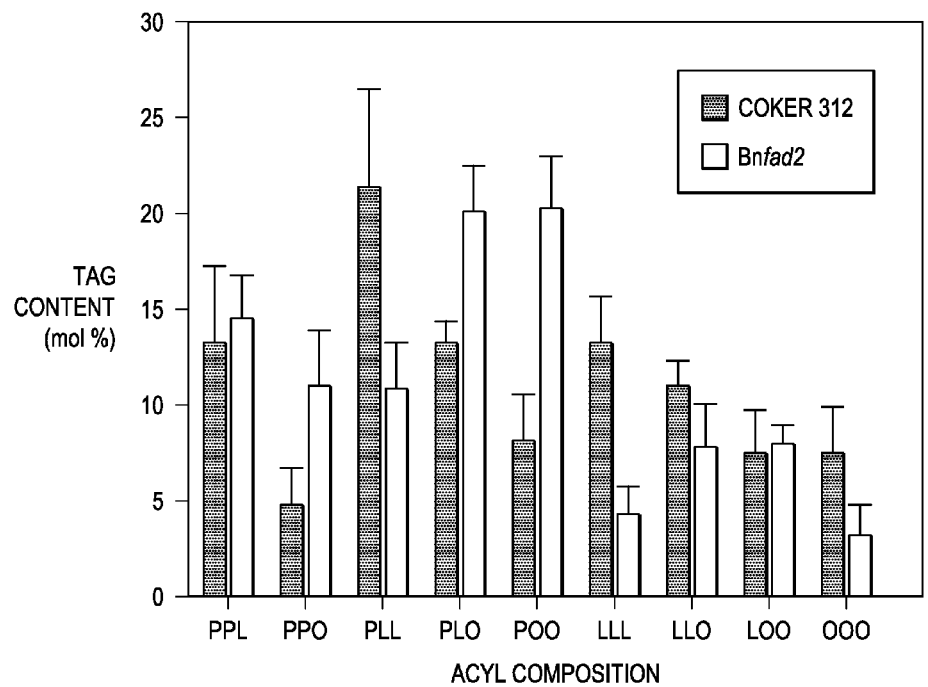

To assess the heterogeneity of individual LDs isolated from cottonseed embryos, LDs were sampled individually for both the Coker 312 and Bnfad2 (Tables 2 and 3 and FIGS. 35A-35C). Representative TAG spectra from single Coker 312 (FIG. 35B, top) and single Bnfad2 (FIG. 35B, bottom) LD showed identifiable TAG profiles of single LD. There was a substantial difference in mol % of TAG species (normalized to Tri 15:0 internal standard) among individual LD, both within the Coker 312 seeds and the Bnfad2 seeds (Tables 2 and 3). The average TAG molecular composition (FIG. 35C; Tables 2 and 3) of seven individual LDs combined were distinctly different from one another (Coker 312 versus Bnfad2), and the average composition of each variety approached that of the composition varieties when multiple LDs were sampled together. However, there was considerable heterogeneity among purified seed lipid droplets, suggesting a complexity in the biogenesis of LD not able to be appreciated until now. In other words, the overall average lipid composition of these seeds comes from discrete LD packages with variable TAG profiles. This is new information about LDs that would not be possible were an individual droplet not able to be sampled directly by MS. These results indicate that this technique of DOMS can be used to assess organelle heterogeneity by sampling single organelles.

Figure 36A:
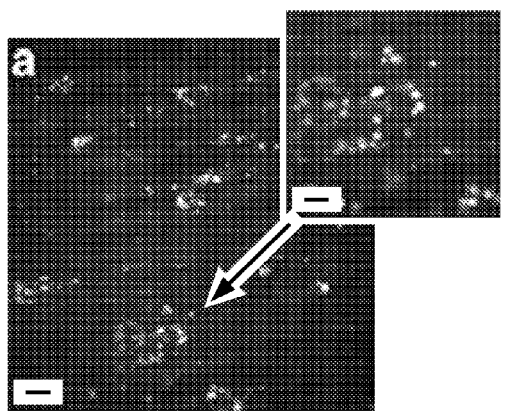
FIGS. 36A-36C show the detection of lipid droplets with cyclic fatty acyl chains in cotton roots.
Figure 36B:
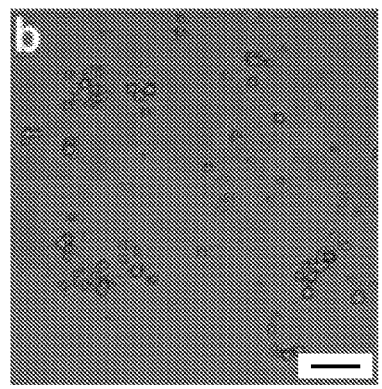
Figure 36C:
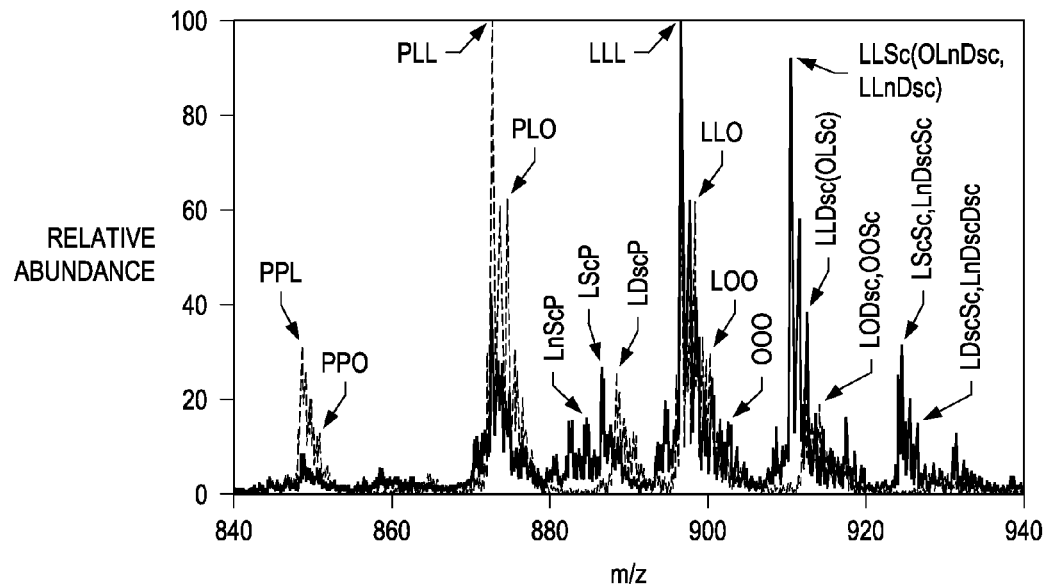
Figure 37A:
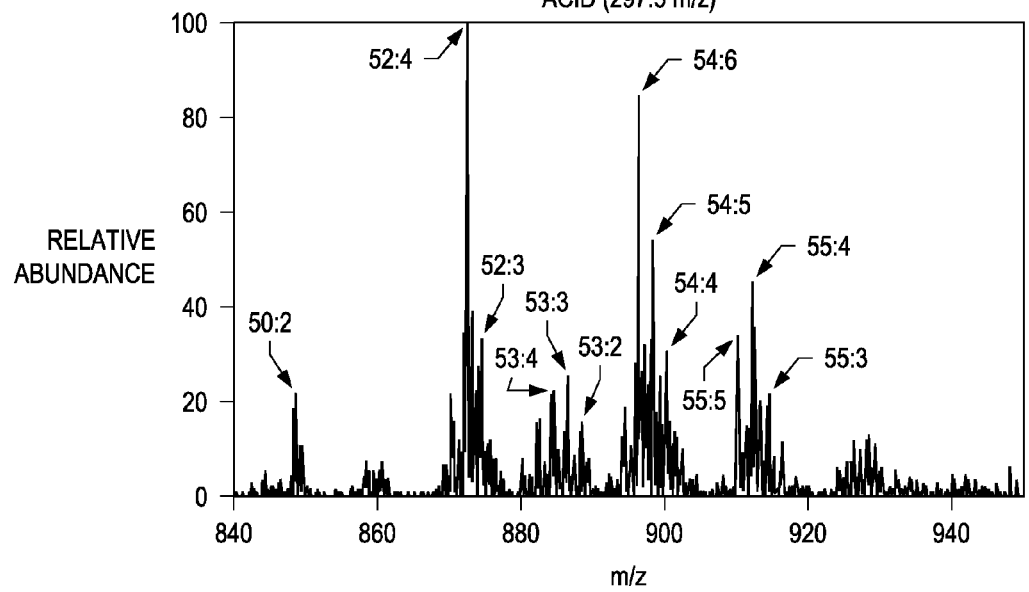
FIGS. 37A-37C show tandem MS analysis of lipid extracts of purified cotton root lipid droplets. In addition to tandem MS of LDs sampled through DOMS, precursor-product scans of lipid extracts of purified LDs of cotton roots aided in identification of cyclic fatty acids. Shown are precursors TAG profiles of malvalic/linoleic.
Figure 37B:
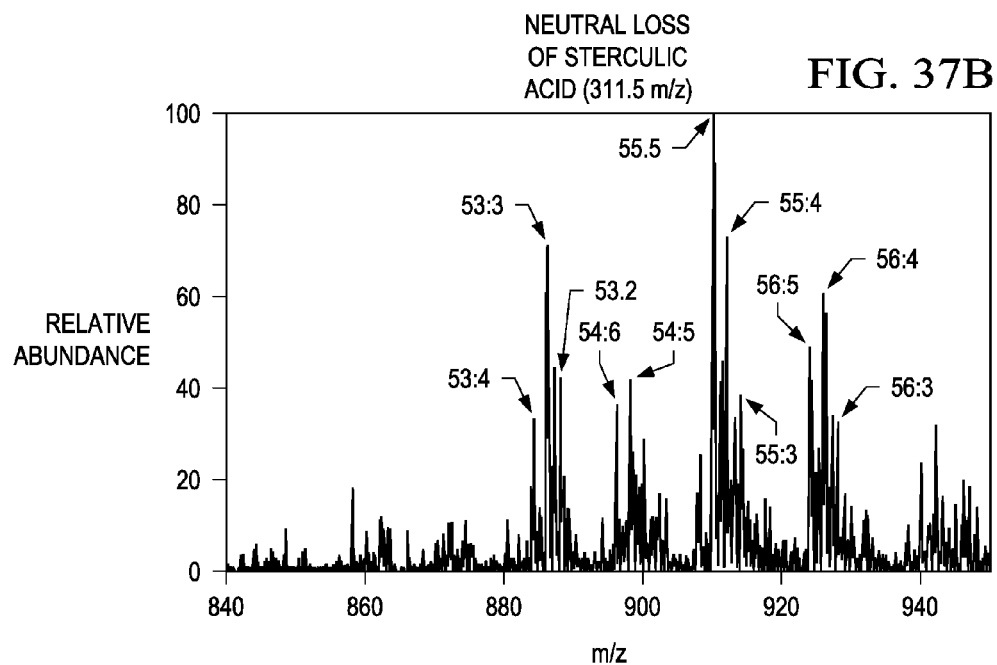
Figure 37C:
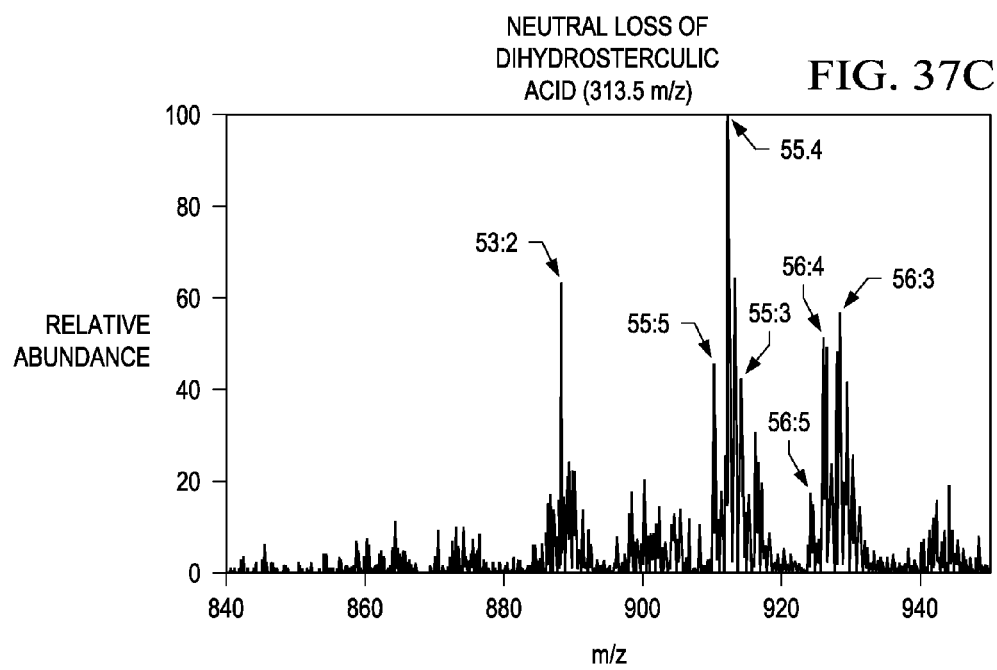

One advantage of this DOMS approach would be to distinguish by molecular composition between LDs of similar morphology. Cyclic fatty acids accumulate in root tissues of cotton seedlings during the early growth stages and include malvalic acid (8,9-methylene-8Z-heptadecenoic acid, 32.6% of total fatty acid), sterculic acid (9,10-methylene-9-octadecenoic acid, 11.0%), and dihydrosterculic acid (9S,10R-methyleneoctadecanoic acid, 0.6%) (83, 35). These cyclic fatty acids are enriched in the TAG fractions and presumed to be packaged into LDs in root cells. LDs in root cells (visualized by BODIPY-specific fluorescent staining) appeared to be either localized in clusters around the nucleus or dispersed throughout the cytosol in different root cells (FIG. 36A). Isolation and purification of these LDs did not affect their size and morphology (FIG. 36B), and this morphology was similar to the LDs purified from cotyledons of seed tissues (FIG. 33C). TAG profiles in root LDs were distinct from those derived from cotyledon tissues of seeds (FIG. 36C), and indeed, these root TAG were enriched in cyclic fatty acids with sterculic and dihydrosterulic acids on one or two acyl chains (confirmed by tandem MS, FIGS. 37 B and C). Although malvalic acid is known to be prevalent in roots by gas chromatographic studies [95], here by MS, it was not distinguishable from linoleic acid (FIG. 37A) in the purified droplets (both fatty acids have a molecular mass of 280.45 g/mol). Nonetheless, it was possible to directly distinguish LDs of differing molecular composition that were otherwise indistinguishable by morphology, illustrating that DOMS might be used to assess organelle heterogeneity within a given tissue or cell type.

TABLE 2

Heterogeneity of TAG molecular species in Coker 312-purified seed lipid droplets P, 16:0-palmitic acid; O, 18:1 oleic acid; L, 18:2-linoleic acid.

| | TAG molecular composition | | | | | | | | |
|---|---|---|---|---|---|---|---|---|---|
| | PPL[a] | PPO | PLL | PLO | POO | LLL | LLO | LOO | OOO |
| | | | | mol % | | | | | |
| LD1 | 15.9 | 4.5 | 19.8 | 14.8 | 9.8 | 11.0 | 10.9 | 6.1 | 7.1 |
| LD2 | 9.1 | 5.7 | 18.5 | 11.5 | 10.4 | 15.2 | 13.0 | 10.4 | 6.3 |
| LD3 | 14.7 | 9.1 | 16.0 | 12.4 | 9.0 | 9.8 | 10.9 | 8.4 | 9.6 |
| LD4 | 17.2 | 4.3 | 27.9 | 14.2 | 4.9 | 13.1 | 9.7 | 5.4 | 3.2 |
| LD5 | 16.7 | 3.8 | 26.0 | 14.1 | 6.3 | 12.3 | 10.1 | 6.0 | 4.7 |
| LD6 | 13.0 | 2.6 | 26.9 | 13.4 | 6.5 | 16.3 | 10.5 | 6.1 | 4.6 |
| LD7 | 7.2 | 4.2 | 16.6 | 13.2 | 9.1 | 16.6 | 13.7 | 11.4 | 8.0 |
| Mean | 13.4 | 4.9 | 21.7 | 13.4 | 8.0 | 13.5 | 11.3 | 7.7 | 6.2 |
| S.D. | 3.9 | 2.1 | 5.1 | 1.2 | 2.1 | 2.6 | 1.5 | 2.4 | 2.2 |

[a]TAG acyl chains are sn-nonspecific.

TABLE 3

Heterogeneity of TAG molecular species in Bnfad2-purified seed lipid droplets P, 16:0-palmitic acid; O, 18:1 oleic acid; L, 18:2-linoleic acid.

| | TAG molecular composition | | | | | | | | |
|---|---|---|---|---|---|---|---|---|---|
| | PPL[a] | PPO | PLL | PLO | POO | LLL | LLO | LOO | OOO |
| | | | | mol % | | | | | |
| LD1 | 17.9 | 14.0 | 7.0 | 16.2 | 22.7 | 1.6 | 4.0 | 8.8 | 7.7 |
| LD2 | 13.0 | 8.3 | 13.2 | 22.3 | 15.4 | 6.5 | 10.3 | 7.9 | 3.1 |
| LD3 | 13.2 | 9.4 | 11.4 | 21.4 | 20.4 | 5.0 | 8.5 | 6.9 | 3.8 |
| LD4 | 14.9 | 11.6 | 9.2 | 19.8 | 22.8 | 3.7 | 5.5 | 6.5 | 6.0 |
| LD5 | 13.6 | 7.5 | 14.1 | 20.4 | 18.5 | 5.1 | 10.7 | 8.3 | 1.7 |
| LD6 | 11.8 | 10.5 | 10.8 | 22.8 | 20.3 | 4.1 | 7.8 | 9.0 | 3.0 |
| LD7 | 16.0 | 15.0 | 10.6 | 17.1 | 20.7 | 4.5 | 7.8 | 7.7 | 0.7 |
| Mean | 14.3 | 10.9 | 10.9 | 20.0 | 20.1 | 4.4 | 7.8 | 7.9 | 3.7 |
| S.D. | 2.1 | 2.8 | 2.4 | 2.5 | 2.5 | 1.5 | 2.4 | 0.9 | 2.4 |

[a]TAG acyl chains are sn-nonspecific.

Figure 38A:
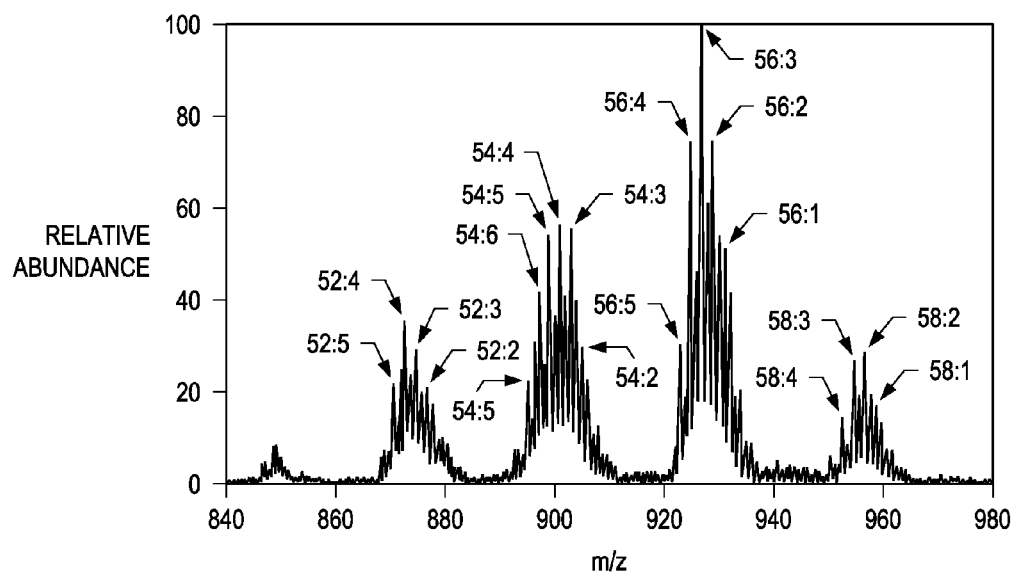
FIGS. 38A-38F show the characterization of Arabidopsis leaf and seed lipid droplets. Representative TAG profiles of LDs purified from (FIG. 38A) Arabidopsis mature seeds and (FIG. 38B) rosette leaves of 40-day-old plants. Labels show the total number of carbons followed by the total number of double bonds for that particular TAG mass-to-charge ratio. Seed LDs showed an abundance of 20:1/eicosenoic fatty acids, whereas leaf LDs showed typical 18:3/16:3 fatty acids. Representative in situ confocal image, (FIG. 38C) of wild type Arabidopsis mesophyll tissue stained with BODIPY 493/503 (red autofluorescence represents chloroplasts) and bright field snapshot image, (FIG. 38E) of purified Arabidopsis leaf LDs. Representative in situ confocal image (FIG. 38D) of wild type Arabidopsis seed LDs and (FIG. 38F) epifluorescence image of purified Arabidopsis seed LDs stained with BODIPY 493/503. Scale bars represent 20 µm ((FIG. 38C), 10 µm ((FIG. 38C, inset), and 5 µm ((FIGS. 38D-38F).
Figure 38B:
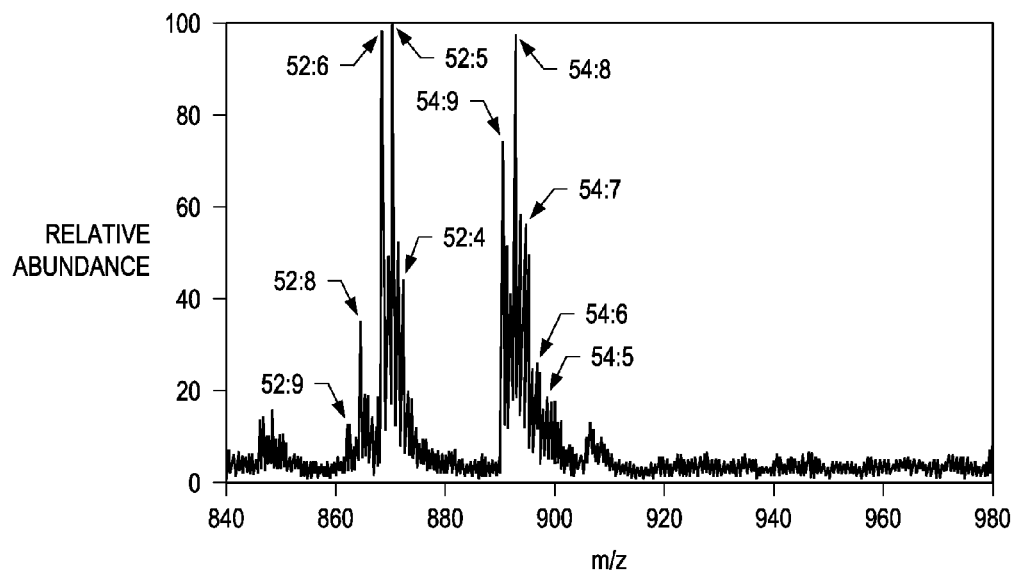
Figure 38C:
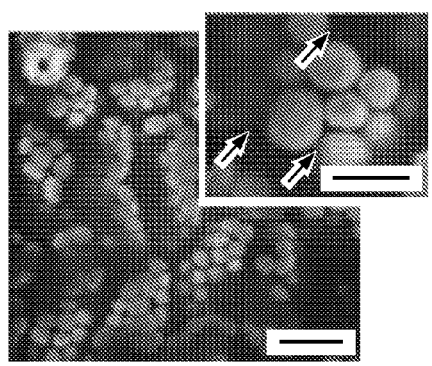
Figure 38D:
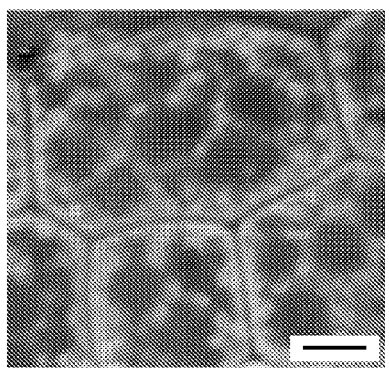
Figure 38E:
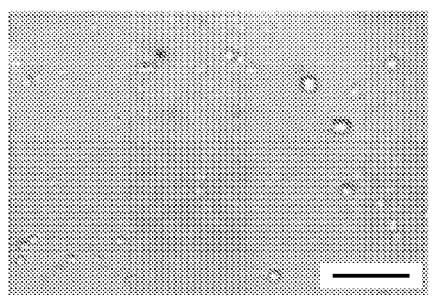
Figure 38F:
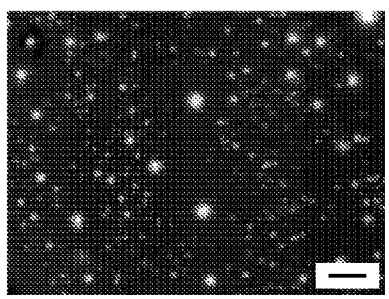

A single *A. thaliana* seed (~15-25 µg) provides more than enough LDs for direct organelle mass spectrometry (FIG. 38A), and these seed LDs can be purified by a rapid two-step procedure (FIG. 38F) reducing the time from LD purification to determination of LD TAG composition to less than an hour. On the other hand, the rosette leaves (~1 mg of dry weight) of 40-day-old *Arabidopsis* plants contain very few LDs per cell (FIGS. 38 C and E), and much more tissue was required for purification of LDs from leaves. DOMS showed that the seed LDs contained characteristic 20:1/eicosenoic fatty acids in their TAGs, whereas the LDs from leaves instead contained more 16:3 and 18:3 fatty acids that are most characteristic of leaf acyl lipids (FIG. 38B) [96]. LDs in leaves (FIG. 38C), although similar in morphology to those in seeds (FIG. 38D), likely have a function different from the long term storage function of TAGs in seeds for germination and seedling establishment. Profiling organelles by DOMS from different tissues and metabolic contexts will provide new insights into how cellular and subcellular heterogeneity contributes to cellular function, which have been questions difficult to address directly until now.

The development of the L200 nanomanipulator supports a variety of potential analytical techniques at the cellular and subcellular level. Here, we illustrate some of these capabilities by the direct visualization of LDs derived from various cell types coupled with detailed chemical analysis. Conventional lipid profiling by MS, although detailed and capable of resolving highly complex compositions of molecules at a range of endogenous concentrations, relies on total extractions of lipid molecules from organs, tissues, or cell types, resulting in a rich mixture of compounds that lose all spatial context. Here, the DOMS facilitates a complete, comprehensive lipidomics profiling while maintaining organellar identity of the sample source. Although seed LDs contain mostly TAG molecules, there are also a small proportion of phospholipids and proteins (e.g. ~97% TAG, 1% phospholipid, 2% protein in a 1-μm diameter LD) [69]. Although only TAG molecules were detected with DOMS, it is likely that ion suppression effects prevented the detection of phospholipid with the ion trap MS. It is possible through instrument modifications that interfacing DOMS with a triple quadrupole MS might facilitate the detection of phospholipid and/or proteins.

The technique presented hereinabove is versatile and could be combined for the lipid profiling of other subcellular components and combined with microscopic analysis serve as a means of evaluating detailed molecular changes at the organellar level to address arrange of biological questions intractable until now. For example, considering the low variability of sampling multiple LDs, it was surprising to uncover significant TAG compositional heterogeneity when sampling individual LDs, pointing to complexity at the subcellular level in packaging TAG into lipid droplets, that until now had not been considered in models of LD biogenesis. Furthermore, it is possible to envision this approach expanded to support broad-based MS analysis of other macromolecules in organellar samples, such as proteomic or general metabolomic studies, placing this DOMS approach at the forefront of biochemical analysis with microscale resolution. Although the positioning resolution of the L200 surpasses many commercially available nanomanipulators, the relative ease of combination of a standard robotic-controlled microscope stage with conventional light microscopy and standard MS instruments (nanospray source mounted on an ion-trap or triple quad MS) provides a high level of flexibility to achieve diverse and specialized systems [87, 88]. In this case, only a single end effector holding a glass nanospray emitter was necessary for sampling purified LDs; however, there are multiple ports on the L200 that could be used as molecular "tweezers" and low impedance electrical positioners [87] that might be advantageous for handling and/or sampling cellular constituents on stage, either from purified populations as was shown here, or perhaps even in situ by microdissection of whole tissue samples. Currently the nanospray emitters are not designed to penetrate the thick cell walls of plant tissues and permit selection of organelles in situ. In the future, it might be possible to use some combination of laser microdissection or cell wall digestion to gain access to organelles within tissue samples, and advances in sample preparation will expand the uses of DOMS.

Recent advances in imaging MS (MALDI-MS [84], DESI-MS [86], SIMS [79, 85], and Raman spectroscopy [79] have acquired compositional information in association with spatial distribution in biological specimens. Unfortunately, the limited resolution of MALDI-MS (typical lateral resolution of 25-100 μm [84]) and DESI-MS (typically only 250 μm [86]) makes it impossible to resolve the compositional information of single organelles. Although Raman spectroscopy approaches afford some chemical compositional information at high spatial resolution in situ, this information is limited to gross chemical information, such as confirming neutral lipid classes or overall saturation of acyl chains. A significant advantage of imaging MS is acquiring chemical information in situ. However, significant tissue preparation is often required that can adversely affect quantitative accuracy and compositional distribution [84]. For example, the quantitative accuracy of MALDI-MS and TOF-SIMS is significantly affected by sample preparation necessary to withstand vacuum pressure and ion generation energies [86]. The DOMS method of the present invention can derive information at a single organelle (LD) level with more comprehensive chemical compositional information than is possible by any current MS imaging approach that relies on direct ionization properties of molecules from a surface. Indeed the DOMS approach might be modified to be combined or to verify various in situ imaging techniques and together help to generate more complete chemical maps of cells and subcellular compartments than is currently available. The DOMS approach developed and described herein has the potential to be applied to diverse areas of cell biology and address many questions. In specific applications toward LDs, progress has been made in understanding the mechanisms of lipid production, packaging into cytosolic LDs, and physiological roles of LDs.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application Publication No. 2009/0261244: Microengineered Nanospray Electrode System.
U.S. Pat. No. 7,385,189: Nanospray Ionization Device and Method.
U.S. Pat. No. 6,812,460: Nano-Manipulation by Gyration.
1. Cooks R G, Ouyang Z, Takats Z, Wiseman J M. Ambient Mass Spectrometry. Science 2006; 311(5767):1566-70.
2. Van Berkel G J, Sanchez A D, Quirke J M E. Thin-Layer Chromatography and Electrospray Mass Spectrometry Coupled using A Surface Sampling Probe. Anal Chem 2002; 74(24):6216-23.
3. Na N, Zhao M, Zhang S, Yang C, Zhang X. Development of A Dielectric Barrier Discharge Ion Source for Ambient Mass Spectrometry. J Am Soc Mass Spectrom 2007; 18(10): 1859-62.
4. Wiseman J M, Laughlin B C. Desorption Electrospray Ionization (DESI) Mass Spectrometry: A Brief Introduction and Overview. Curr September 2007; 22(1):11-4.
5. Takats Z, Cotte-Rodriguez I, Talaty N, Chen H, Cooks R G. Direct, Trace Level Detection of Explosives on Ambient Surfaces by Desorption Electrospray Ionization Mass Spectrometry. Chem Commun (Camb) 2005; (15): 1950-2.
6. Justes D R, Talaty N, Cotte-Rodriguez I, Cooks R G. Detection of Explosives on Skin using Ambient Ionization Mass Spectrometry. Chem. Commun (Camb) 2007; (21): 2142-4.
7. Asano K G, Ford M J, Tomkins B A, Van Berkel G J. Self-Aspirating Atmospheric Pressure Chemical Ionization Source for Direct Sampling of Analytes on Surfaces and in Liquid Solutions. Rapid Commun Mass Spectrom 2005; 19(16):2305-12.
8. Van Berkel G J, Kertesz V, Koeplinger K A, Vavrek M, Kong A-NT. Liquid Microjunction Surface Sampling Probe Electrospray Mass Spectrometry for Detection of Drugs and Metabolites in Thin Tissue Sections. J Mass Spectrom 2008; 43(4):500-8.
9. Yamamura S, Kishi H, Tokimitsu Y, Kondo S, Honda R, Rao S R, et al. Single-Cell Microarray for Analyzing Cellular Response. Anal Chem 2005; 77(24):8050-6.
10. Ishoy T, Kvist T, Westermann P, Ahring B. An Improved Method for Single Cell Isolation of Prokaryotes from Meso-, Thermo- and Hyperthermophilic Environments using Micromanipulation. Appl Microbiol Biotechnol 2006; 69(5):510-4.
11. Kajiyama Si, Harada K, Fukusaki E, Kobayashi A. Single Cell-Based Analysis of Torenia Petal Pigments by A Combination of Arf Excimer Laser Micro Sampling and Nano-High Performance Liquid Chromatography (HPLC)-Mass Spectrometry. J Biosci Bioeng 2006; 102(6):575-8.
12. Ahmadzadeh H, Johnson R D, Thompson L, Arriaga E A. Direct Sampling from Muscle Cross Sections for Electrophoretic Analysis of Individual Mitochondria. Anal Chem 2004; 76(2):315-21.
13. Dahl D B, Cayton J C, Lott P F. Gunshot Residue Analysis: An Applicability Study. Microchem J 1987; 35(3):360-4.
14. Lloyd J B F, King R M. One-Pot Processing of Swabs for Organic Explosives and Firearms Residue Traces. J Forensic Sci 1990; 35(4):956-9.
15. Higbee D J, Douglas R, Smith J, White T P, Bigwarfe P M, Dolan A R. Miniaturization of Electrospray Ionization Mass Spectrometry. Trends Appl Spectros 2002; 4:141-54.
16. Vigneau O, Machuron-Mandard X. A LC-MS Method Allowing the Analysis of HMX and RDX Present at the Picogram Level in Natural Aqueous Samples without A Concentration Step. Talanta 2009; 77(5):1609-13.
17. Bernal Morales E, Revilla Vzquez A L. Simultaneous Determination of Inorganic and Organic Gunshot Residues by Capillary Electrophoresis. J Chromatogr A 2004; 1061 (2):225-33.
18. E. Psillakis, N. Kalogerakis, Developments in Single-Drop Microextraction. Trends Anal. Chem. 21 (2002) 54-64.
19. L. Xu, C. Basheer, H. K. Lee, Developments in Single-Drop Microextraction. J. Chromatogr., A 1152 (2007) 184-192.
20. G. Shen, H. K. Lee, Hollow Fiber-Protected Liquid-Phase Microextraction of Triazine Herbicides. Anal. Chem. 74 (2002) 648-654.
21. H. Liu, P. K. Dasgupta, Analytical Chemistry in a Drop. Solvent Extraction in A Microdrop. Anal. Chem. 68 (1996) 1817-1821.
22. M. A. Jeannot, F. F. Cantwell, Solvent Microextraction into A Single Drop. Anal. Chem. 68 (1996) 2236-2240.
23. W. Liu, H. K. Lee, Continuous-Flow Microextraction Exceeding 1000-Fold Concentration of Dilute Analytes. Anal. Chem. 72 (2000) 4462-4467.
24. Y. He, H. K. Lee, Liquid-Phase Microextraction in A Single Drop of Organic Solvent by using A Conventional Microsyringe. Anal. Chem. 69 (1997) 4634-4640.
25. B. O. Keller, L. Li, Nanoliter Solvent Extraction Combined with Microspot MALDI TOF Mass Spectrometry for the Analysis of Hydrophobic Biomolecules. Anal. Chem. 73 (2001) 2929-2936.
26. M. Sitti, Survey of Nanomanipulation Systems. Nanotechnology, 2001. IEEE-NANO 2001. Proceedings of the 2001 1st IEEE Conference on, 2001, pp. 75.
27. IUPAC, Nomenclature for Liquid-Liquid Distribution (Solvent Extraction). Pure Appl. Chem. 65 (1993) 2373-2396.
28. L. Xu, C. Basheer, H. K. Lee, Chemical Reactions in Liquid-Phase Microextraction. J. Chromatogr., A 1216 (2009) 701-707.
29. E. G. Bligh, W. J. Dyer, A Rapid Method of Total Lipid Extraction and Purification. Can. J. Biochem. Physiol. 37 (1959) 911. [13] N. B. Cech, C. G. Enke, Practical Implications of Some Recent Studies in Electrospray Ionization Fundamentals, Mass Spectrom. Rev. 20 (2001) 362-387.
30. Cech, N. B.; Enke, C. G. Practical Implications of Some Recent Studies in Electrospray Ionization Fundamentals. Mass Spectrometry Reviews. 2001, 20, 362-387.
31. V. N. Schumaker, Cholesterolemic Rabbit Lipoproteins: Serum Lipoproteins of the Cholesterolemic Rabbit. Am. J. Physiol. 184 (1955) 35-42.
32. A. Vega-ríos, H. Villalobos, J. F. Mata-segreda, Acid-Catalyzed Hydrolysis of Triacylglycerols Obeys Monoexponential Kinetics. Int. J. Chem. Kinet. 24 (1992) 887-894.
33. M. Lísa, M. Holcapek, Triacylglycerols Profiling in Plant Oils Important in Food Industry, Dietetics and Cosmetics using High-Performance Liquid Chromatography-Atmospheric Pressure Chemical Ionization Mass Spectrometry. J. Chromatogr., A 1198-1199 (2008) 115-130.
34. A. Smaoui, A. Chérif, Changes in Molecular Species of Triacylglycerols in Developing Cotton Seeds under Salt Stress. Biochem. Soc. Trans. 28 (2000) 902-905.
35. S. G. Yunusova, S. D. Gusakova, A. U. Umarov, Stereospecific Analysis of the Triacylglycerols of Cottonseed Oil. Chem. Nat. Compd. 18 (1982) 396-399.
36. L. A. Jones, C. C. King, Cottonseed Oil. in: Y. H. Hui (Eds). Bailey's Industrial Oil & Fat Products. 5th ed. New York: John Wiley & Sons; 1996. pp. 159-227.
37. Grant, Applied Spectroscopy, 2005.
38. Croxton, Journal of Forensic Sciences, 2006.
39. Marshall, Aspects of Explosive Detection, 2009.
40. Gottfried, Journal of Analytical Atomic Spectrometry, 2008.
41. A. G. Ryder, Surface enhanced Raman scattering for narcotic detection and applications to chemical biology. Current Opinion in Chemical Biology 9 (2005) 489-493.
42. H. K. Katrin Kneippl, Irving Itzkan, Ramachandra R Dasari and Michael S Feld Surface enhanced Raman scattering and biophysics Journal of Physics: Condensed Matter 14 (2002) R597-R624.
43. Garc, iacute, F. J. a-Vidal, and J. B. Pendry, Collective Theory for Surface Enhanced Raman Scattering. Physical Review Letters 77 (1996) 1163.
44. A. Campion, and P. Kambhampati, Surface-enhanced Raman scattering. Chemical Society Reviews 27 (1998) 241-250.
45. K. Kneipp, Y. Wang, H. Kneipp, L. T. Perelman, I. Itzkan, R. R. Dasari, and M. S. Feld, Single Molecule Detection Using Surface-Enhanced Raman Scattering (SERS). Physical Review Letters 78 (1997) 1667.
46. D. S. Grubisha, R. J. Lipert, H.-Y. Park, J. Driskell, and M. D. Porter, Femtomolar Detection of Prostate-Specific Antigen:â€ 0/00 An Immunoassay Based on Surface-Enhanced Raman Scattering and Immunogold Labels. Analytical Chemistry 75 (2003) 5936-5943.
47. B. J. Yakes, R. J. Lipert, J. P. Bannantine, and M. D. Porter, Impact of Protein Shedding on Detection of *Mycobacterium avium* subsp. *paratuberculosis* by a Whole-Cell Immunoassay Incorporating Surface-Enhanced Raman Scattering. Clin. Vaccine Immunol. 15 (2008) 235-242.
48. T.-T. Liu, Y.-H. Lin, C.-S. Hung, T.-J. Liu, Y. Chen, Y.-C. Huang, T.-H. Tsai, H.-H. Wang, D.-W. Wang, J.-K. Wang, Y.-L. Wang, and C.-H. Lin, A High Speed Detection Platform Based on Surface-Enhanced Raman Scattering for Monitoring Antibiotic-Induced Chemical Changes in Bacteria Cell Wall. PLoS ONE 4 (2009) e5470.
49. A. G. Ryder, G. M. O'Connor, and T. J. Glynn, Quantitative analysis of cocaine in solid mixtures using Raman spectroscopy and chemometric methods. Journal of Raman Spectroscopy 31 (2000) 221-227.
50. E. Ali, H. Edwards, M. Hargreaves, and I. Scowen, Raman spectroscopic investigation of cocaine hydrochloride on human nail in a forensic context. Analytical and Bioanalytical Chemistry 390 (2008) 1159-1166.
51. K. Faulds, W. E. Smith, D. Graham, and R. J. Lacey, Assessment of silver and gold substrates for the detection of amphetamine sulfate by surface enhanced Raman scattering (SERS). Analyst 127 (2002) 282-286.
52. S. E. J. Bell, L. A. Fido, N. M. S. Sirimuthu, S. J. Speers, K. L. Peters, and S. H. Cosbey, Screening Tablets for DOB Using Surface-Enhanced Raman Spectroscopy*. Journal of Forensic Sciences 52 (2007) 1063-1067.
53. V. Rana, M. V. Cañamares, T. Kubic, M. Leona, and J. R. Lombardi, Surface-enhanced Raman Spectroscopy for Trace Identification of Controlled Substances: Morphine, Codeine, and Hydrocodone. Journal of Forensic Sciences 56 200-207.
54. B. Sagmuller, B. Schwarze, G. Brehm, and S. Schneider, Application of SERS spectroscopy to the identification of (3,4-methylenedioxy)amphetamine in forensic samples utilizing matrix stabilized silver halides. Analyst 126 (2001) 2066-2071.
55. C. J. Strachan, T. Rades, K. C. Gordon, and J. Rantanen, Raman spectroscopy for quantitative analysis of pharmaceutical solids. Journal of Pharmacy and Pharmacology 59 (2007) 179-192.
56. G. Fini, Applications of Raman spectroscopy to pharmacy. Journal of Raman Spectroscopy 35 (2004) 335-337.
57. D. K. Corrigan, M. Cauchi, S. Piletsky, and S. Mccrossen, Application of Surface-Enhanced Raman Spectroscopy (SERS) for Cleaning Verification in Pharmaceutical Manufacture. PDA Journal of Pharmaceutical Science and Technology 63 (2009) 568-574.
58. N. Wallace, E. Hueske, and G. F. Verbeck, Ultra-trace analysis of illicit drugs from transfer of an electrostatic lift. Science & justice: journal of the Forensic Science Society.
59. N.P.A.T. (Japan), An Electrostatic Method of Lifting Footprints. International Criminal Police Review (1973) 287-292.
60. J. LeMay, Evidence Beneath Your Feet. Law Enforcement Technology 33 (2006) 42-45.
61. C. L. Craig, Evaluation and Comparison of the ElectrostaticDust Print Lifter and the Electrostatic Detection Apparatus on the Development of Footwear Impressions on Paper. Journal of Forensic Sciences 51 (2006) 1556-4029.
62. Murphy, D. J. (2001) Prog. Lipid Res. 40, 325-438.
63. Bartz, R., Li, W. H., Venables, B., Zehmer, J. K., Roth, M. R., Welti, R., Anderson, R. G., Liu, P., and Chapman, K. D. (2007) J. Lipid Res. 48, 837-847.
64. Granneman, J. G., and Moore, H. P. (2008) Trends Endocrinol Metab. 19, 3-9.
65. Zehmer, J. K., Huang, Y., Peng, G., Pu, J., Anderson, R. G., and Liu, P. (2009) Proteomics 9, 914-921.
66. Bozza, P. T., and Viola, J. P. (2010) Prostaglandins Leukot. Essent. Fatty Acids 82, 243-250.
67. Cocchiaro, J. L., Kumar, Y., Fischer, E. R., Hackstadt, T., and Valdivia, R. H. (2008) Proc. Natl. Acad. Sci. U.S.A. 105, 9379-9384.
68. Kumar, Y., Cocchiaro, J., and Valdivia, R. H. (2006) Curr. Biol. 16, 1646-1651.
69. Huang, A. H. C. (1992) Annu Rev. Plant Physiol. Plant Mol. Biol. 43, 177-200.
70. Goodman, J. M. (2008) J. Biol. Chem. 283, 28005-28009.
71. Gocze, P. M., and Freeman, D. A. (1994) Cytometry 17, 151-158.

72. Fukumoto, S., and Fujimoto, T. (2002) Histochem. Cell Biol. 118, 423-428.
73. Guo, Y., Walther, T. C., Rao, M., Stuurman, N., Goshima, G., Terayama, K., Wong, J. S., Vale, R. D., Walter, P., and Farese, R. V. (2008) Nature 453, 657-661.
74. Slack, C. R., Bertaud, W. S., Shaw, B. D., Holland, R., Browse, J., and Wright, H. (1980) Biochem. J. 190, 551-561.
75. Leprince, O., van Aelst, A. C., Pritchard, H. W., and Murphy, D. J. (1997) Planta 204, 109-119.
76. Fujimoto, T., Ohsaki, Y., Cheng, J., Suzuki, M., and Shinohara, Y. (2008) Histochem. Cell Biol. 130, 263-279.
77. Robenek, H., Buers, I., Hofhagel, O., Robenek, M. J., Troyer, D., and Severs, N. J. (2009) Biochim. Biophys. Acta 1791, 408-418.
78. De'barre, D., Supatto, W., Pena, A. M., Fabre, A., Tordjmann, T., Combettes, L., Schanne-Klein, M. C., and Beaurepaire, E. (2006) Nat. Direct Organelle Mass Spectrometry Methods 3, 47-53.
79. van Manen, H. J., Kraan, Y. M., Roos, D., and Otto, C. (2005) Proc. Natl. Acad. Sci. U.S.A. 102, 10159-10164.
80. Cheng, C., Gross, M. L., and Pittenauer, E. (1998) Anal. Chem. 70, 4417-4426.
81. Schmelzer, K., Fahy, E., Subramaniam, S., and Dennis, E. A. (2007) Methods Enzymol. 432, 171-183.
82. Zehethofer, N., and Pinto, D. M. (2008) Analytica Chimica Acta 627, 62-70.
83. Sud, M., Fahy, E., Cotter, D., Brown, A., Dennis, E. A., Glass, C. K., Merrill, A. H., Jr., Murphy, R. C., Raetz, C. R., Russell, D. W., and Subramaniam, S. (2007) Nucleic Acids Res. 35, D527-532.
84. Murphy, R. C., Hankin, J. A., and Barkley, R. M. (2009) J. Lipid Res. 50, S317-322.
85. Brunelle, A., and Lapre'vote, O. (2009) Anal. Bioanal. Chem. 393, 31-35.
86. Dill, A. L., Ifa, D. R., Manicke, N. E., Ouyang, Z., and Cooks, R. G. (2009) J. Chromatogr. B 877, 2883-2889.
87. Brown, J. M., Hoffmann, W. D., Alvey, C. M., Wood, A. R., Verbeck, G. F., and Petros, R. A. (2010) Anal. Biochem. 398, 7-14.
88. Ledbetter, N. L., Walton, B. L., Davila, P., Hoffmann, W. D., Ernest, R. N., and Verbeck, G. F. (2010) J. Forensic Sci. 55, 1218-1221.
89. Chapman, K. D., Austin-Brown, S., Sparace, S. A., Kinney, A. J., Ripp, K. G., Pirtle, I. L., and Pirtle, R. M. (2001) J. Am. Oil Chem. Soc. 78, 941-947.
90. Chapman, K. D., Neogi, P. B., Hake, K. D., Stawska, A. A., Speed, T. R., Cotter, M. Q., Garrett, D. C., Kerby, T., Richardson, C. D., Ayre, B. G., Ghosh, S., and Kinney, A. J. (2008) Crop Sci. 48, 1470-1481.
91. Chapman, K. D., and Trelease, R. N. (1991) J. Cell Biol. 115, 995-1007.
92. Tzen, J. T., Lai, Y. K., Chan, K. L., and Huang, A. H. (1990) Plant Physiol. 94, 1282-1289.
93. Bligh, E. G., and Dyer, W. J. (1959) Can. J. Physiol. Pharmacol. 37, 911-917.
94. Byrdwell, W. C. (2005) Lipids 40, 383-417.
95. Schmid, K. M., and Patterson, G. W. (1988) Phytochemistry 27, 2831-2834.
96. Yang, Z., and Ohlrogge, J. B. (2009) Plant Physiol. 150, 1981-1989.

What is claimed is:

1. A fingerprint lift method for detecting trace amounts of one or more analytes from a solid substrate comprising the steps of:
providing a cast, a mould or any other solid impression of a human finger, wherein the cast or the mould comprises one or more ridges duplicating the ridges found on the human finger;
saturating the cast, the mould or the solid impression with an oil, a grease or a lipid by a spraying, a dipping or a coating process;
lifting the analytes from the solid substrate by pressing or contacting the cast, the mould or the solid impression with the substrate;
transferring the lifted analytes from the solid substrate to a microscopic slide or any other suitable solid support; and
detecting the one or more analytes by generating a mass spectrum in a mass spectrometer, wherein the detection is done by identifying a m/z ratio of the analytes in the mass spectrum.

2. The method of claim 1, wherein the one or more analytes comprise explosives, drugs, and narcotics.

3. The method of claim 1, wherein the analyte is cocaine.

4. The method of claim 1, wherein the analyte is nitroglycerine (NG) and dinitrotoluene (DNT).

5. The method of claim 1, wherein the mass spectrometer system is equipped with a nanospray source.

6. The method of claim 5, wherein the system further comprises:
an inverted microscopic stage mounted with or capable of holding the solid support comprising the one or more analytes; and
an extraction system for an extraction of the one or more analytes from the support followed by a transfer to a detection system, wherein the detection system is coupled to the extraction system, wherein the extraction system comprises:
a workstation comprising a plurality of moveable nanopositioners, wherein the nanopositioners are capable of three-dimensional movement in a X-Y-Z plane, wherein the nanopositioners hold one or more probes, grippers, capillary tips or any other suitable accessory for an extraction and transfer of a liquid phase;
a pressure injector for delivering a pressurized extraction solvent through the capillary tip, wherein the capillary tip is placed in close proximity to the support;
a voltage source;
a joystick or a digital controller for controlling the movement of the nanopositioners; and
a mass spectrometer that is off line or is connected to the extraction system for receiving the one or more analytes transferred by the extraction system.

7. The method of claim 5, wherein the method further comprises the step of generating a background mass spectrum comprising any other analytes that are or may be expected to be present, the oil, the grease or the lipids or both, wherein the background spectrum is used to correct for interferences from the other analytes, the oil, the grease or the lipids or both.

8. A fingerprint lift method for detecting trace amounts of one or more dissolved analytes from a liquid comprising the steps of:
evaporating the liquid to obtain a solid residue, wherein the solid residue comprises the one or more analytes to be detected;
providing a cast, a mould or any other solid impression of a human finger, wherein the cast or the mould comprises one or more ridges duplicating the ridges found on the human finger;

saturating the cast, the mould or the solid impression with an oil, a grease or a lipid by a spraying, dipping or a coating process;

lifting the analytes from the solid residue by pressing or contacting the cast, the mould or the solid impression with the residue;

transferring the lifted analytes from the solid residue to a microscopic slide or any other suitable solid support; and detecting the one or more analytes by generating a mass spectrum in a mass spectrometer, wherein the detection is done by identifying a m/z ratio of the analytes in the mass spectrum.

9. The method of claim 8, wherein the one or more analytes comprise explosives, drugs, and narcotics.

10. The method of claim 8, wherein the analyte is cocaine.

11. The method of claim 8, wherein the analyte is nitroglycerine (NG) and dinitrotoluene (DNT).

12. The method of claim 8, wherein the mass spectrometer system is equipped with a nanospray source.

13. The method of claim 12, wherein the system further comprises:

an inverted microscopic stage mounted with or capable of holding the solid support comprising the one or more analytes; and an extraction system for an extraction of the one or more analytes from the support followed by a transfer to a detection system, wherein the detection system is coupled to the extraction system, wherein the extraction system comprises:

a workstation comprising a plurality of moveable nanopositioners, wherein the nanopositioners are capable of three-dimensional movement in a X-Y-Z plane, wherein the nanopositioners hold one or more probes, grippers, capillary tips or any other suitable accessory for an extraction and transfer of a liquid phase;

a pressure injector for delivering a pressurized extraction solvent through the capillary tip, wherein the capillary tip is placed in close proximity to the support;

a voltage source;

a joystick or a digital controller for controlling the movement of the nanopositioners; and a mass spectrometer that is off line or is connected to the extraction system for receiving the one or more analytes transferred by the extraction system.

14. The method of claim 13, wherein the extraction solvent comprises water, polar organic and inorganic solvents, mixtures of polar and non-polar solvents, and combinations and modifications thereof.

15. The method of claim 8, wherein the method further comprises the step of generating a background mass spectrum comprising any other analytes that may be expected to be present, the oil, the grease or the lipids or both, wherein the background spectrum is used to correct for interferences from the other analytes, the oil, the grease or the lipids or both.

16. A method for lifting prints, detecting one or more analytes, drug residues, or contaminants in a mixture, or any combinations thereof comprising the steps of:

placing an uncoated first substrate or a first film on top of and in contact with the print, the one or more analytes, drug residues, contaminants in a mixture, or any combinations thereof, wherein the analyte, the drug residue, contaminants in the mixture, or any combinations thereof adhere to and are collected onto the surface of the first substrate;

placing a coated second substrate or a second film on top of and in contact with the first substrate or first film comprising the collected one or more analytes, drug residues, contaminants in a mixture, or any combinations thereof, wherein the second substrate or the second film is a metal coated film; and applying a voltage to the second substrate or the film, wherein the application of the voltage results in a lifting, a retrieval or an adhesion of the print, the one or more analytes, drug residues, contaminants in a mixture, or any combinations thereof due to a combination of electrostatic and conductive forces.

17. The method of claim 16, further comprising the step of detecting the one or more analytes, the drug residues, contaminants in a mixture, or any combinations thereof by Raman spectroscopy or by generation of a mass spectrum in a mass spectrometer, wherein the detection is done by identifying a m/z ratio of the analytes in the mass spectrum.

18. The method of claim 17, wherein the step of detection is performed by Surface Enhanced Raman Scattering (SERS).

19. The method of claim 17, wherein the step of detection is performed by a mass spectrometer system equipped with a nanospray source.

20. The method of claim 16, wherein the one or more analytes comprise explosives, drugs, narcotics, or any combinations thereof wherein the drugs are selected from the group consisting of cocaine, amphetamines, codeine, hydrocodone, and crystal meth.

21. The method of claim 16, wherein the substrate or the film comprises a polymer, a polyester, or any conductive material capable of lifting the one or more analytes from a surface.

22. The method of claim 16, wherein the film coating comprises metals selected from gold, silver, or any combinations thereof, wherein the metals are deposited by physical vapor deposition.

23. The method of claim 16, wherein the second substrate or film is coated with gold.

24. The method of claim 16, wherein the first substrate or film and the second substrate or film may comprise same or different materials.

25. The method of claim 16, wherein a thickness of the metal coated films ranges from 25 nm-100 nm.

* * * * *